US007399741B2

(12) United States Patent
Lamb et al.

(10) Patent No.: US 7,399,741 B2
(45) Date of Patent: Jul. 15, 2008

(54) NOTCH

(75) Inventors: Jonathan Robert Lamb, Edinburgh (GB); Margaret Jane Dallman, London (GB); Gerard Francis Hoyne, Midlothian (GB)

(73) Assignee: Celldex Therapeutics Limited, Cambridge (GB)

( * ) Notice: Subject to any disclaimer, the term of this patent is extended or adjusted under 35 U.S.C. 154(b) by 54 days.

(21) Appl. No.: 10/877,563

(22) Filed: Jun. 25, 2004

(65) Prior Publication Data

US 2004/0241180 A1 Dec. 2, 2004

Related U.S. Application Data

(63) Continuation of application No. 09/310,685, filed on May 4, 1999, now Pat. No. 6,887,475, which is a continuation-in-part of application No. PCT/GB97/03058, filed on Nov. 6, 1997.

(30) Foreign Application Priority Data

| Nov. 7, 1996 | (GB) | 9623236.8 |
| Jul. 24, 1997 | (GB) | 9715674.9 |
| Sep. 11, 1997 | (GB) | 9719350.2 |

(51) Int. Cl.
    A61K 45/00 (2006.01)
    A61K 31/00 (2006.01)

(52) U.S. Cl. .................. 514/2; 424/278.1; 424/810

(58) Field of Classification Search .......... 514/2; 424/278.1
    See application file for complete search history.

(56) References Cited

U.S. PATENT DOCUMENTS 6,004,924 A  12/1999  Ish-Horowicz et al.

FOREIGN PATENT DOCUMENTS

| WO | WO 92/19734 | 11/1992 |
| WO | WO 94/07474 | 4/1994 |
| WO | WO 95/19779 | 7/1995 |
| WO | WO 95/21258 | 8/1995 |
| WO | WO 96/27610 | 9/1996 |
| WO | WO 97/01571 | 1/1997 |
| WO | WO 97/11716 | 4/1997 |
| WO | WO 97/19172 | 5/1997 |

OTHER PUBLICATIONS

Atkinson, MA et al. Nature Medicine [1999] 5(6):601-604.*
Tisch, R et al. Proc. Nat. Acad. Sci. (USA). [1994] 91:437-438.*
Hoyne, G.F., et al., "Serrate 1-Induced Notch Signaling Regulates The Decision Between Immunity And Tolerance Made By Peripheral CD4+ T Cells", International Immunology, vol. 12, No. 2, pp. 177-185, 1999.

Hoyne, G.F., et al., "Linked Suppression in Peripheral T Cell Tolerance to the House Dust Mite Allergen Der p 1", Int'l Archives of Allergy and Immunology, vol. 118, pp. 122-124, 1999.
Hoyne, G.F., et al., "T-Cell Regulation of Peripheral Tolerance and Immunity: The Potential Role for Notch Signalling", Immunology, vol. 100, pp. 281-288, 2000.
Hoyne, G.F., et al., "Notch Signalling in the Regulation of Peripheral Immunity", Immunological Reviews, vol. 182, pp. 215-227, 2001.
McKenzie, G.J., et al., "Notch Signalling in the Regulation of Peripheral T-cell Function", Seminars in Cell & Development Biology, vol. 14, pp. 127-134, 2003.
Dallman, M.J., et al., "Notch Signalling in the Peripheral Immune System", Novartis Foundation Symposium, vol. 252, pp. 268-278, 2003.
Wong, K.K., et al., "Notch Litigation by Delta 1 Inhibits Peripheral Immune Responses to Transplantation Antigens by CD8+ Cell-dependent Mechanism", The Journal of Clinical Investigation, vol. 112, No. 11, pp. 1741-1750, Dec. 2003.
Hasserjian, R.P., et al., "Modulated Expression of Notch 1 During Thymocyte Development", Blood, vol. 88, No. 3, pp. 970-976, Aug. 1996.
Jones, ND et al. Journal of Immunology (2001) 166:2824-1830.
Tufveson, G. et al. Immunological Reviews (1993) 136: 99-109.
Artavanis-Tsakonas et al. (1995) Science 268:225-232.
Jaleco et al (2001) Journal of Experimental Medicine 194 (7): F43-46.
Janeway et al. (1999) Immunobiology Fourth edition, Garland Press, NY, p. 246.
Hoyne, G.F., "Notch Signaling in the Immune System," Journal of Leukocyte Biology, vol. 74, pp. 971-981, 2003.
Robey et al., "An Activated Form of Notch Influences the Choice Between CD4 and CD8 T Cell Lineages." Cell, vol. 87. Nov. 1, 1996. pp. 483-492.
Artavanis-Tsakonas et al., "Notch Signaling." Science. vol. 268. Apr. 14, 1995. pp. 225-232.
Qin et al., "Infectious Transplantation Tolerance." Science, vol. 259, Feb. 12, 1993. pp. 974-977.
Isobe et al., "Specific Acceptance of Cardiac Allograft After Treatment with Antibodies to ICAM-1 and LFA-1," Science, vol. 255, Feb. 18, 1992. pp. 1125-1127.
Robey, "Notch in Vertebrates." Current Opinion in Genetics and Development, vol. 7, 1997, pp. 551-557.
Medzhitov et al., "A Human Homologue of the Drosophila Toll Protein Signals Activation of Adaptive Immunity." Nature, Jul. 1997, pp. 394-396.

(Continued)

*Primary Examiner*—Christina Chan
*Assistant Examiner*—F. Pierre VanderVegt
(74) *Attorney, Agent, or Firm*—Frommer Lawrence & Haug LLP; Thomas J. Kowalski; Anne-Marie C. Yvon

(57) ABSTRACT

The present invention relates to the use of therapeutic compounds in the modification of T-cell, T-cell-antigen presenting cell (APC) interactions and the interactions between pathogenic organisms and immunocompetent cells of a host. In particular it relates to the use of these compounds in the modulation of the interaction between Notch proteins and their ligands and to the use of such compounds in the therapy of conditions such as graft rejection, autoimmunity, allergy, and asthma and infectious diseases.

5 Claims, 52 Drawing Sheets

OTHER PUBLICATIONS

"Peptide(2) Encoded by Human Genes Delta-1 and Serrate-1 Suppress Proliferation and Differentiation of Undifferentiated Human Blood Cell," Derwent abstract based on Japanese Appln. No. 97-298100. May 29, 1997.

Berthold Bettenhausen, et al., Transient And Restricted Expression During Mouse Embryogenesis of DIII, A Murine Gene Closely Related To Drosophila Delta, Development (1995) vol. 121, p. 2407-2418.

Ajay Chitnis, et al., Primary Neurogenesis In Xenopus Embryos Regulated By A Homologue Of The Drosophila Neurogenic Gene Delta, Nature (1995) vol. 375, p. 761-766.

GenBank Accession No. L42229.

Domingos Henrique, et al., Expression Of A Delta Homologue In Prospective Neurons In The Chick, Nature (1995) vol. 375, p. 787-790.

GenBank Accession No. U26590.

Claire E. Lindsell, et al., Jagged: A Mammalian Ligand That Activated Notch1, Cell (1995) vol. 80, p. 909-917.

Gen Bank Accession No. L38483.

J.A. Harper, et al., Notch Signaling In Development And Disease, Clin. Genet. (2003) vol. 64, p. 461-472.

Takahiro Suzuki, et al., Notch Signaling In Hematopoietic Stem Cells, International Journal of Hematology (2005) vol. 82, p. 285-294.

La Motte-Mohs Ross, N. et al., FASEB Journal, vol. 18, Abstracts 83-34.

* cited by examiner

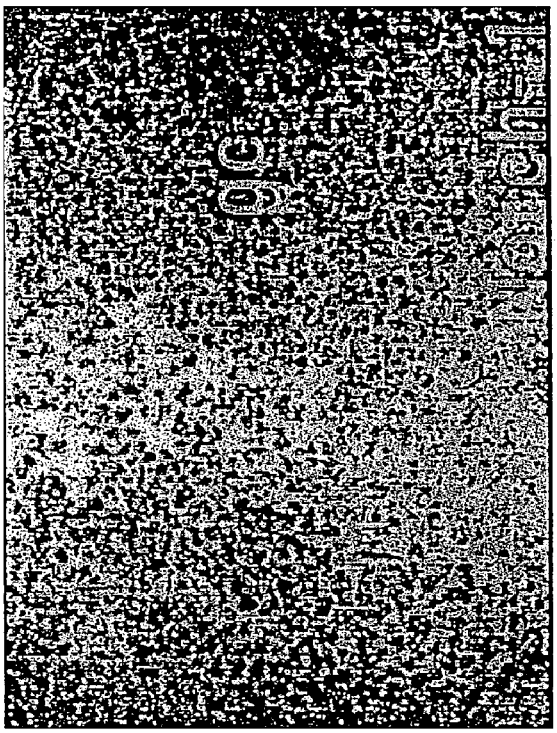
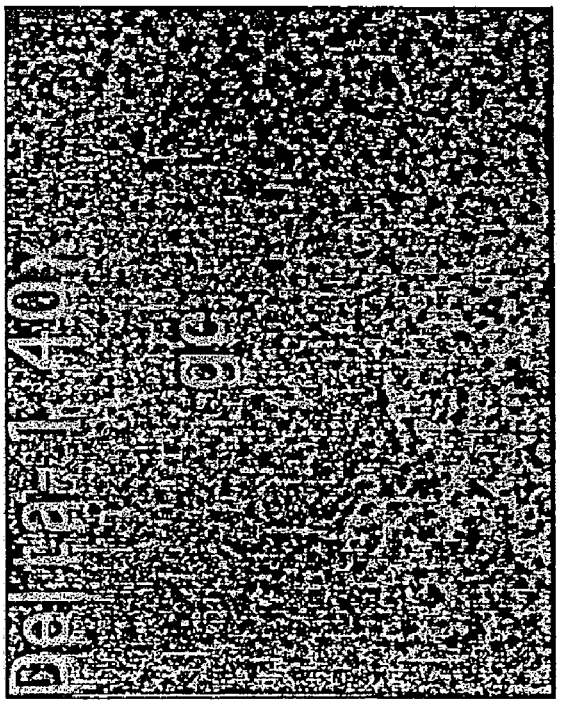
3 wt spleen
gc = germinal centre
FIG. 1

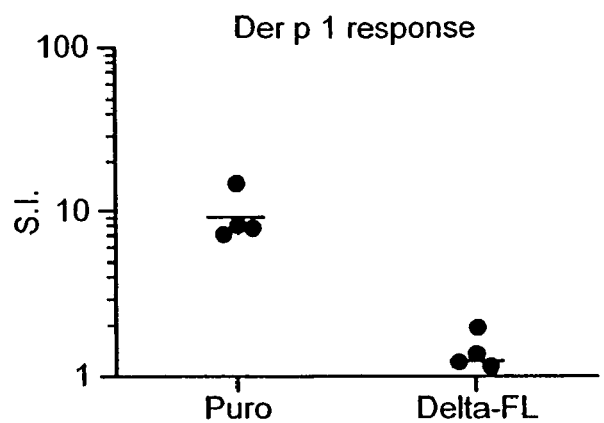
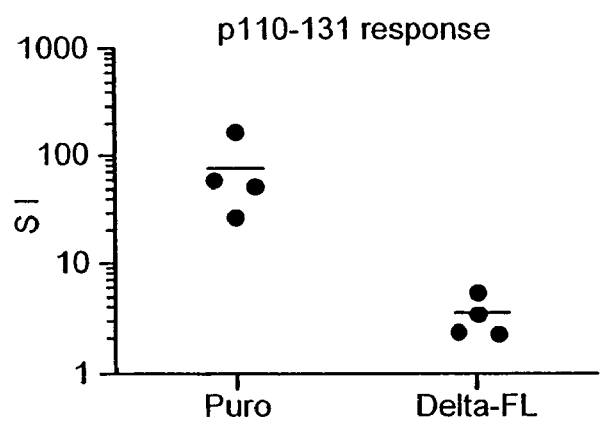
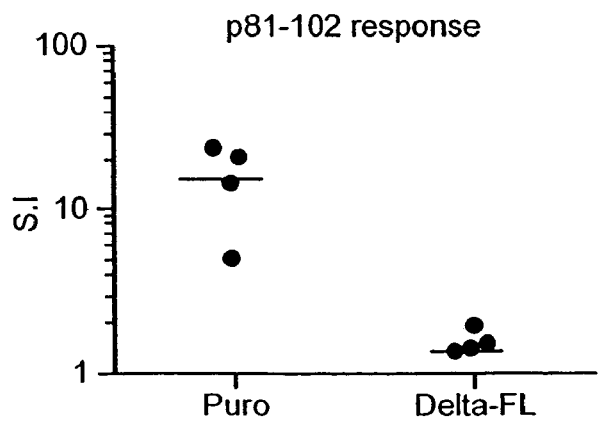
FIG. 4

GAATTCGGAG GAATTATTCA AAACATAAAC ACAATAAACA ATTTGAGTAG TTGCCGCACA    60

CACACACACA CACAGCCCGT GGATTATTAC ACTAAAAGCG ACACTCAATC CAAAAAATCA    120

GCAACAAAAA CATCAATAAA C ATG CAT TGG ATT AAA TGT TTA TTA ACA GCA    171
                        Met His Trp Ile Lys Cys Leu Leu Thr Ala
                         1           5                       10

TTC ATT TGC TTC ACA GTC ATC GTG CAG GTT CAC AGT TCC GGC AGC TTT    219
Phe Ile Cys Phe Thr Val Ile Val Gln Val His Ser Ser Gly Ser Phe
             15                  20                  25

GAG TTG CGC CTG AAG TAC TTC AGC AAC GAT CAC GGG CGG GAC AAC GAG    267
Glu Leu Arg Leu Lys Tyr Phe Ser Asn Asp His Gly Arg Asp Asn Glu
         30                  35                  40

GGT CGC TGC TGC AGC GGG GAG TCG GAC GGA GCG ACG GGC AAG TGC CTG    315
Gly Arg Cys Cys Ser Gly Glu Ser Asp Gly Ala Thr Gly Lys Cys Leu
             45                  50                  55

GGC AGC TGC AAG ACG CGG TTT CGC GTC TGC CTA AAG CAC TAC CAG GCC    363
Gly Ser Cys Lys Thr Arg Phe Arg Val Cys Leu Lys His Tyr Gln Ala
         60                  65                  70

ACC ATC GAC ACC ACC TCC CAG TGC ACC TAC GGG GAC GTG ATC ACG CCC    411
Thr Ile Asp Thr Thr Ser Gln Cys Thr Tyr Gly Asp Val Ile Thr Pro
 75                  80                  85                  90

ATT CTC GGC GAG AAC TCG GTC AAT CTG ACC GAC GCC CAG CGC TTC CAG    459
Ile Leu Gly Glu Asn Ser Val Asn Leu Thr Asp Ala Gln Arg Phe Gln
             95                 100                 105

AAC AAG GGC TTC ACG AAT CCC ATC CAG TTC CCC TTC TCG TTC TCA TGG    507
Asn Lys Gly Phe Thr Asn Pro Ile Gln Phe Pro Phe Ser Phe Ser Trp
         110                 115                 120

FIG. 10A

```
CCG GGT ACC TTC TCG CTG ATC GTC GAG GCC TGG CAT GAT ACG AAC AAT    555
Pro Gly Thr Phe Ser Leu Ile Val Glu Ala Trp His Asp Thr Asn Asn
        125                 130                 135

AGC GGC AAT GCG CGA ACC AAC AAG CTC CTC ATC CAG CGA CTC TTG GTG    603
Ser Gly Asn Ala Arg Thr Asn Lys Leu Leu Ile Gln Arg Leu Leu Val
        140                 145                 150

CAG CAG GTA CTG GAG GTG TCC TCC GAA TGG AAG ACG AAC AAG TCG GAA    651
Gln Gln Val Leu Glu Val Ser Ser Glu Trp Lys Thr Asn Lys Ser Glu
155                 160                 165                 170

TCG CAG TAC ACG TCG CTG GAG TAC GAT TTC CGT GTC ACC TGC GAT CTC    699
Ser Gln Tyr Thr Ser Leu Glu Tyr Asp Phe Arg Val Thr Cys Asp Leu
        175                 180                 185

AAC TAC TAC GGA TCC GGC TGT GCC AAG TTC TGC CGG CCC CGC GAC GAT    747
Asn Tyr Tyr Gly Ser Gly Cys Ala Lys Phe Cys Arg Pro Arg Asp Asp
        190                 195                 200

TCA TTT GGA CAC TCG ACT TGC TCG GAG ACG GGC GAA ATT ATC TGT TTG    795
Ser Phe Gly His Ser Thr Cys Ser Glu Thr Gly Glu Ile Ile Cys Leu
        205                 210                 215

ACC GGA TGG CAG GGC GAT TAC TGT CAC ATA CCC AAA TGC GCC AAA GGC    843
Thr Gly Trp Gln Gly Asp Tyr Cys His Ile Pro Lys Cys Ala Lys Gly
        220                 225                 230

TGT GAA CAT GGA CAT TGC GAC AAA CCC AAT CAA TGC GTT TGC CAA CTG    891
Cys Glu His Gly His Cys Asp Lys Pro Asn Gln Cys Val Cys Gln Leu
235                 240                 245                 250

GGC TGG AAG GGA GCC TTG TGC AAC GAG TGC GTT CTG GAA CCG AAC TGC    939
Gly Trp Lys Gly Ala Leu Cys Asn Glu Cys Val Leu Glu Pro Asn Cys
        255                 260                 265
```

FIG. 10B

```
ATC CAT GGC ACC TGC AAC AAA CCC TGG ACT TGC ATC TGC AAC GAG GGT         987
Ile His Gly Thr Cys Asn Lys Pro Trp Thr Cys Ile Cys Asn Glu Gly
        270                 275                 280

TGG GGA GGC TTG TAC TGC AAC CAG GAT CTG AAC TAC TGC ACC AAC CAC        1035
Trp Gly Gly Leu Tyr Cys Asn Gln Asp Leu Asn Tyr Cys Thr Asn His
        285                 290                 295

AGA CCC TGC AAG AAT GGC GGA ACC TGC TTC AAC ACC GGC GAG GGA TTG        1083
Arg Pro Cys Lys Asn Gly Gly Thr Cys Phe Asn Thr Gly Glu Gly Leu
        300                 305                 310

TAC ACA TGC AAA TGC GCT CCA GGA TAC AGT GGT GAT GAT TGC GAA AAT        1131
Tyr Thr Cys Lys Cys Ala Pro Gly Tyr Ser Gly Asp Asp Cys Glu Asn
315                 320                 325                 330

GAG ATC TAC TCC TGC GAT GCC GAT GTC AAT CCC TGC CAG AAT GGT GGT        1179
Glu Ile Tyr Ser Cys Asp Ala Asp Val Asn Pro Cys Gln Asn Gly Gly
            335                 340                 345

ACC TGC ATC GAT GAG CCG CAC ACA AAA ACC GGC TAC AAG TGT CAT TGC        1227
Thr Cys Ile Asp Glu Pro His Thr Lys Thr Gly Tyr Lys Cys His Cys
        350                 355                 360

GCC AAC GGC TGG AGC GGA AAG ATG TGC GAG GAG AAA GTG CTC ACG TGT        1275
Ala Asn Gly Trp Ser Gly Lys Met Cys Glu Glu Lys Val Leu Thr Cys
        365                 370                 375

TCG GAC AAA CCC TGT CAT CAG GGA ATC TGC CGC AAC GTT CGT CCT GGC        1323
Ser Asp Lys Pro Cys His Gln Gly Ile Cys Arg Asn Val Arg Pro Gly
        380                 385                 390

TTG GGA AGC AAG GGT CAG GGC TAC CAG TGC GAA TGT CCC ATT GGC TAC        1371
Leu Gly Ser Lys Gly Gln Gly Tyr Gln Cys Glu Cys Pro Ile Gly Tyr
395                 400                 405                 410
```

FIG. 10C

```
AGC GGA CCC AAC TGC GAT CTC CAG CTG GAC AAC TGC AGT CCG AAT CCA    1419
Ser Gly Pro Asn Cys Asp Leu Gln Leu Asp Asn Cys Ser Pro Asn Pro
            415                 420                 425

TGC ATA AAC GGT GGA AGC TGT CAG CCG AGC GGA AAG TGT ATT TGC CCA    1467
Cys Ile Asn Gly Gly Ser Cys Gln Pro Ser Gly Lys Cys Ile Cys Pro
            430                 435                 440

GCG GGA TTT TCG GGA ACG AGA TGC GAG ACC AAC ATT GAC GAT TGT CTT    1515
Ala Gly Phe Ser Gly Thr Arg Cys Glu Thr Asn Ile Asp Asp Cys Leu
            445                 450                 455

GGC CAC CAG TGC GAG AAC GGA GGC ACC TGC ATA GAT ATG GTC AAC CAA    1563
Gly His Gln Cys Glu Asn Gly Gly Thr Cys Ile Asp Met Val Asn Gln
            460                 465                 470

TAT CGC TGC CAA TGC GTT CCC GGT TTC CAT GGC ACC CAC TGT AGT AGC    1611
Tyr Arg Cys Gln Cys Val Pro Gly Phe His Gly Thr His Cys Ser Ser
475                 480                 485                 490

AAA GTT GAC TTG TGC CTC ATC AGA CCG TGT GCC AAT GGA GGA ACC TGC    1659
Lys Val Asp Leu Cys Leu Ile Arg Pro Cys Ala Asn Gly Gly Thr Cys
            495                 500                 505

TTG AAT CTC AAC AAC GAT TAC CAG TGC ACC TGT CGT GCG GGA TTT ACT    1707
Leu Asn Leu Asn Asn Asp Tyr Gln Cys Thr Cys Arg Ala Gly Phe Thr
            510                 515                 520

GGC AAG GAT TGC TCT GTG GAC ATC GAT GAG TGC AGC AGT GGA CCC TGT    1755
Gly Lys Asp Cys Ser Val Asp Ile Asp Glu Cys Ser Ser Gly Pro Cys
            525                 530                 535

CAT AAC GGC GGC ACT TGC ATG AAC CGC GTC AAT TCG TTC GAA TGC GTG    1803
His Asn Gly Gly Thr Cys Met Asn Arg Val Asn Ser Phe Glu Cys Val
            540                 545                 550
```

FIG. 10D

```
TGT GCC AAT GGT TTC AGG GGC AAG CAG TGC GAT GAG GAG TCC TAC GAT      1851
Cys Ala Asn Gly Phe Arg Gly Lys Gln Cys Asp Glu Glu Ser Tyr Asp
555             560             565             570

TCG GTG ACC TTC GAT GCC CAC CAA TAT GGA GCG ACC ACA CAA GCG AGA      1899
Ser Val Thr Phe Asp Ala His Gln Tyr Gly Ala Thr Thr Gln Ala Arg
            575             580             585

GCC GAT GGT TTG ACC AAT GCC CAG GTA GTC CTA ATT GCT GTT TTC TCC      1947
Ala Asp Gly Leu Thr Asn Ala Gln Val Val Leu Ile Ala Val Phe Ser
        590             595             600

GTT GCG ATG CCT TTG GTG GCG GTT ATT GCG GCG TGC GTG GTC TTC TGC      1995
Val Ala Met Pro Leu Val Ala Val Ile Ala Ala Cys Val Val Phe Cys
    605             610             615

ATG AAG CGC AAG CGT AAG CGT GCT CAG GAA AAG GAC GAC GCG GAG GCC      2043
Met Lys Arg Lys Arg Lys Arg Ala Gln Glu Lys Asp Asp Ala Glu Ala
620             625             630

AGG AAG CAG AAC GAA CAG AAT GCG GTG GCC ACA ATG CAT CAC AAT GGC      2091
Arg Lys Gln Asn Glu Gln Asn Ala Val Ala Thr Met His His Asn Gly
635             640             645             650

AGT GGG GTG GGT GTA GCT TTG GCT TCA GCC TCT CTG GGC GGC AAA ACT      2139
Ser Gly Val Gly Val Ala Leu Ala Ser Ala Ser Leu Gly Gly Lys Thr
            655             660             665

GGC AGC AAC AGC GGT CTC ACC TTC GAT GGC GGC AAC CCG AAT ATC ATC      2187
Gly Ser Asn Ser Gly Leu Thr Phe Asp Gly Gly Asn Pro Asn Ile Ile
        670             675             680

AAA AAC ACC TGG GAC AAG TCG GTC AAC AAC ATT TGT GCC TCA GCA GCA      2235
Lys Asn Thr Trp Asp Lys Ser Val Asn Asn Ile Cys Ala Ser Ala Ala
    685             690             695
```

FIG. 10E

```
GCA GCG GCG GCG GCG GCA GCA GCG GCG GAC GAG TGT CTC ATG TAC GGC    2283
Ala Ala Ala Ala Ala Ala Ala Ala Ala Asp Glu Cys Leu Met Tyr Gly
700                 705                 710

GGA TAT GTG GCC TCG GTG GCG GAT AAC AAC AAT GCC AAC TCA GAC TTT    2331
Gly Tyr Val Ala Ser Val Ala Asp Asn Asn Asn Ala Asn Ser Asp Phe
715                 720                 725                 730

TGT GTG GCT CCG CTA CAA AGA GCC AAG TCG CAA AAG CAA CTC AAC ACC    2379
Cys Val Ala Pro Leu Gln Arg Ala Lys Ser Gln Lys Gln Leu Asn Thr
            735                 740                 745

GAT CCC ACG CTC ATG CAC CGC GGT TCG CCG GCA GGC AGC TCA GCC AAG    2427
Asp Pro Thr Leu Met His Arg Gly Ser Pro Ala Gly Ser Ser Ala Lys
                750                 755                 760

GGA GCG TCT GGC GGA GGA CCG GGA GCG GCG GAG GGC AAG AGG ATC TCT    2475
Gly Ala Ser Gly Gly Gly Pro Gly Ala Ala Glu Gly Lys Arg Ile Ser
765                 770                 775

GTT TTA GGC GAG GGT TCC TAC TGT AGC CAG CGT TGG CCC TCG TTG GCG    2523
Val Leu Gly Glu Gly Ser Tyr Cys Ser Gln Arg Trp Pro Ser Leu Ala
780                 785                 790

GCG GCG GGA GTG GCC GGA GCC TGT TCA TCC CAG CTA ATG GCT GCA GCT    2571
Ala Ala Gly Val Ala Gly Ala Cys Ser Ser Gln Leu Met Ala Ala Ala
795                 800                 805                 810

TCG GCA GCG GGC AGC GGA GCG GGG ACG GCG CAA CAG CAG CGA TCC GTG    2619
Ser Ala Ala Gly Ser Gly Ala Gly Thr Ala Gln Gln Gln Arg Ser Val
            815                 820                 825

GTC TGC GGC ACT CCG CAT ATG TAACTCCAAA AATCCGGAAG GGCTCCTGGT       2670
Val Cys Gly Thr Pro His Met
                830
AAATCCGGAG AAATCCGCAT GGAGGAGCTG ACAGCACATA CACAAAGAAA AGACTGGGTT  2730
GGGTTCAAAA TGTGAGAGAG ACGCCAAAAT GTTGTTGTTG ATTGAAGCAG TTTAGTCGTC  2790
ACGAAAAATG AAAAATCTGT AACAGGCATA ACTCGTAAAC TCCCTAAAAA ATTTGTATAG  2850
TAATTAGCAA AGCTGTGACC CAGCCGTTTC GATCCCGAAT TC                    2892
                                                                    F
```

FIG. 10F

```
         10         20         30         40         50         60
GAATTCCCCT CCCCCCTTTT TCCATGCAGC TGATCTAAAA GGGAATAAAA GGCTGCGCAT
         70         80         90        100        110        120
AATCATAATA ATAAAAGAAG GGGAGCGCGA GAGAAGGAAA GAAAGCCGGG AGGTGGAAGA
        130        140        150        160        170        180
GGAGGGGGAG CGTCTCAAAG AAGCGATCAG AATAATAAAA GGAGGCCGGG CTCTTTGCCT
        190        200        210        220        230        240
TCTGGAAGGG GCCGCTCTTG AAAGGGCTTT TGAAAAGTGG TGTTGTTTTC CAGTCGTGCA
        250        260        270        280        290        300
TGCTCCAATC GGCGGAGTAT ATTAGAGCCG GACGCGGCC GCAGGGGCAG CGGCGACGGC
        310        320        330        340        350        360
AGCACCGGCG GCAGCACCAG CGCGAACAGC AGCGGCGGCG TCCCGAGTGC CCGCGGCGGC
        370        380        390        400        410        420
GCGCGCAGCG ATGCGTTCCC CACGGACACG CGGCCGGTCC GGGCGCCCCC TAAGCCTCCT
            M   R   S   P   R   T   R   G   R   S   G   R   P   L   S   L L>
        430        440        450        460        470        480
GCTCGCCCTG CTCTGTGCCC TGCGAGCCAA GGTGTGTGGG GCCTCGGGTC AGTTCGAGTT
   L   A   L   L   C   A   L   R   A   K   V   C   G   A   S   G   Q   F   E L>
        490        500        510        520        530        540
GGAGATCCTG TCCATGCAGA ACGTGAACGG GGAGCTGCAG AACGGGAACT GCTGCGGCGG
   E   I   L   S   M   Q   N   V   N   G   E   L   Q   N   G   N   C   C   G G>
        550        560        570        580        590        600
CGCCCGGAAC CCGGGAGACC GCAAGTGCAC CCGCGACGAG TGTGACACAT ACTTCAAAGT
   A   R   N   P   G   D   R   K   C   T   R   D   E   C   D   T   Y   F   K V>
        610        620        630        640        650        660
GTGCCTCAAG GAGTATCAGT CCCGCGTCAC GGCCGGGGGG CCCTGCAGCT TCGGCTCAGG
   C   L   K   E   Y   Q   S   R   V   T   A   G   G   P   C   S   F   G   S G>
        670        680        690        700        710        720
GTCCACGCCT GTCATCGGGG GCAACACCTT CAACCTCAAG GCCAGCCGCG GCAACGACCC
   S   T   P   V   I   G   G   N   T   F   N   L   K   A   S   P   G   N   D P>
        730        740        750        760        770        780
GAACCGCATC GTGCTGCCTT TCAGTTTCGC CTGGCCGAGG TCCTATACGT TGCTTGTGGA
   N   R   I   V   L   P   F   S   F   A   W   P   R   S   Y   T   L   L   V E>
        790        800        810        820        830        840
GGCGTGGGAT TCCAGTAATG ACACCGTTCA ACCTGACAGT ATTATTGAAA AGGCTTCTCA
   A   W   D   S   S   N   D   T   V   Q   P   D   S   I   I   E   K   A   S H>
        850        860        870        880        890        900
CTCGGGCATG ATCAACCCCA GCCGGCAGTG GCAGACGCTG AAGCAGAACA CGGGCGTTGC
   S   G   M   I   N   P   S   R   Q   W   Q   T   L   K   Q   N   T   G   V A>
```

FIG. 11A

```
          910        920        930        940        950        960
     CCACTTTGAG TATCAGATCC GCGTGACCTG TGATGACTAC TACTATGGCT TTGGCTGTAA
       H F E    Y Q I      R V T      D D Y      Y Y G      F G C N>
          970        980        990       1000       1010       1020
     TAAGTTCTGC CGCCCCAGAG ATGACTTCTT TGGACACTAT GCCTGTGACC AGAATGGCAA
       K F C    R P R      D D F F    G H Y      A C D      Q N G N>
         1030       1040       1050       1060       1070       1080
     CAAAACTTGC ATGGAAGGCT GGATGGGCCC CGAATGTAAC AGAGCTATTT GCCGACAAGG
       K T C    M E G      W M G P    E C N      R A I      C R Q G>
         1090       1100       1110       1120       1130       1140
     CTGCAGTCCT AAGCATGGGT CTTGCAAACT CCCAGGTGAC TGCAGGTGCC AGTACGGCTG
       C S P    K H G      S C K L    P G D      C R C      Q Y G W>
         1150       1160       1170       1180       1190       1200
     GCAAGGCCTG TACTGTGATA AGTGCATCCC ACACCCGGGA TGCGTCCACG GCATCTGTAA
       Q G L    Y C D      K C I P    H P G      C V H      G I C N>
         1210       1220       1230       1240       1250       1260
     TGAGCCCTGG CAGTGCCTCT GTGAGACCAA CTGGGGCGGC CAGCTCTGTG ACAAAGATCT
       E P W    Q C L      C E T N    W G G      Q L C      D K D L>
         1270       1280       1290       1300       1310       1320
     CAATTACTGT GGGACTCATC AGCCGTGTCT CAACGGGGGA ACTTGTAGCA ACACAGGCCC
       N Y C    G T H      Q P C L    N G G      T C S      N T G P>
         1330       1340       1350       1360       1370       1380
     TGACAAATAT CAGTGTTCCT GCCCTGAGGG GTATTCAGGA CCCAACTGTG AAATTGCTGA
       D K Y    Q C S      C P E G    Y S G      P N C      E I A E>
         1390       1400       1410       1420       1430       1440
     GCACGCCTGC CTCTCTGATC CCTGTCACAA CAGAGGCAGC TGTAAGGAGA CCTCCCTGGG
       H A C    L S D      P C H N    R G S      C K E      T S L G>
         1450       1460       1470       1480       1490       1500
     CTTTGAGTGT GAGTGTTCCC CAGGCTGGAC CGGCCCCACA TGCTCTACAA ACATTGATGA
       F E C    E C S      P G W T    G P T      C S T      N I D D>
         1510       1520       1530       1540       1550       1560
     CTGTTCTCCT AATAACTGTT CCCACGGGGG CACCTGCCAG GACCTGGTTA ACGGATTTAA
       C S P    N N C      S H G G    T C Q      D L V      N G F K>
         1570       1580       1590       1600       1610       1620
     GTGTGTGTGC CCCCCACAGT GGACTGGGAA AACGTGCCAG TTAGATGCAA ATGAATGTGA
       C V C    P P Q      W T G K    T C Q      L D A      N E C E>
         1630       1640       1650       1660       1670       1680
     GGCCAAACCT TGTGTAAACG CCAAATCCTG TAAGAATCTC ATTGCCAGCT ACTACTGCGA
       A K P    C V N      A K S C    K N L      I A S      Y Y C D>
```

FIG. 11B

```
     1690       1700       1710       1720       1730       1740
CTGTCTTCCC GGCTGGATGG GTCAGAATTG TGACATAAAT ATTAATGACT GCCTTGGCCA
 C  L  P    G  W  M    G  Q  N  C  D  I  N  I  N  D    C  L  G  Q>
     1750       1760       1770       1780       1790       1800
GTGTCAGAAT GACGCCTCCT GTCGGGATTT GGTTAATGGT TATCGCTGTA TCTGTCCACC
 C  Q  N    D  A  S    C  R  D  L  V  N  G  Y  R  C    I  C  P  P>
     1810       1820       1830       1840       1850       1860
TGGCTATGCA GGCGATCACT GTGAGAGAGA CATCGATGAA TGTGCCAGCA ACCCCTGTTT
 G  Y  A    G  D  H    C  E  R  D  I  D  E  C  A  S    N  P  C  L>
     1870       1880       1890       1900       1910       1920
GAATGGGGGT CACTGTCAGA ATGAAATCAA CAGATTCCAG TGTCTGTGTC CCACTGGTTT
 N  G  G    H  C  Q    N  E  I  N  R  F  Q  C  L  C    P  T  G  F>
     1930       1940       1950       1960       1970       1980
CTCTGGAAAC CTCTGTCAGC TGGACATCGA TTATTGTGAG CCTAATCCCT GCCAGAACGG
 S  G  N    L  C  Q    L  D  I  D  Y  C  E  P  N  P    C  Q  N  G>
     1990       2000       2010       2020       2030       2040
TGCCCAGTGC TACAACCGTG CCAGTGACTA TTTCTGCAAG TGCCCCGAGG ACTATGAGGG
 A  Q  C    Y  N  R    A  S  D  Y  F  C  K  C  P  E    D  Y  E  G>
     2050       2060       2070       2080       2090       2100
CAAGAACTGC TCACACCTGA AAGACCACTG CCGCACGACC CCCTGTGAAG TGATTGACAG
 K  N  C    S  H  L    K  D  H  C  R  T  T  P  C  E    V  I  D  S>
     2110       2120       2130       2140       2150       2160
CTGCACAGTG GCCATGGCTT CCAACGACAC ACCTGAAGGG GTGCGGTATA TTTCCTCCAA
 C  T  V    A  M  A    S  N  D  T  P  E  G  V  R  Y    I  S  S  N>
     2170       2180       2190       2200       2210       2220
CGTCTGTGGT CCTCACGGGA AGTGCAAGAG TCAGTCGGGA GGCAAATTCA CCTGTGACTG
 V  C  G    P  H  G    K  C  K  S  Q  S  G  G  K  F    T  C  D  C>
     2230       2240       2250       2260       2270       2280
TAACAAAGGC TTCACGGGAA CATACTGCCA TGAAAATATT AATGACTGTG AGAGCAACCC
 N  K  G    F  T  G    T  Y  C  H  E  N  I  N  D  C    E  S  N  P>
     2290       2300       2310       2320       2330       2340
TTGTAGAAAC GGTGGCACTT GCATCGATGG TGTCAACTCC TACAAGTGCA TCTGTAGTGA
 C  R  N    G  G  T    C  I  D  G  V  N  S  Y  K  C    I  C  S  D>
     2350       2360       2370       2380       2390       2400
CGGCTGGGAG GGGGCCTACT GTGAAACCAA TATTAATGAC TGCAGCCAGA ACCCCTGCCA
 G  W  E    G  A  Y    C  E  T  N  I  N  D  C  S  Q    N  P  C  H>
     2410       2420       2430       2440       2450       2460
CAATGGGGGC ACGTGTCGCG ACCTGGTCAA TGACTTCTAC TGTGACTGTA AAAATGGGTG
 N  G  G    T  C  R    D  L  V  N  D  F  Y  C  D  C    K  N  G  W>
```

FIG. 11C

```
            2470       2480       2490       2500       2510       2520
        GAAAGGAAAG ACCTGCCACT CACGTGACAG TCAGTGTGAT GAGGCCACGT GCAACAACGG
          K G K      T C H      S R D S    Q C D      E A T      C N N  G>
            2530       2540       2550       2560       2570       2580
        TGGCACCTGC TATGATGAGG GGGATGCTTT TAAGTGCATG TGTCCTGGCG GCTGGGAAGG
          G T C      Y D E      G D A F    K C M      C P G      G W E  G>
            2590       2600       2610       2620       2630       2640
        AACAACCTGT AACATAGCCC GAAACAGTAG CTGCCTGCCC AACCCCTGCC ATAATGGGGG
          T T C      N I A      R N S S    C L P      N P C      H N G  G>
            2650       2660       2670       2680       2690       2700
        CACATGTGTG GTCAACGGCG AGTCCTTTAC GTGCGTCTGC AAGGAAGGCT GGGAGGGGCC
          T C V      V N G      E S F T    C V C      K E G      W E G  P>
            2710       2720       2730       2740       2750       2760
        CATCTGTGCT CAGAATACCA ATGACTGCAG CCCTCATCCC TGTTACAACA GCGGCACCTG
          I C A      Q N T      N D C S    P H P      C Y N      S G T  C>
            2770       2780       2790       2800       2810       2820
        TGTGGATGGA GACAACTGGT ACCGGTGCGA ATGTGCCCCG GGTTTTGCTG GGCCCGACTG
          V D G      D N W      Y R C E    C A P      G F A      G P D  C>
            2830       2840       2850       2860       2870       2880
        CAGAATAAAC ATCAATGAAT GCCAGTCTTC ACCTTGTGCC TTTGGAGCGA CCTGTGTGGA
          R I N      I N E      C Q S S    P C A      F G A      T C V  D>
            2890       2900       2910       2920       2930       2940
        TGAGATCAAT GGCTACCGGT GTGTCTGCCC TCCAGGGCAC AGTGGTGCCA AGTGCCAGGA
          E I N      G Y R      C V C P    P G H      S G A      K C Q  E>
            2950       2960       2970       2980       2990       3000
        AGTTTCAGGG AGACCTTGCA TCACCATGGG GAGTGTGATA CCAGATGGGG CCAAATGGGA
          V S G      R P C      I T M G    S V I      P D G      A K W  D>
            3010       3020       3030       3040       3050       3060
        TGATGACTGT AATACCTGCC AGTGCCTGAA TGGACGGATC GCCTGCTCAA AGGTCTGGTG
          D D C      N T C      Q C L N    G R I      A C S      K V W  C>
            3070       3080       3090       3100       3110       3120
        TGGCCCTCGA CCTTGCCTGC TCCACAAAGG GCACAGCGAG TGCCCCAGCG GGCAGAGCTG
          G P R      P C L      L H K G    H S E      C P S      G Q S  C>
            3130       3140       3150       3160       3170       3180
        CATCCCCATC CTGGACGACC AGTGCTTCGT CCACCCCTGC ACTGGTGTGG GCGAGTGTCG
          I P I      L D D      Q C F V    H P C      T G V      G E C  R>
            3190       3200       3210       3220       3230       3240
        GTCTTCCAGT CTCCAGCCGG TGAAGACAAA GTGCACCTCT GACTCCTATT ACCAGGATAA
          S S S      L Q P      V K T K    C T S      D S Y      Y Q D  N>
            3250       3260       3270       3280       3290       3300
        CTGTGCGAAC ATCACATTTA CCTTTAACAA GGAGATGATG TCACCAGGTC TTACTACGGA
          C A N      I T F      T F N K    E M M      S P G      L T T  E>
```

FIG. 11D

```
       3310       3320       3330       3340       3350       3360
 GCACATTTGC AGTGAATTGA GGAATTTGAA TATTTTGAAG AATGTTTCCG CTGAATATTC
   H  I  C   S  E  L    R  N  L    N  I  L  K   N  V  S   A  E  Y  S>
       3370       3380       3390       3400       3410       3420
 AATCTACATC GCTTGCGAGC CTTCCCCTTC AGCGAACAAT GAAATACATG TGGCCATTTC
   I  Y  I   A  C  E    P  S  P  S   A  N  N   E  I  H   V  A  I  S>
       3430       3440       3450       3460       3470       3480
 TGCTGAAGAT ATACGGGATG ATGGGAACCC GATCAAGGAA ATCACTGACA AAATAATCGA
   A  E  D   I  R  D   D  G  N  P   I  K  E   I  T  D    K  I  I  D>
       3490       3500       3510       3520       3530       3540
 TCTTGTTACT AAACGTGATG GAAACAGCTC GCTGATTGCT GCCGTTGAAG AAGTAAGAGT
   L  V  T    K  R  D   G  N  S  S   L  I  A   A  V  E    E  V  R  V>
       3550       3560       3570       3580       3590       3600
 TCAGAGGCGG CCTCTGAAGA ACAGAACAGA TTTCCTTGTT CCCTTGCTGA GCTCTGTCTT
   Q  R  R   P  L  K   N  R  T  D   F  L  V    P  L  L    S  S  V  L>
       3610       3620       3630       3640       3650       3660
 AACTGTGGCT TGGATCTGTT GCTTGGTGAC GGCCTTCTAC TGGTGCCTGC GGAAGCGGCG
   T  V  A   W  I  C    C  L  V  T   A  F  Y   W  C  L   R  K  R  R>
       3670       3680       3690       3700       3710       3720
 GAAGCCGGGC AGCCACACAC ACTCAGCCTC TGAGGACAAC ACCACCAACA ACGTGCGGGA
   K  P  G   S  H  T    H  S  A  S   E  D  N   T  T  N   N  V  R  E>
       3730       3740       3750       3760       3770       3780
 GCAGCTGAAC CAGATCAAAA ACCCCATTGA GAAACATGGG GCCAACACGG TCCCCATCAA
   Q  L  N   Q  I  K    N  P  I   E   K  H  G  A  N  T   V  P  I  K>
       3790       3800       3810       3820       3830       3840
 GGATTACGAG AACAAGAACT CCAAAATGTC TAAAATAAGG ACACACAATT CTGAAGTAGA
   D  Y  E   N  K  N    S  K  M  S   K  I  R   T  H  N    S  E  V  E>
       3850       3860       3870       3880       3890       3900
 AGAGGACGAC ATGGACAAAC ACCAGCAGAA AGCCCGGTTT GCCAAGCAGC CGGCGTACAC
   E  D  D   M  D  K    H  Q  Q  K   A  R  F   A  K  Q   P  A  Y  T>
       3910       3920       3930       3940       3950       3960
 GCTGGTAGAC AGAGAAGAGA AGCCCCCCAA CGGCACGCCG ACAAAACACC CAAACTGGAC
   L  V  D   R  E  E    K  P  P  N   G  T  P    T  K  H   P  N  W  T>
       3970       3980       3990       4000       4010       4020
 AAACAAACAG GACAACAGAG ACTTGGAAAG TGCCCAGAGC TTAAACCGAA TGGAGTACAT
   N  K  Q   D  N  R   D  L  E  S   A  Q  S    L  N  R   M  E  Y  I>
       4030       4040       4050       4060       4070       4080
 CGTATAGCAG ACCGCGGGCA CTGCCGCCGC TAGGTAGAGT CTGAGGGCTT GTAGTTCTTT
   V   >
```

FIG. 11E

```
      4090       4100       4110       4120       4130       4140
AAACTGTCGT GTCATACTCG AGTCTGAGGC CGTTGCTGAC TTAGAATCCC TGTGTTAATT
      4150       4160       4170       4180       4190       4200
TAGTTTGACA AGCTGGCTTA CACTGGCAAT GGTAGTTCTG TGGTTGGCTG GGAAATCGAG
      4210       4220       4230       4240       4250       4260
TGGCGCATCT CACAGCTATG CAAAAAGCTA GTCAACAGTA CCCCTGGTTG TGTGTCCCCT
      4270       4280       4290       4300       4310       4320
TGCAGCCGAC ACGGTCTCGG ATCAGGCTCC CAGGAGCTGC CCAGCCCCCT GGTACTTTGA
      4330       4340       4350       4360       4370       4380
GCTCCCACTT CTGCCAGATG TCTAATGGTG ATGCAGTCTT AGATCATAGT TTTATTTATA
      4390       4400       4410       4420       4430       4440
TTTATTGACT CTTGAGTTGT TTTTGTATAT TGGTTTTATG ATGACGTACA AGTAGTTCTG
      4450       4460       4470       4480       4490       4500
TATTTGAAAG TGCCTTTGCA GCTCAGAACC ACAGCAACGA TCACAAATGA CTTTATTATT
      4510       4520       4530       4540       4550       4560
TATTTTTTTT AATTGTATTT TTGTTGTTGG GGGAGGGGAG ACTTTGATGT CAGCAGTTGC
      4570       4580       4590       4600       4610       4620
TGGTAAAATG AAGAATTTAA AGAAAAAATG TCCAAAAGTA GAACTTTGTA TAGTTATGTA
      4630       4640       4650       4660       4670       4680
AATAATTCTT TTTTATTAAT CACTGTGTAT ATTTGATTTA TTAACTTAAT AATCAAGAGC
      4690       4700       4710       4720       4730       4740
CTTAAAACAT CATTCCTTTT TATTTATATG TATGTGTTTA GAATTGAAGG TTTTTGATAG
      4750       4760       4770       4780       4790       4800
CATTGTAAGC GTATGGCTTT ATTTTTTTGA ACTCTTCTCA TTACTTGTTG CCTATAAGCC
      4810       4820       4830       4840       4850       4860
AAAAAGGAAA GGGTGTTTTG AAAATAGTTT ATTTTAAAAC AATAGGATGG GCTACACGTA
      4870       4880       4890       4900       4910       4920
CATAGGTAAA TAATAGCACC GTACTGGTTA TGATGATGAA AATAACTGGA AACTTGAAAG
      4930       4940       4950       4960       4970       4980
CTTGTGGTAA TGGCAGATAA AGATGGTTCA CCTGGGAAAT TAAAACTTGA ATGGTTGTAC
      4990       5000       5010       5020       5030       5040
AGAAAAGCAC AGAGTGGAAT GCACATCAAT GACAGTAAGG GAGTTAGTTC TAGGAACAGC
      5050       5060       5070       5080       5090       5100
TCCTGAACAG TAAGATTCCC GCAATAGTCT CCGCCTCGTT CGTCTATGGT ATGCATCCCA
      5110       5120       5130       5140       5150       5160
TTCATTTTCT TCTTCTGATT ATTGTCATCT TTCCCTTTGC CAAATGGGCA GTTATTGTTT
      5170       5180       5190       5200       5210       5220
CAGGGAGAGA AGCTGCTCAT TGGCCAATCA TTCTGGTGTG CAGTGCTCCA TCGGATTCTA
      5230       5240       5250       5260       5270       5280
CATGTCCAAC AAGGCATGTC TGGATGATGC AATGTCTGTC TGACCCCCGG AATTCCGTGC
```

FIG. 11F

```
      5290       5300       5310       5320       5330       5340
AGAGACAACA TTCTAGACAG ATATACACTT TTTATTATTA ACAAACTTTG GCCACAACCT
      5350       5360       5370       5380       5390       5400
TTGATGTATA AATTGCCGGA TTTCCCCAGT CCTTTCATTG TGGCTTTGGA CAGGAGCAGG
      5410       5420       5430       5440       5450       5460
CTCACTTGTC TGCTTCAGGC TGCCTTTCTC TTGGGTTGCA CCTCAGTTCT TACTTATTTA
      5470       5480       5490       5500       5510       5520
TTTATTTTGA GTGGAGCATA GGGGCCTCTT CCAAAATGGG TAGAGCTCAG GGGCTTTCTT
      5530       5540       5550       5560       5570       5580
ATTGAAATGG TCACATGATA AAAACGGGCT GAAAAAGGAG AGTTCCAGGA GAAAAGCCCA
      5590       5600       5610       5620       5630       5640
GAAAAGGCCC CTCCTCAGAA GACAGCCTTT AAGCCTCTTG CTTACTGAAG GAAGCCCCAC
      5650       5660       5670       5680       5690       5700
CTTCTAGCAC TGAGGCCGGG TCTGATCTTC CAGAGGAGTT GGAGGAGTCC ATGAGAATGG
      5710       5720       5730       5740       5750       5760
CCACCATTCT TGCTTGCTGC TGCTGATGTT GCAGTTTTGA GAGAACAGCG GGATCCTTGT
      5770       5780       5790       5800       5810       5820
TGTCCTCTAG AGACTTGAGT CTGTCACTGA CATTTTTTCA GTTCCTTTGC TCATAGACCA
      5830       5840       5850       5860       5870       5880
TACGAGGAAT TAGTGATGTG TCAGTTGAGA GTTCACAATC TCATTGTTCA TTTAATTCAC
      5890       5900       5910       5920       5930       5940
TTTAAAGTTG TCAATTTCTG TGTGAGTAAC CTGTAAAAGA CACCTTTCCA GAAGAGTTTT
      5950       5960       5970       5980       5990       6000
GCCGTCTGTT TGAAAAAAAA ATCTTTATAA ACTTTCCTAA GTATCTGGAT TTGGATTCCT
      6010       6020       6030       6040       6050       6060
TATTTGGAGA GAAAATGTAC CCTGTCTCCA CCAAAAATAC AAAAATTAGC CAGGCTTGGT
      6070       6080       6090       6100       6110       6120
GGTGCACACC GGTAATCCCA GCAACTCTGG AGACTAAGGC AGGAAGAATC GCTTGACCCA
      6130       6140       6150       6160       6170       6180
GGAGGGTCGA GGCTACAATG AGTTGAAACC GCGCCACTGC ACTCCAGCCT GGGCGACAGT
      6190       6200       6210       6220       6230       6240
GCGAGGCCCT GTCTCAAAAA TAAAATAAAA TAAATAAATA AATTAGCCAG ATACTGTGTG
      6250       6260       6270       6280       6290       6300
CACGCCTGCA GTCCCAGCTA TTCTGGAAGC TGAGGTGGGA AGATGGTTAA GCCTGAGAGG
      6310       6320       6330       6340       6350       6360
ACAAAGCTGC AGTGAGTCAT GTTTGCATCA CTGCACTCCA GCCTGGGTGA CAGAGCAAGA
      6370       6380       6390       6400       6410       6420
CCCTGTCTAA AAAACAAAAA CAGGCCGGGT GTGGTGGCTC ATGCCTGCCA TCCCAGTGCT
      6430       6440       6450       6460
TTGGGAGGCA GAGGTTGGCA TAATCCCAGC GCTCTGGGAA TTCC
```

FIG. 11G

```
GGCCGGGGCC GGGCGGGCGG GTCGCGGGGG CAATGCGGGC GCAGGGCCGG GGGCGCCTTC   60

CCCGGCGGCT GCTGCTGCTG CTGGCGCTCT GGGTGCAGGC GGCGCGGCCC ATGGGCTATT  120

TCGAGCTGCA GCTGAGCGCG CTGCGGAACG TGAACGGGGA GCTGCTGAGC GGCGCCTGCT  180

GTGACGGCGA CGGCCGGACA ACGCGCGCGG GGGGCTGCGG CCACGACGAG TGCGACACCG  240

CTCCTTTACC CTCATCGTGG AGGCCTGGGA CTGGGACAAC GATACCACCC CGAATGAGGA  300

GCTGCTGATC GAGCGAGTGT CGCATGCCGG C ATG ATC AAC CCG GAG GAC CGC      352
                                  Met Ile Asn Pro Glu Asp Arg
                                   1                   5
TGG AAG AGC CTG CAC TTC AGC GGC CAC GTG GCG CAC CTG GAG CTG CAG    400
Trp Lys Ser Leu His Phe Ser Gly His Val Ala His Leu Glu Leu Gln
         10                  15                  20
ATC CGC GTG CGC TGC GAC GAG AAC TAC TAC AGC GCC ACT TGC AAC AAG    448
Ile Arg Val Arg Cys Asp Glu Asn Tyr Tyr Ser Ala Thr Cys Asn Lys
     25                  30                  35
TTC TGC CGG CCC CGC AAT GAC TTT TTC GGC CAC TAC ACC TGC GAC CAG    496
Phe Cys Arg Pro Arg Asn Asp Phe Phe Gly His Tyr Thr Cys Asp Gln
 40                  45                  50                  55
TAC GGC AAC AAG GCC TGC ATG GAC GGC TGG ATG GGC AAG GAG TGC AAG    544
Tyr Gly Asn Lys Ala Cys Met Asp Gly Trp Met Gly Lys Glu Cys Lys
                 60                  65                  70
GAA GCT GTG TGT AAA CAA GGG TGT AAT TTG CTC CAC GGG GGA TGC ACC    592
Glu Ala Val Cys Lys Gln Gly Cys Asn Leu Leu His Gly Gly Cys Thr
             75                  80                  85
GTG CCT GGG GAG TGC AGG TGC AGC TAC GGC TGG CAA GGG AGG TTC TGC    640
Val Pro Gly Glu Cys Arg Cys Ser Tyr Gly Trp Gln Gly Arg Phe Cys
         90                  95                 100
GAT GAG TGT GTC CCC TAC CCC GGC TGC GTG CAT GGC AGT TGT GTG GAG    688
Asp Glu Cys Val Pro Tyr Pro Gly Cys Val His Gly Ser Cys Val Glu
    105                 110                 115
CCC TGG CAG TGC AAC TGT GAG ACC AAC TGG GGC GGC CTG CTC TGT GAC    736
Pro Trp Gln Cys Asn Cys Glu Thr Asn Trp Gly Gly Leu Leu Cys Asp
120                 125                 130                 135
AAA GAC CTG AAC TAC TGT GGC AGC CAC CAC CCC TGC ACC AAC GGA GGC    784
Lys Asp Leu Asn Tyr Cys Gly Ser His His Pro Cys Thr Asn Gly Gly
                140                 145                 150
```

FIG. 12A

```
ACG TGC ATC AAC GCC GAG CCT GAC CAG TAC CGC TGC ACC TGC CCT GAC  832
Thr Cys Ile Asn Ala Glu Pro Asp Gln Tyr Arg Cys Thr Cys Pro Asp
            155                 160                 165
GGC TAC TCG GGC AGG AAC TGT GAG AAG GCT GAG CAC GCC TGC ACC TCC  880
Gly Tyr Ser Gly Arg Asn Cys Glu Lys Ala Glu His Ala Cys Thr Ser
            170                 175                 180
AAC CCG TGT GCC AAC GGG GGC TCT TGC CAT GAG GTG CCG TCC GGC TTC  928
Asn Pro Cys Ala Asn Gly Gly Ser Cys His Glu Val Pro Ser Gly Phe
        185                 190                 195
GAA TGC CAC TGC CCA TCG GGC TGG AGC GGG CCC ACC TGT GCC CTT GAC  976
Glu Cys His Cys Pro Ser Gly Trp Ser Gly Pro Thr Cys Ala Leu Asp
200                 205                 210                 215
ATC GAT GAG TGT GCT TCG AAC CCG TGT GCG GCC GGT GGC ACC TGT GTG 1024
Ile Asp Glu Cys Ala Ser Asn Pro Cys Ala Ala Gly Gly Thr Cys Val
                220                 225                 230
GAC CAG GTG GAC GGC TTT GAG TGC ATC TGC CCC GAG CAG TGG GTG GGG 1072
Asp Gln Val Asp Gly Phe Glu Cys Ile Cys Pro Glu Gln Trp Val Gly
            235                 240                 245
GCC ACC TGC CAG CTG GAC GCC AAT GAG TGT GAA GGG AAG CCA TGC CTT 1120
Ala Thr Cys Gln Leu Asp Ala Asn Glu Cys Glu Gly Lys Pro Cys Leu
        250                 255                 260
AAC GCT TTT TCT TGC AAA AAC CTG ATT GGC GGC TAT TAC TGT GAT TGC 1168
Asn Ala Phe Ser Cys Lys Asn Leu Ile Gly Gly Tyr Tyr Cys Asp Cys
    265                 270                 275
ATC CCG GGC TGG AAG GGC ATC AAC TGC CAT ATC AAC GTC AAC GAC TGT 1216
Ile Pro Gly Trp Lys Gly Ile Asn Cys His Ile Asn Val Asn Asp Cys
280                 285                 290                 295
CGC GGG CAG TGT CAG CAT GGG GGC ACC TGC AAG GAC CTG GTG AAC GGG 1264
Arg Gly Gln Cys Gln His Gly Gly Thr Cys Lys Asp Leu Val Asn Gly
                300                 305                 310
TAC CAG TGT GTG TGC CCA CGG GGC TTC GGA GGC CGG CAT TGC GAG CTG 1312
Tyr Gln Cys Val Cys Pro Arg Gly Phe Gly Gly Arg His Cys Glu Leu
            315                 320                 325
GAA CGA GAC AAG TGT GCC AGC AGC CCC TGC CAC AGC GGC GGC CTC TGC 1360
Glu Arg Asp Lys Cys Ala Ser Ser Pro Cys His Ser Gly Gly Leu Cys
        330                 335                 340
GAG GAC CTG GCC GAC GGC TTC CAC TGC CAC TGC CCC CAG GGC TTC TCC 1408
Glu Asp Leu Ala Asp Gly Phe His Cys His Cys Pro Gln Gly Phe Ser
    345                 350                 355
```

FIG. 12B

```
GGG CCT CTC TGT GAG GTG GAT GTC GAC CTT TGT GAG CCA AGC CCC TGC   1456
Gly Pro Leu Cys Glu Val Asp Val Asp Leu Cys Glu Pro Ser Pro Cys
360             365             370             375
CGG AAC GGC GCT CGC TGC TAT AAC CTG GAG GGT GAC TAT TAC TGC GCC   1504
Arg Asn Gly Ala Arg Cys Tyr Asn Leu Glu Gly Asp Tyr Tyr Cys Ala
            380             385             390
TGC CCT GAT GAC TTT GGT GGC AAG AAC TGC TCC GTG CCC CGC GAG CCG   1552
Cys Pro Asp Asp Phe Gly Gly Lys Asn Cys Ser Val Pro Arg Glu Pro
                395             400             405
TGC CCT GGC GGG GCC TGC AGA GTG ATC GAT GGC TGC GGG TCA GAC GCG   1600
Cys Pro Gly Gly Ala Cys Arg Val Ile Asp Gly Cys Gly Ser Asp Ala
        410             415             420
GGG CCT GGG ATG CCT GGC ACA GCA GCC TCC GGC GTG TGT GGC CCC CAT   1648
Gly Pro Gly Met Pro Gly Thr Ala Ala Ser Gly Val Cys Gly Pro His
    425             430             435
GGA CGC TGC GTC AGC CAG CCA GGG GGC AAC TTT TCC TGC ATC TGT GAC   1696
Gly Arg Cys Val Ser Gln Pro Gly Gly Asn Phe Ser Cys Ile Cys Asp
440             445             450             455
AGT GGC TTT ACT GGC ACC TAC TGC CAT GAG AAC ATT GAC GAC TGC CTG   1744
Ser Gly Phe Thr Gly Thr Tyr Cys His Glu Asn Ile Asp Asp Cys Leu
        460             465             470
GGC CAG CCC TGC CGC AAT GGG GGC ACA TGC ATC GAT GAG GTG GAC GCC   1792
Gly Gln Pro Cys Arg Asn Gly Gly Thr Cys Ile Asp Glu Val Asp Ala
    475             480             485
TTC CGC TGC TTC TGC CCC AGC GGT TGG GAG GGC GAG CTC TGC GAC ACC   1840
Phe Arg Cys Phe Cys Pro Ser Gly Trp Glu Gly Glu Leu Cys Asp Thr
        490             495             500
AAT CCC AAC GAC TGC CTT CCC GAT CCC TGC CAC AGC CGC GGC CGC TGC   1888
Asn Pro Asn Asp Cys Leu Pro Asp Pro Cys His Ser Arg Gly Arg Cys
    505             510             515
TAC GAC CTG GTC AAT GAC TTC TAC TGT GCG TGC GAC GAC GGC TGG AAG   1936
Tyr Asp Leu Val Asn Asp Phe Tyr Cys Ala Cys Asp Asp Gly Trp Lys
520             525             530             535
GGC AAG ACC TGC CAC TCA CGC GAG TTC CAG TGC GAT GCC TAC ACC TGC   1984
Gly Lys Thr Cys His Ser Arg Glu Phe Gln Cys Asp Ala Tyr Thr Cys
                540             545             550
AGC AAC GGT GGC ACC TGC TAC GAC AGC GGC GAC ACC TTC CGC TGC GCC   2032
Ser Asn Gly Gly Thr Cys Tyr Asp Ser Gly Asp Thr Phe Arg Cys Ala
            555             560             565
TGC CCC CCC GGC TGG AAG GGC AGC ACC TGC GCC GTC GCC AAG AAC AGC   2080
Cys Pro Pro Gly Trp Lys Gly Ser Thr Cys Ala Val Ala Lys Asn Ser
        570             575             580
```

FIG. 12C

```
AGC TGC CTG CCC AAC CCC TGT GTG AAT GGT GGC ACC TGC GTG GGC AGC    2128
Ser Cys Leu Pro Asn Pro Cys Val Asn Gly Gly Thr Cys Val Gly Ser
    585                 590                 595
GGG GCC TCC TTC TCC TGC ATC TGC CGG GAC GGC TGG GAG GGT CGT ACT    2176
Gly Ala Ser Phe Ser Cys Ile Cys Arg Asp Gly Trp Glu Gly Arg Thr
600                 605                 610                 615
TGC ACT CAC AAT ACC AAC GAC TGC AAC CCT CTG CCT TGC TAC AAT GGT    2224
Cys Thr His Asn Thr Asn Asp Cys Asn Pro Leu Pro Cys Tyr Asn Gly
            620                 625                 630
GGC ATC TGT GTT GAC GGC GTC AAC TGG TTC CGC TGC GAG TGT GCA CCT    2272
Gly Ile Cys Val Asp Gly Val Asn Trp Phe Arg Cys Glu Cys Ala Pro
                635                 640                 645
GGC TTC GCG GGG CCT GAC TGC CGC ATC AAC ATC GAC GAG TGC CAG TCC    2320
Gly Phe Ala Gly Pro Asp Cys Arg Ile Asn Ile Asp Glu Cys Gln Ser
                    650                 655                 660
TCG CCC TGT GCC TAC GGG GCC ACG TGT GTG GAT GAG ATC AAC GGG TAT    2368
Ser Pro Cys Ala Tyr Gly Ala Thr Cys Val Asp Glu Ile Asn Gly Tyr
665                 670                 675
CGC TGT AGC TGC CCA CCC GGC CGA GCC GGC CCC CGG TGC CAG GAA GTG    2416
Arg Cys Ser Cys Pro Pro Gly Arg Ala Gly Pro Arg Cys Gln Glu Val
680                 685                 690                 695
ATC GGG TTC GGG AGA TCC TGC TGG TCC CGG GGC ACT CCG TTC CCA CAC    2464
Ile Gly Phe Gly Arg Ser Cys Trp Ser Arg Gly Thr Pro Phe Pro His
                700                 705                 710
GGA AGC TCC TGG GTG GAA GAC TGC AAC AGC TGC CGC TGC CTG GAT GGC    2512
Gly Ser Ser Trp Val Glu Asp Cys Asn Ser Cys Arg Cys Leu Asp Gly
            715                 720                 725
CGC CGT GAC TGC AGC AAG GTG TGG TGC GGA TGG AAG CCT TGT CTG CTG    2560
Arg Arg Asp Cys Ser Lys Val Trp Cys Gly Trp Lys Pro Cys Leu Leu
                730                 735                 740
GCC GGC CAG CCC GAG GCC CTG AGC GCC CAG TGC CCA CTG GGG CAA AGG    2608
Ala Gly Gln Pro Glu Ala Leu Ser Ala Gln Cys Pro Leu Gly Gln Arg
                    745                 750                 755
TGC CTG GAG AAG GCC CCA GGC CAG TGT CTG CGA CCA CCC TGT GAG GCC    2656
Cys Leu Glu Lys Ala Pro Gly Gln Cys Leu Arg Pro Pro Cys Glu Ala
760                 765                 770                 775
TGG GGG GAG TGC GGC GCA GAA GAG CCA CCG AGC ACC CCC TGC CTG CCA    2704
Trp Gly Glu Cys Gly Ala Glu Glu Pro Pro Ser Thr Pro Cys Leu Pro
                780                 785                 790
CGC TCC GGC CAC CTG GAC AAT AAC TGT GCC CGC CTC ACC TTG CAT TTC    2752
Arg Ser Gly His Leu Asp Asn Asn Cys Ala Arg Leu Thr Leu His Phe
            795                 800                 805
```

FIG. 12D

```
AAC CGT GAC CAC GTG CCC CAG GGC ACC ACG GTG GGC GCC ATT TGC TCC   2800
Asn Arg Asp His Val Pro Gln Gly Thr Thr Val Gly Ala Ile Cys Ser
            810                 815                 820
GGG ATC CGC TCC CTG CCA GCC ACA AGG GCT GTG GCA CGG GAC CGC CTG   2848
Gly Ile Arg Ser Leu Pro Ala Thr Arg Ala Val Ala Arg Asp Arg Leu
        825                 830                 835
CTG GTG TTG CTT TGC GAC CGG GCG TCC TCG GGG GCC AGT GCT GTG GAG   2896
Leu Val Leu Leu Cys Asp Arg Ala Ser Ser Gly Ala Ser Ala Val Glu
840                 845                 850                 855
GTG GCC GTG TCC TTC AGC CCT GCC AGG GAC CTG CCT GAC AGC AGC CTG   2944
Val Ala Val Ser Phe Ser Pro Ala Arg Asp Leu Pro Asp Ser Ser Leu
                860                 865                 870
ATC CAG GGC GCG GCC CAC GCC ATC GTG GCC GCC ATC ACC CAG CGG GGG   2992
Ile Gln Gly Ala Ala His Ala Ile Val Ala Ala Ile Thr Gln Arg Gly
            875                 880                 885
AAC AGC TCA CTG CTC CTG GCT GTC ACC GAG GTC AAG GTG GAG ACG GTT   3040
Asn Ser Ser Leu Leu Leu Ala Val Thr Glu Val Lys Val Glu Thr Val
        890                 895                 900
GTT ACG GGC GGC TCT TCC ACA GGT CTG CTG GTG CCT GTG CTG TGT GGT   3088
Val Thr Gly Gly Ser Ser Thr Gly Leu Leu Val Pro Val Leu Cys Gly
    905                 910                 915
GCC TTC AGC GTG CTG TGG CTG GCG TGC GTG GTC CTG TGC GTG TGG TGG   3136
Ala Phe Ser Val Leu Trp Leu Ala Cys Val Val Leu Cys Val Trp Trp
920                 925                 930                 935
ACA CGC AAG CGC AGG AAA GAG CGG GAG AGG AGC CGG CTG CCG CGG GAG   3184
Thr Arg Lys Arg Arg Lys Glu Arg Glu Arg Ser Arg Leu Pro Arg Glu
                940                 945                 950
GAG AGC GCC AAC AAC CAG TGG GCC CCG CTC AAC CCC ATC CGC AAC CCC   3232
Glu Ser Ala Asn Asn Gln Trp Ala Pro Leu Asn Pro Ile Arg Asn Pro
            955                 960                 965
ATT GAG CGG CCG GGG GGG CAC AAG GAC GTG CTC TAC CAG TGC AAG AAC   3280
Ile Glu Arg Pro Gly Gly His Lys Asp Val Leu Tyr Gln Cys Lys Asn
        970                 975                 980
TTC ACT CCA CCG CCG CGC AGG CGC TGC CCG GGC CGG CCG GCC ACG CGG   3328
Phe Thr Pro Pro Pro Arg Arg Arg Cys Pro Gly Arg Pro Ala Thr Arg
    985                 990                 995
CCG TCA GGG AGG ATG AGG AGG ACG AGG ATC TTG GCC GCG GTG AGG AGG   3376
Pro Ser Gly Arg Met Arg Arg Thr Arg Ile Leu Ala Ala Val Arg Arg
1000                1005                1010                1015
ACT CCC TGG AGG CGG AGA AGT TCC TCT CAC ACA AAT TCA CCA AAG ATC   3424
Thr Pro Trp Arg Arg Arg Ser Ser Ser His Thr Asn Ser Pro Lys Ile
                1020                1025                1030
```

FIG. 12E

```
CTG GCC GCT CGC CGG GGA GGC CGG CCC ACT GGG CCT CAG GCC CCA AAG   3472
Leu Ala Ala Arg Arg Gly Gly Arg Pro Thr Gly Pro Gln Ala Pro Lys
            1035            1040            1045
TGG ACA ACC GCG CGG TCA GGA GCA TCA ATG AGG CCC GCT ACG TCG GCA   3520
Trp Thr Thr Ala Arg Ser Gly Ala Ser Met Arg Pro Ala Thr Ser Ala
            1050            1055            1060
AGG GAA GTA GGG CGG CTG CAG CTG GGC CGG GAC CCA GGG CCC TCG GTG   3568
Arg Glu Val Gly Arg Leu Gln Leu Gly Arg Asp Pro Gly Pro Ser Val
            1065            1070            1075
GGA GCC ATG CCG TCT GCC GGA CCC GGA GGC CGA GGC CAT GTG CAT AGT   3616
Gly Ala Met Pro Ser Ala Gly Pro Gly Gly Arg Gly His Val His Ser
1080            1085            1090            1095
TTC TTT ATT TTG TGT AAA AAA ACC ACC AAA AAC AAA AAC CAA ATG TTT   3664
Phe Phe Ile Leu Cys Lys Lys Thr Thr Lys Asn Lys Asn Gln Met Phe
            1100            1105            1110
ATT TTC TAC GTT TCT TTA ACC TTG TAT AAA TTA TTC AGT AAC TGT CAG   3712
Ile Phe Tyr Val Ser Leu Thr Leu Tyr Lys Leu Phe Ser Asn Cys Gln
            1115            1120            1125
GCT GAA AAC AAT GGA GTA TTC TCG GAT AGT TGC TAT TTT TGT AAA GTA   3760
Ala Glu Asn Asn Gly Val Phe Ser Asp Ser Cys Tyr Phe Cys Lys Val
           ·1130            1135·           1140
GCC GTG CGT GGC ACT CGC TGT ATG AAA GGA GAG AGC AAA GGG TGT CTG   3808
Ala Val Arg Gly Thr Arg Cys Met Lys Gly Glu Ser Lys Gly Cys Leu
            1145            1150            1155
CGT CGT CAC CAA ATC GTC GCG TTT GTT ACC AGA GGT TGT GCA CTG TTT   3856
Arg Arg His Gln Ile Val Ala Phe Val Thr Arg Gly Cys Ala Leu Phe
1160            1165            1170            1175
ACA GAA TCT TCC TTT TAT TCC TCA CTC GGG TTT CTC TGT GCT CCA GGC   3904
Thr Glu Ser Ser Phe Tyr Ser Ser Leu Gly Phe Leu Cys Ala Pro Gly
            1180            1185            1190
CAA AGT GCC GGT GAG ACC CAT GGC TGT GTT GGT GTG GCC CAT GGC TGT   3952
Gln Ser Ala Gly Glu Thr His Gly Cys Val Gly Val Ala His Gly Cys
            1195            1200            1205
TGG TGG GAC CCG TGG CTG ATG GTG TGG CCT GTG GCT GTC GGT GGG ACT   4000
Trp Trp Asp Pro Trp Leu Met Val Trp Pro Val Ala Val Gly Gly Thr
            1210            1215            1220
CGT GGC TGT CAA TGG GAC CTG TGG CTG TCG GTG GGA CCT ACG GTG GTC   4048
Arg Gly Cys Gln Trp Asp Leu Trp Leu Ser Val Gly Pro Thr Val Val
            1225            1230            1235
```

FIG. 12F

```
GGT GGG ACC CTG GTT ATT GAT GTG GCC CTG GCT GCC GGC ACG GCC CGT    4096
Gly Gly Thr Leu Val Ile Asp Val Ala Leu Ala Ala Gly Thr Ala Arg
1240            1245            1250            1255
GGC TGT TG ACGCACCTGT GGTTGTTAGT GGGGCCTGAG GTCATCGGCG TGGCCCAAGG   4154
Gly Cys
CCGGCAGGTC AACCTCGCGC TTGCTGGCCA GTCCACCCTG CCTGCCGTCT GTGCTTCCTC   4214

CTGCCCAGAA CGCCCGCTCC AGCGATCTCT CCACTGTGCT TTCAGAAGTG CCCTTCCTGC   4274

TGCGCAGTTC TCCCATCCTG GGACGGCGGC AGTATTGAAG CTCGTGACAA GTGCCTTCAC   4334

ACAGACCCCT CGCAACTGTC CACGCGTGCC GTGGCACCAG GCGCTGCCCA CCTGCCGGCC   4394

CCGGCCGCCC CTCCTCGTGA AAGTGCATTT TTGTAAATGT GTACATATTA AAGGAAGCAC   4454

TCTGTATAAA AAAAAAAAAC CGGAATTCC                                     4483
```

FIG. 12G

```
CAGGTGGCGTCAGCATCGGGACAGTTCGAGCTGGAGATCTTATCCGTGCAGAATGTGAACGGCGTGCT
GCAGAACGGGAACTGCTGCGACGGCACTCGAAACCCCGGAGATAAAAAGTGCACCAGAGATGAGTGTG
ACACCTACTTTAAAGTTTGCCTGAAGGAGTACCAGTCGCGGGTCACTGCTGGCGGCCCTTGCAGCTTC
GGATCCAAATCCACCCCTGTCATCGGCGGGAATACCTTCAATTTAAAGTACAGCCGGAATAATGAAAA
GAACCGGATTGTTATCCCTTTCACGTTCGCCTGGCCGAGATCCTACACGTTGCTTGTTGAGGCATGGG
ATTACAATGATAACTCTACTAATCCCGATCGCATAATTGAGAAGGCATCCCACTCTGGCATGATCAAT
CCAAGCCGTCAGTGGCAGACGTTGAAACATAACACAGGAGCTGCCCACTTTGAGTATCAAATCCGTGT
GACTTGCGCAGAACATTACTATGGCTTTGGATGCAACAAGTTTTGTCGACCGAGAGATGACTTCTTCA
CTCACCATACCTGTGACCAGAATGGCAACAAAACCTGCTTGGAAGGCTGGACGGGACCAGAATGCAAC
AAAGCTATTTGTCGTCAGGGATGTAGCCCCAAGCATGGTTCTTGCACAGTTCCAGGAGAGTGCAGGTG
TCAGTATGGATGGCAAGGCCAGTACTGTGATAAGTGCATTCCACACCCGGGATGTGTCCATGGCACTT
GCATTGAACCATGGCAGTGCCTCTGTGAAACCAACTGGGGTGGTCAGCTCTGTGACAAAGACCTGAAC
TACTGTGGAACCCACCCACCCTGTTTGAATGGTGGTACCTGCAGCAACACTGGCCCCGATAAATACCA
GTGTTCCTGCCCTGAGGGTTACTCAGGACAGAACTGTGAAATAGCGGAGCATGCGTGCCTCTCTGATC
CGTGCCACAACGGAGGAAGCTGCCTAGAAACGTCTACAGGATTTGAATGTGTGTGTGCACCTGGCTGG
GCTGGACCAACTTGCACTGATAATATTGATGATTGTTCTCCAAATCCCTGTGGTCATGGAGGAACTTG
CCAAGATCTAGTTGATGGATTTAAGTGTATTTGCCCACCTCAGTGGACTGGCAAAACATGCCAGCTAG
ATGCGAATGAATGTGAGGGCAAACCCTGTGTCAATGCCAACTCCTGCAGGAACTTGATTGGCAGCTAC
TATTGTGACTGCATTACTGGCTGGTCTGGCCACAACTGTGATATAAATATTAATGATTGTCGTGGACA
ATGTCAGAATGGAGGATCCTGTCGGGACTTGGTTAATGGTTATCGGTGCATCTGTTCACCTGGCTATG
CAGGAGATCACTGTGAGAAAGACATCAATGAATGTGCAAGTAACCCTTGCATGAATGGGGGTCACTGC
CAGGATGAAATCAATGGATTCCAATGTCTGTGTCCTGCTGGTTTCTCAGGAAACCTCTGTCAGCTGGA
TATAGACTACTGTGAGCCAAACCCTTGCCAGAACGGTGCCCAGTGCTTCAATCTTGCTATGGACTATT
TCTGTAACTGCCCTGAAGATTACGAAGGCAAGAACTGCTCCCACCTGAAAGATCACTGCCGCACAACT
CCTTGTGAAGTAATCGACAGCTGTACAGTGGCAGTGGCTTCTAACAGCACACCAGAAGGAGTTCGTTA
CATTTCTTCAAATGTCTGTGGTCCTCATGGAAAATGCAAGAGCCAAGCAGGTGGAAAATTCACCTGTG
AATGCAACAAAGGATTCACTGGCACCTACTGTCATGAGAATATCAATGACTGTGAGAGCAACCCCTGT
AAAAATGGTGGCACTTGTATTGACGGTGTAAACTCCTACAAATGTATTTGTAGTGATGGATGGGAAGG
AACATATTGTGAAACAAATATTAATGACTGCAGTAAAAACCCCTGCCACAATGGAGGAACTTGCCGAG
ACTTGGTCAATGACTTCTTCTGTGAATGTAAAAATGGGTGGAAAGGAAAAACTTGCCACTCTCGTGAC
AGCCAGTGTGATGAGGCAACATGCAATAATGGAGGAACATGTTATGATGAGGGGGACACTTTCAAGTG
CATGTGTCCTGCAGGATGGGAAGGAGCCACTTGTAATATAGCAAGGAACAGCAGCTGCCTGCCAAACC
CCTGTCACAATGGTGGTACCTGTGTAGTTAGTGGGGATTCTTTCACTTGTGTCTGCAAGGAGGGCTGG
GAAGGACCGACATGTACTCAGAACACAAATGACTGCAGTCCTCATCCTTGTTACAACAGTGGTACTTG
TGTGGATGGAGACAACTGGTACCGCTGTGAGTGCGCTCCCGGCTTCGCAGGTCCCGACTGTAGGATCA
ACATCAATGAATGTCAGTCTTCACCCTGTGCCTTTGGGGCTACTTGTGTGGATGAAATTAATGGGTAC
CGTTGCATTTGTCCACCGGGTCGCAGTGGTCCAGGATGCCAGGAAGTTACAGGGAGGCCTTGCTTTAC
CAGTATTCGAGTAATGCCAGACGGTGCTAAGTGGGATGATGACTGTAATACTTGTCAGTGTTTGAATG
GAAAAGTCACCTGTTCTAAGGTTTGGTGTGGTCCTCGACCTTGTATAATACATGCCAAAGGTCATAAT
GAATGCCCAGCTGGACACGCTTGTGTTCCTGTTAAAGAAGACCATTGTTTCACTCATCCTTGTGCTGC
```

FIG. 13A

```
AGTGGGTGAATGCTGGCCTTCTAATCAGCAGCCTGTGAAGACCAAATGCAATTCTGATTCTTATTACC
AAGATAATTGTGCCAACATCACCTTCACCTTTAATAAGGAAATGATGGCACCAGGCCTTACCACGGAG
CACATTTGCAGTGAATTGAGGAATCTGAATATCCTGAAGAATGTTTCTGCTGAATATTCCATCTATAT
TACCTGTGAGCCTTCACACTTGGCAAATAATGAAATACATGTTGCTATTTCTGCTGAAGATATAGGAG
AAGATGAAAACCCAATCAAGGAAATCACAGATAAGATTATTGACCTTGTCAGTAAGCGTGATGGAAAC
AACACACTAATTGCTGCAGTCGCAGAAGTCAGAGTACAAAGGCGACCAGTTAAGAACAAAACAGATTT
CTTGGTGCCATTACTGAGCTCAGTCTTAACAGTAGCCTGGATCTGCTGTCTGGTAACTGTTTTCTATT
GGTGCATTCAAAAGCGCAGAAAGCAGAGCAGCCATACTCACACAGCATCTGATGACAACACCACCAAC
AACGTAAGGGAGCAGCTGAATCAGATTAAAAACCCCATAGAGAAACACGGAGCAAATACTGTTCCAAT
TAAAGACTATGAAAACAAAAACTCTAAAATCGCCAAAATAAGGACGCACAATTCAGAAGTGGAGGAAG
ATGACATGGACAAACACCAGCAAAAGGCCCGGTTTGCCAAGCAGCCAGCGTACACTTTGGTAGACAGA
GATGAAAAGCCACCCAACAGCACACCCACAAAACACCCAAACTGGACAAATAAACAGGACAACAGAGA
CTTGGAAAGTGCACAAAGTTTAAATAGAATGGAGTACATTGTATAG
```

FIG. 13B

```
QVASASGQFE LEILSVQNVN GVLQNGNCCD GTRNPGDKKC TRDECDTYFK    50

VCLKEYQSRV TAGGPCSFGS KSTPVIGGNT FNLKYSRNNE KNRIVIPFSF   100

AWPRSYTLLV EAWDYNDNST NPDRIIEKAS HSGMINPSRQ WQTLKHNTGA   150

AHFEYQIRVT CAEHYYGFGC NKFCRPRDDF FTEHTCDQNG NKTCLEGWTG   200
           **********************DSL DOMAIN**********************
PECNKAICRQ GCSPKHGSCT VPGECRCQYG WQGQYCDKCI PHPGCVHGTC   250
***         <---------------EGF 1-------------><--------------
IEPWQCLCET NWGGQLCDKD LNYCGTHPPC LNGGTCSNTG PDKYQCSCPE   300
-----EGF 2----------><----------------EGF 3----
GYSGQNCEIA EHACLSDPCH NGGSCLETST GFECVCAPGW AGPTCTDNID   350
---------------><-----------------EGF 4----------------
DCSPNPCGHG GTCQDLVDGF KCICPPQWTG KTCQLDANEC EGKPCVNANS   400
><--------------------EFG 5-----------------><-----------
CRNLIGSYYC DCITGWSGHN CDININDCRG QCQNGGSCRD LVNGYRCICS   450
--------EFG 6-----------------><----------------EFG 7---
PGYAGDHCEK DINECASNPC MNGGHCQDEI NGFQCLCPAG FSGNLCQLDI   500
--------------><-----------------EFG 8----------------
DYCEPNPCQN GAQCFNLAMD YFCNCPEDYE GKNCSHLKDH CRTTPCEVID   550
-><-------------------EFG 9----------------><---------
SCTVAVASNS TPEGVRYISS NVCGPHGKCK SQAGGKFTCE CNKGFTGTYC   600
-----------------------EFG 10-------------------------
HENINDCESN PCKNGGTCID GVNSYKCICS DGWEGTYCET NINDCSKNPC   650
------><-------------------EFG 11---------------><-----
HNGGTCRDLV NDFFCECKNG WKGKTCHSRD SQCDEATCNN GGTCYDEGDT   700
-------------EFG 12---------------><-----------------
FKCMCPAGWE GATCNIARNS SCLPNPCHNG GTCVVSGDSF TCVCKEGWEG   750
EGF 13------------------><------------------EGF 14------
PTCTQNTNDC SPHPCYNSGT CVDGDNWYRC ECAPGFAGPD CRININECQS   800
---------><-----------------EGF 15----------------><---
SPCAFGATCV DEINGYRCIC PPGRSGPGCQ EVTGRPCFTS IRVMPDGAKW   850
----------------EGF 16------------------>
DDDCNTCQCL NGKVTCSKVW CGPRPCIIHA KGHNECPAGH ACVPVKEDHC   900
          <-                              CYSTEINE-RICH REGION
FTHPCAAVGE CWPSNQQPVK TKCNSDSYYQ DNCANITFTF NKEMMAPGLT   950
              ->
TEHICSELRN LNILKNVSAE YSIYITCEPS HLANNEIHVA ISAEDIGEDE  1000
```

FIG. 14A

```
NPIKEITDKI IDLVSKRDGN NTLIAAVAEV RVQRRPVKNK TDFLVPLLSS 1050

VLTVAWICCL VTVFYWCIQK RRKQSSHTHT ASDDNTTNNV REQLNQIKNP 1100

IEKHGANTVP IKDYENKNSK IAKIRTHNSE VEEDDMDKHQ QKARFAKQPA 1150

YTLVDRDEKP PNSTPTKHPN WTNKQDNRDL ESAQSLNRME YIV         1193
```

FIG. 14B

```
     GAATTCGGCACGAGGTTTTTTTTTTTTTTTTCCCCTCTTTTCTTTCTTTTCCTTTTGCC
     ---------+---------+---------+---------+---------+---------+ 60

ATCCGAAAGAGCTGTCAGCCGCCGCCGGGCTGCACCTAAAGGCGTCGGTAGGGGGATAAC
 61  ---------+---------+---------+---------+---------+---------+ 120

AGTCAGAGACCCTCCTGAAAGCAGGAGACGGGACGGTACCCCTCCGGCTCTGCGGGGCGG
121  ---------+---------+---------+---------+---------+---------+ 180

CTGCGGCCCCTCCGTTCTTTCCCCCTCCCCGAGAGACACTCTTCCTTTCCCCCCACGAAG
181  ---------+---------+---------+---------+---------+---------+ 240

ACACAGGGGCAGGAACGCGAGCGCTGCCCCTCCGCCATGGGAGGCCGCTTCCTGCTGACG
241  ---------+---------+---------+---------+---------+---------+ 300

CTCGCCCTCCTCTCGGCGCTGCTGTGCCGCTGCCAGGTTGACGGCTCCGGGGTGTTCGAG
301  ---------+---------+---------+---------+---------+---------+ 360

CTGAAGCTGCAGGAGTTTGTCAACAAGAAGGGGCTGCTCAGCAACCGCAACTGCTGCCGG
361  ---------+---------+---------+---------+---------+---------+ 420

GGGGGCGGCCCCGGAGGCGCCGGGCAGCAGCAGTGCGACTGCAAGACCTTCTTCCGCGTC
421  ---------+---------+---------+---------+---------+---------+ 480

TGCCTGAAGCACTACCAGGCCAGCGTCTCCCCCGAGCCGCCCTGCACCTACGGCAGCGCC
481  ---------+---------+---------+---------+---------+---------+ 540

ATCACCCCCGTCCTCGGCGCCAACTCCTTCAGCGTCCCCGACGGCGCGGGCGGCGCCGAC
541  ---------+---------+---------+---------+---------+---------+ 600

CCCGCCTTCAGCAACCCCATCCGCTTCCCCTTCGGCTTCACCTGGCCCGGCACCTTCTCG
601  ---------+---------+---------+---------+---------+---------+ 660

CTCATCATCGAGGCTCTGCACACCGACTCCCCCGACGACCTCACCACAGAAAACCCCGAG
661  ---------+---------+---------+---------+---------+---------+ 720

CGCCTCATCAGCCGCCTGGCCACCCAGAGGCACCTGGCGGTGGGCGAGGAGTGGTCCCAG
721  ---------+---------+---------+---------+---------+---------+ 780

GACCTGCACAGCAGCGGCCGCACCGACCTCAAGTACTCCTATCGCTTTGTGTGTGATGAG
781  ---------+---------+---------+---------+---------+---------+ 840
```

FIG. 15A

```
      CACTACTACGGGGAAGGCTGCTCTGTCTTCTGCCGGCCCCGTGACGACCGCTTCGGTCAC
 841  ---------+---------+---------+---------+---------+---------+ 900

TTCACCTGTGGAGAGCGTGGCGAGAAGGTCTGCAACCCAGGCTGGAAGGGCCAGTACTGC
 901  ---------+---------+---------+---------+---------+---------+ 960

ACTGAGCCGATTTGCTTGCCTGGGTGTGACGAGCAGCACGGCTTCTGCGACAAACCTGGG
 961  ---------+---------+---------+---------+---------+---------+ 1020

GAATGCAAGTGCAGAGTGGGTTGGCAGGGGCGGTACTGTGACGAGTGCATCCGATACCCA
1021  ---------+---------+---------+---------+---------+---------+ 1080

GGCTGCCTGCACGGTACCTGTCAGCAGCCATGGCAGTGCAACTGCCAGGAAGGCTGGGGC
1081  ---------+---------+---------+---------+---------+---------+ 1140

GGCCTTTTCTGCAACCAGGACCTGAACTACTGCACTCACCACAAGCCATGCAAGAATGGT
1141  ---------+---------+---------+---------+---------+---------+ 1200

CGGTGTACGTGGTTGTGGCCAGTCCCCTCGATGTGAACAAGAACGGCTGGACCCATGTGT
1201  ---------+---------+---------+---------+---------+---------+ 1260

GGCTCCAGCTGCGAGATTGAAATCAACGAATGTGATGCCAACCCTTGCAAGAATGGTGGA
1261  ---------+---------+---------+---------+---------+---------+ 1320

AGCTGCACGGATCTCGAGAACAGCTATTCCTGTACCTGCCCCCCAGGCTTCTATGGTAAA
1321  ---------+---------+---------+---------+---------+---------+ 1380

AACTGTGAGCTGAGTGCAATGACTTGTGCTGATGGACCGTGCTTCAATGGAGGGCGATGC
1381  ---------+---------+---------+---------+---------+---------+ 1440

ACTGACAACCCTGATGGTGGATACAGCTGCCGCTGCCCACTGGGTTATTCTGGGTTCAAC
1441  ---------+---------+---------+---------+---------+---------+ 1500

TGTGAAAAGAAAATCGATTACTGCAGTTCCAGCCCTTGTGCTAATGGAGCCCAGTGCGTT
1501  ---------+---------+---------+---------+---------+---------+ 1560

GACCTGGGGAACTCCTACATATGCCAGTGCCAGGCTGGCTTCACTGGCAGGCACTGTGAC
1561  ---------+---------+---------+---------+---------+---------+ 1620

GACAACGTGGACGATTGCGCCTCCTTCCCCTGCGTCAATGGAGGGACCTGTCAGGATGGG
1621  ---------+---------+---------+---------+---------+---------+ 1680
```

FIG. 15B

```
      GTCAACGACTACTCCTGCACCTGCCCCCCGGGATACAACGGGAAGAACTGCAGCACGCCG
1681  ---------+---------+---------+---------+---------+---------+ 1740

GTGAGCAGATGCGAGCACAACCCCTGCCACAATGGGGCCACCTGCCACGAGAGAAGCAAC
1741  ---------+---------+---------+---------+---------+---------+ 1800

CGCTACGTGTGCGAGTGCGCTCGGGGCTACGGCGGCCTCAACTGCCAGTTCCTGCTCCCC
1801  ---------+---------+---------+---------+---------+---------+ 1860

GAGCCACCTCAGGGGCCGGTCATCGTTGACTTCACCGAGAAGTACACAGAGGGCCAGAAC
1861  ---------+---------+---------+---------+---------+---------+ 1920

AGCCAGTTTCCCTGGATCGCAGTGTGCGCCGGGATTATTCTGGTCCTCATGCTGCTGCTG
1921  ---------+---------+---------+---------+---------+---------+ 1980

TACCAGTCGGTGTACGTCATATCAGAAGAGAAAGATGAGTGCATCATAGCAACTGAGGTG
2401  ---------+---------+---------+---------+---------+---------+ 2460

TAAAACAGACGTGACGTGGCAAAGCTTATCGATACCGTCATCAAGCTT
2461  ---------+---------+---------+---------+-------- 2508
```

FIG. 15C

```
   1 GAATTCGGCACGAGGTTTTTTTTTTTCCCCTCTTTCTTTCTTTTGCCATCGAAAG              69
  70 AGCTGTCAGCCGCCGCGGGCTGCACCTAAAGGCGTCGGTAGGGGATAACAGTCAGAGACCTCCTGA  138
 139 AAGCAGGAGACGGGACGGTACCCCTCCTCTGCGGGGCGGCTGCGGCCTTCCGTTCTTTCCCCTC    207
 208 CCCGAGAGACACTCTTCCTTCCCCCACGAAGACACAGGGCAGAAACGGCGAGCGCTGCCCCTCCGCC 276
 277 ATGGGAGGCCGCTTCCTGCTGAGCCTTGTCGCAGGAGTTTGTCAACAAGAGGGGCTGTGCCGCAACTGC 345
 346 TCCGGGGTGTTCGAGCTGCTGAAGCTGCACGAGCGCCCGGCAGGCGCCGAGGCGCCGGGTTGACGGC  414
 415 TGCCGGGGGGGGGCGCCCCGGAGGCGCCGGGCAGCAGTGCGACCTTCTTCCGGTCTGC          483
 484 CTGAAGCACTACCAGGCCAGGTCTCCCCCGAGCGCACTACGGCCAAGACGCGACTAGGACCCCATC  552
 553 CTCGGCGCCAACTCCTTCAGCGTCACCTGCCGGCACCTTCTGCATCATGAGGCTCACACCGACTCC  621
 622 CGCTTCCCCTTCGGCTTCACTGCAGCACCACAGAAAACCCGAGCGCCTCATCAGCGCGCTTGGCCACCCAGGCACCTGGCG 690
 691 CCCGACGACCTCACCACAGCAAGATGGTGCCACATGCACAGCGGGCCGCACGACCTCAAGTACTCCTATGCGCTT    759
 760 GTGGGCGAGGAGTGGTCCAGGACGGCGCACAGAGCTGCACAGCGGGGAAGGCTGCTCTGTCTTCTGCCCCGTGACGACCGCTTCGGT 828
 829 XXGTGTGATGAGCACTACTACGGGGAAGGCTGCTCTGTCTTCTGCCCCGTGACGACCGCTTCGGT  897
 898 CACTTCACCTGTGCCTGGGTGTGACGACGAGCAGCAGAAGGTCTGCAACCCAGGCTGCGACACACCAGTACTGCAAGTGCAGA 966
 967 CCGATTGCTTGCCTGGGTGTGACGACGAGCAGCAGAAGGTCTGCAACAAACCTGGGGAATGCAAGTGCAAGTACCTGTCAG 1035
1036 GTGGGTTGGCAGGGGCGTACTGTGACGGAAGGCTGCCATCCGAGTGCACGGTGCTGCACGGTACCTGCTGTCAG  1104
1105 CAGCCATGGCAGTGCAACTGCCAGGAATGCAAGAATCCAGCATGCAACCAGGACGGTCAGGGGAGCTACACTTGTTCT  1173
1174 ACTCACCACAAGCCATGCAAGATGGTGCCACATGCACAGCGGTCAGGGGAGCTACACTTGTTCT  1242
1243 TGCCGACACCTGGGTACACAGGCTCCAGCTGGAGAACAGCTATTCCTGTACCTGCCCCCCCAGGCTTCTATGGTAAA  1311
1312 AATGGTGAAGCTGCACGGATCTCGAGAACAGCTATTCCTGTACCTGCCCCCCCAGGCTTCTATGGTAAA  1380
1381 AACTGTGAGCTGAGTGCAATGCACTTGTGCTGATGAGGGCGATGCACTGACAAC             1449
1450 CCTGATGATGGTGGATACAGCTGCCCTTGTGCTGCCCCACTGGGTTATTGCTGCCCCACTGGGTTCAACTGTGAAAAGAAAATCGAT 1518
1519 TACTGCAGTTCCAGCCCCCTTGTCTGGCAGGCACTGTTGACCCAGTGCGTTGACCTGGGAACTTCTACATATGCCAG  1587
1588 TGCCAGGCTGGCTTCACTGGCAGGCACTGTTGACGACAACGTGGACGATTGCGCCTCTTCCCTGCGTC  1656
1657 AATGCAGGAGGACCTGTCAGGATGGGGTCAACGACTACTCCTGCCCCCGGGATACAAGCGGGAAG  1725
1726 AACTGCAGCACGCCGGTGAGCGAGCAGATGCGAGCACACAACCCCTGCCACAATGGGCCACTGCCACGAGAGA     1794
```

FIG. 16A

```
1795  AGCAACCGCTACGTGTGCGAGTGCGCTCGGGGCTACGGCGGCCTCAACTGCCAGTTCCTGCTCCCCGAG  1863
1864  CCACCTCAGGGGCCGGTCATCGTTGACTTGCACGAGAAGTACACAGAGGGCCAGAACAGCCAGTTTCCC  1932
1933  TGGATCGCAGTGTGCGCCGGGATTATTCTGTGGTCCTCATGCTGCTGGGTTGCGCCGCCATCGTCGTC  2001
2002  TGCGTCAGGTCAGAAGGTGCAAGGTGCACCACAGGCACCACAGCCCGAGGCCTGAAACGGAGACCATG  2070
2071  AACAACCTGGCGAACTGCCAGCGCGAGAAGGACATCTCCATCAGCGTCATCGGTGCCACTCAGATTAAA  2139
2140  AACACAAATAAGAAAGTAGACTTTCACAGCGATAAACTCCGATAAAAACGGCTACAAAGTTAGATACCCA  2208
2209  TCAGTGGATTACACAATTTGGTCATGAACTCAAGAATGAGGACTCTGTGAAAGAGGAGCATGGCAAATGC  2277
2278  GAAGCCAAGTGTGAAACGGCAGTATCAGAGGCAGAAGAGAAAAGCGCAGTACAGCTAAAAGTAGTGAC  2346
2347  ACTTCTGAAAGAAAACGGCCAGATTCAGTATATTCCACTTCAAAGGACACAAAGTACCAGTCGGTGTAC  2415
2416  GTCATATCAGAAGAGAAAGATGAGTGCATCATAGCAACTGAGGTTAGTATCCCACCTGGCAGTCGGACA  2484
2485  AGTCTTGGTGTGTGATTCCAGCAGGTCAGGGCGCCAAACCATTCTACCTGCTGCCACAGTC  2553
2554  ATCTGTACCAATGAAAACTGGCCACCTCAGTCTGTGGCACTGCAGAGTTGAAAAAACTGTTGTGG  2622
2623  ATTAACATAAGCTCCAGTGGGGTTACAGGGACAGCAATTTTTGCAGGCAAGGGTATAACTGTAGTGCA  2691
2692  GTTGTAGCTTACTAACCCTACTGACTCATTCTTGTGTGCTTCCTGCAGAGCCTGTTTTGCTTGGCA  2760
2761  TTGAGGTGAAGTCCTGACCCTCTGCATCCTGCATCCTCAACAGGTGTAAAACAGACGTGACGTGACGTCTCTGGTC  2829
2830  TCTGCTTGTGTTTCTCTCAACAGGTGTAAAACAGACGTGACGTGGCAAAGCTT  2883
```

FIG. 16B

```
  1 MGGRFLLTLA LLSALLCRCQ VDGSGVFELK LQEFVNKKGL LSNRNCCRGG GPGGAGQQQC
 61 DCKTFFRVCL KHYQASVSPE PPCTYGSAIT PVLGANSFSV PDGAGGADPA FSNPIRFPFG
121 FTWPGTFSLI IEALHTDSPD DLTTENPERL ISRLATQRHL AVGEEWSQDL HSSGRTDLKY
181 SYRFVCDEHY YGEGCSVFCR PRDDRFGHFT CGERGEKVCN PGWKGQYCTE PICLPGCDEQ
241 HGFCDKPGEC KCRVGWQGRY CDECIRYPGC LHGTCQQPWQ CNCQEGWGGL FCNQDLNYCT
301 HHKPCKNGAT CTNTGQGSYT CSCRPGYTGS SCEIEINECD ANPCKNGGSC TDLENSYSCT
361 CPPGFYGKNC ELSAMTCADG PCFNGGRCTD NPDGGYSCRC PLGYSGFNCE KKIDYCSSSP
421 CANGAQCVDL GNSYICQCQA GFTGRHCDDN VDDCASFPCV NGGTCQDGVN DYSCTCPPGY
481 NGKNCSTPVS RCEHNPCHNG ATCHERSNRY VCECARGYGG LNCQFLLPEP PQGPVIVDFT
541 EKYTEGQNSQ FPWIAVCAGI ILVLMLLLGC AAIVVCVRLK VQKRHHQPEA CRSETETMNN
601 LANCQREKDI SISVIGATQI KNTNKKVDFH SDNSDKNGYK VRYPSVDYNL VHELKNEDSV
661 KEEHGKCEAK CETYDSEAEE KSAVQLKSSD TSERKRPDSV YSTSKDTKYQ SVYVISEEKD
721 ECIIATEV
```

```
CTGCAGGAAT TCSMYCGCAT GCTCCCCGGCC GCCATGGGCC GTCGGAGCGC GCTAGCCCTT    60
GCCGTGGTCT CTGCCCTGCT GTGCCCAGTC TGGAGCTCCG GCGTATTTGA GCTGAAGCTG   120
CAGGAGTTCG TCAACAAGAA GGGGCTGCTG GGGAACCGCA ACTGCTGCCG CGGGGGCTCT   180
GGCCCCGCCT GCGCCTGCAG GACCTTCTTT CGCGTATGCC TCAAGCACTA CCAGGCCAAG   240
GTGTCACCGG AGCCACCCTG CACCTACGGC AGTGCCGTCA CGCCAGTGCT GGGTGTCGAC   300
TCCTTCAGCC TGCCTGATGG CGCAGGCATC GACCCCCGCT TCAGCAACCC CATCCGATTC   360
CCCTTCGGCT TCACCTGGCC AGTTCGGCC TCTCTGATCA TTGAAGCCCT CCATACAGAC   420
TCTCCCGATG ACCTCGCAAC AGAAAACCCA GAAAGACTCA TCAGCCGCCT GACCACACAG   480
AGGCACCTCA CTGTGGGAGA AGAATGGTCT CAGGACCTTC ACAGTAGCGG CCGCACAGAC   540
CTCCGGTACT CTTACCGGTT TGTGTGTGAC GAGCACTACT ACGGAGAAGG TTGCTCTGTG   600
TTCTGCCGAC CTCGGGATGA CGCCTTTGGC CACTTCACCT GCGGGGACAG AGGGGAGAAG   660
ATGTGCGACC CTGGCTGGAA AGGCCAGTAC TGCACTGACC CAATCTGTCT GCCAGGGTGT   720
GATGACCAAC ATGGATACTG TGACAAACCA GGGGAGTGCA AGTGCAGAGT TGGCTGGCAG   780
GGCCGCTACT GCGATGAGTG CATCCGATAC CCAGGTTGTC TCCATGGCAC CTGCCAGCAA   840
CCCTGGCAGT GTAACTGCCA GGAAGGCTGG GGGGCCCTTT TCTGCAACCA AGACCTGAAC   900
TACTGTACTC ACCATAAGCC GTGCAGGAAT GGAGCCACCT GCACCAACAC GGGCCAGGGG   960
AGCTACACAT GTTCCTGCCG ACCTGGGTAT ACAGGTGCCA ACTGTGAGCT GGAAGTAGAT  1020
GAGTGTGCTC CTAGCCCCTG CAAGAACGGA GCGAGCTGCA CGGACCTTGA GGACAGCTTC  1080
TCTTGCACCT GCCCCTCCGG CTTCTATGGC AAGGTCTGTG AGCTGAGCGC CATGACCTGT  1140
GCAGATGGCC CTTGCTTCAA TGGAGGACGA TGTTCAGATA ACCCTGACGG AGGCTACACC  1200
TGCCATTGCC CCTTGGGCTT CTCTGGCTTC AACTGTGAGA AGAAGATGGA TCTCTGCGGC  1260
TCTTCCCCTT GTTCTAACGG TGCCAAGTGT GTGGACCTCG GCAACTCTTA CCTGTGCCGG  1320
TGCCAGGCTG GCTTCTCCGG GAGGTACTGC GAGGACAATG TGGATGACTG TGCCTCCTCC  1380
```

FIG. 19A

```
CCGTGTGCAA ATGGGGGCAC CTGCCGGGAC AGTGTGAACG ACTTCTCCTG TACCTGCCCA 1440
CCTGGCTACA CGGGCAAGAA CTGCAGCGCC CCTGTCAGCA GGTGTGAGCA TGCACCCTGC 1500
CATAATGGGG CCACCTGCCA CCAGAGGGGC CAGCGCTACA TGTGTGAGTG CGCCCAGGGC 1560
TATGCGGCC CCAACTGCCA GTTTCTGCTC CCTGAGCCAC CACCAGGGCC CATGGTGGTG 1620
GACCTCAGTG AGAGGCATAT GGAGAGCCAG GGCGGGCCCT TCCCCTGGGT GGCCGTGTGT 1680
GCCGGGGTGG TGCTTGTCCT CCTGCTGCTG CTGGGCTGTG CTGCTGCGTC GGTCTGCGTC 1740
CGGCTGAAGC TACAGAAACA CCAGCCCTCA CCTGAACCCT GTGGGGGAGA GACAGAAACC 1800
ATGAACAACC TAGCCAATTG CCAGCGCGAG AAGGACGTTT CTGTTAGCAT CATTGGGGCT 1860
ACCCAGATCA AGAACACCAA CAAGAAGGCG GACTTTCACG GGGACCATGG AGCCGAGAAG 1920
AGCAGCTTTA AGTCCCGATA CCCCACTGTG GACTATAACC TCGTTCGAGA CCTCAAGGGA 1980
GATGAAGCCA CGGTCAGGGA TACACACAGC AAACGTGACA CCAAGTGCCA GTCACAGAGC 2040
TCTCAGGAG AAGAGAAGAT CGCCCCAACA CTTAGGGGTG GGGAGATTCC TGACAGAAAA 2100
AGGCCAGAGT CTGTCTACTC TACTTCAAAG GACACCAAGT ACCAGTCGGT GTATGTTCTG 2160
TCTGCAGAAA AGGATGAGTG TGTTATAGCG ACTGAGGTGT AAGATGGAAG CGATGTGGCA 2220
AAATTCCCAT TTCTCTTAAA TAAAATTCCA AGGATATAGC CCCGATGAAT GCTGCTGAGA 2280
GAGGAAGGGA GAGGAAACCC AGGGACTGCT GCTGAGAACC AGGTTCAGGC GAACGTGGTT 2340
CTCTCAGAGT TAGCAGAGGC GCCCGACACT GCCAGCCTAG GCTTTGGCTG CCGGCTGGACT 2400
GCCTGCTGGT TGTTCCCATT GCACTATGGA CAGTTGCTTT GAAGAGTATA TATTTAAATG 2460
GACGAGTGAC TTGATTCATA TAGGAAGCAC GCACTGCCCA CACGCTCTATC TTGGATTACT 2520
ATGAGCCAGT CTTTCCTTGA ACTAGAAACA CAACTGCCTT TATTGTCCTT TTTGATACTG 2580
AGATGTGTTT TTTTTTTTTC CTAGACGGGA AAAAGAAAAC GTGTGTTATT TTTTTTGGGA 2640
TTTGTAAAA TATTTTTCAT GATTATGGGA GAGCTCCCAA CGGCGTTGGAG GT 2692
```

FIG. 19B

```
MGRRSALALA VVSALLCQVW SSGVFELKLQ EFVNKKGLLG NRNCCRGGSG    50
PPCACRTFFR VCLKHYQASV SPEPPCTYGS AVTPVLGVDS FSLPDGAGID   100
PAFSNPIRFP FGFTWPGTFS LIIEALHTDS PDDLATENPE RLISRLTTQR   150
HLTVGEEWSQ DLHSSGRTDL RYSYRFVCDE HYYGEGCSVF CRPRDDAFGH   200
FTCGDRGEKM CDPGWKGQYC TDPICLPGCD DQHGYCDKPG ECKCRVGWQG   250
RYCDECIRYP GCLHGTCQQP WQCNCQEGWG GLFCNQDLNY CTHHKPCRNG   300
ATCTNTGQGS YTCSCRPGYT GANCELEVDE CAPSPCKNGA SCTDLEDSFS   350
CTCPPGFYGK VCELSAMTCA DGPCFNGGRC SDNPDGGYTC HCPLGFSGFN   400
CEKKMDLCGS SPCSNGAKCV DLGNSYLCRC QAGFSGRYCE DNVDDCASSP   450
CANGGTCRDS VNDFSCTCPP GYTGKNCSAP VSRCEHAPCH NGATCHQRGQ   500
RYMCECAQGY GGPNCQFLLP EPPPGPMVVD LSERHMESQG GPFPWVAVCA   550
GVVLVLLLLL GCAAVVVCVR LKLQKHQPPP EPCGGETETM NNLANCQREK   600
DVSVSIIGAT QIKNTNKKAD FHGDHGAEKS SFKVRYPTVD YNLVRDLKGD   650
EATVRDTHSK RDTKCQSQSS AGEEKIAPTL RGGEIPDRKR PESVYSTSKD   700
TKYQSVYVLS AEKDECVIAT EV                                722
```

FIG. 20

```
          10         20         30         40         50         60
                      *                     *                     *
TACGATGAAY AACCTGGCGA ACTGCCAGCG TCAGAAGGAC ATCTCAGTCA GCATCATCGG 70         80         90        100        110        120
                      *                     *                     *
GGCYACGTCA GATCARGAAC ACCAACAAGA AGGCGGACTT YMCASCGGGG GACCASAGCG 130        140        150        160        170        180
                      *                     *                     *
TCCGACAAGA ATGGMTTTCA AGGCCYGCTA CCCCAGCGTG GACTATAACT CGTGCAGGAC 190        200        210        220        230        240
                      *                     *                     *
CTCAAGGGTG ACGACACCGC CGTCAGGACG TCGCACAGCA AGCGTGACAC CAAGTGCCAG 250        260        270        280        290        300
                      *                     *                     *
TCCCCAGGCT CCTCAGGGAG GAGAAGGGGA CCCCGACCAC ACTCAGGGGK TGCGTGCTGC 310        320        330        340        350        360
                      *                     *                     *
GGGCCGGGCT CAGGAGGGGG TACCTGGGGG GTGTCTTCCT GGAACCACTG CTCCGTTTCT
```

FIG. 21A

```
         370        380        390        400        410        420
                     *                     *                     *
CTTCCCAAAT GTTCTCATGC ATTCATTGTG GATTTTCTCT ATTTTCCTTT TAGTGGAGAA 430        440        450        460        470        480
                     *                     *                     *
GCATCTGAAA GAAAAAGGCC GGACTCGGGC TGTTCAACTT CAAAAGACAC CAAGTACCAG 490        500        510        520
                     *                     *
TCGGTGTACG TCATATCCGA GGAGAAGGAC GAGTGCGTCA TCGCA
```

FIG. 21B

```
          10         20         30         40         50         60
          *  *       *  *       *  *       *  *       *  *       *  *
    CATTGGGTAC GGGCCCCCCT CGAGGTCGAC GGTATCGATA AGCTTGATAT CGAATTCCGG
          70         80         90        100        110        120
          *  *       *  *       *  *       *  *       *  *       *  *
    CTTCACCTGG CCGGGCACCT TCTCTCTGAT TATTGAAGCT CTCCACACAG ATTCTCCTGA
         130        140        150        160        170        180
          *  *       *  *       *  *       *  *       *  *       *  *
    TGACCTCGCA ACAGAAAACC CAGAAAGACT CATCAGCCGC CTGGCCACCC AGAGGCACCT
         190        200        210        220        230        240
          *  *       *  *       *  *       *  *       *  *       *  *
    GACGGTGGGC GAGGAGTGGT CCCAGGACCT GCACAGCAGC GGCCGCACGG ACCTCAAGTA
         250        260        270        280        290        300
          *  *       *  *       *  *       *  *       *  *       *  *
    CTCCTACCGC TTCGTGTGTC ACCAACACTA CTACGGAGAG GGCTGCTCCG TTTTCTGCCG
         310        320        330        340        350        360
          *  *       *  *       *  *       *  *       *  *       *  *
    TCCCCGGGAC GATGCCTTCG GCCACTTCAC CTGTGGGGAG CGTGGGGAGA AAGTGTGCAA
         370        380        390        400        410        420
          *  *       *  *       *  *       *  *       *  *       *  *
    CCCTGGCTCG AAAGGGCCCT ACTGCACAGA GCCGATCTGC CTGCCTGGAT GTGATGAGCA
         430        440        450        460        470        480
          *  *       *  *       *  *       *  *       *  *       *  *
    GCATGGATTT TGTGACAAAC CAGGGGAATG CAAGTGCAGA GTGGGCTGGC AGGGCCGGTA
         490        500        510        520        530        540
          *  *       *  *       *  *       *  *       *  *       *  *
    GTGTGACGAG TGTATCCGCT ATCCAGGCTG TCTCCATGGC ACCTGCCAGC AGCCCTGGCA
         550        560        570        580        590        600
          *  *       *  *       *  *       *  *       *  *       *  *
    GTGCAACTGC CAGGAAGGNT GGGGGGGCCT TTTCTGCAAC CAGGACCTGA ACTACTGCAC
         610        620        630        640        650        660
          *  *       *  *       *  *       *  *       *  *       *  *
    ACACCATAAG CCCTGCAAGA ATGGAGCCAC CTGCAACAAA CACGGGCCAG GGGGAGCTAC
         670        680        690        700        710        720
          *  *       *  *       *  *       *  *       *  *       *  *
    ACTTGGTCTT TGGCCGGNCT GGGGTACANA GGGTGCCACC TGCGAAGCTT GGGGATTGGA
         730        740        750        760        770        780
          *  *       *  *       *  *       *  *       *  *       *  *
    CGAGTTGTTG ACCCCAGCCC TTGGTAAGAA CGGAGGGAGC TTGACGGATC TTCGGAGAAC
         790        800        810        820        830        840
          *  *       *  *       *  *       *  *       *  *       *  *
    AGCTACTCCT GTACCTGCCC ACCCGGCTTC TACGGCAAAA TCTGTGAATT GAGTGCCATG
         850        860        870        880        890        900
          *  *       *  *       *  *       *  *       *  *       *  *
    ACCTGTGCGG ACGGCCCTTG CTTTAACGGG GGTCGGTGCT CAGACAGCCC CGATGGAGGG
```

FIG. 22A

```
              910        920        930        940        950        960
        *     *     *     *     *     *     *     *     *     *     *     *
       TACAGCTGCC GCTGCCCCGT GGGCTACTCC GGCTTCAACT GTGAGAAGAA AATTGACTAC
              970        980        990       1000       1010       1020
        *     *     *     *     *     *     *     *     *     *     *     *
       TGCAGCTCTT CACCCTGTTC TAATGGTGCC AAGTGTGTGG ACCTCGGTGA TGCCTACCTG
             1030       1040       1050       1060       1070       1080
        *     *     *     *     *     *     *     *     *     *     *     *
       TGCCGCTGCC AGGCCGGCTT CTCGGGGAGG CACTGTGACG ACAACGTGGA CGACTGCGCC
             1090       1100       1110       1120       1130       1140
        *     *     *     *     *     *     *     *     *     *     *     *
       TCCTCCCCGT GCGCCAACGG ACCTCGGTGA CGGGATGGCG TGAACGACTT CTCCTGCACC
             1150       1160       1170       1180       1190       1200
        *     *     *     *     *     *     *     *     *     *     *     *
       TGCCCGCCTG GCTACACGGG CAGGAACTGC AGTGCCCCCG CCAGCACCTG CGAGCACGCA
             1210       1220       1230       1240       1250       1260
        *     *     *     *     *     *     *     *     *     *     *     *
       CCCTGCCACA ATGGGGCCAC CTGCCACGAG AGGGGCCACC GCTATNTGTG CGAGCACGCA
             1270       1280       1290       1300       1310       1320
        *     *     *     *     *     *     *     *     *     *     *     *
       CGAAGCTACG GGGGTCCCAA CTCCCANTTC CTGCTCCCCC AAACTGCCCC CCCGGCCGCCA
             1330       1340       1350       1360       1370       1380
        *     *     *     *     *     *     *     *     *     *     *     *
       CGGTGGTGGA AACTCCCCTA AAAAAACCTA AAAGGGCCGG GGGGGGCCCA TCCCCTTGGT
             1390       1400       1410       1420       1430       1440
        *     *     *     *     *     *     *     *     *     *     *     *
       GGACGTGTGC GCCGGGGTCA TCCTTGTCCT CATGCTGCTG CTGGGCTGTG CCGCTGTGGT
             1450       1460       1470       1480       1490       1500
        *     *     *     *     *     *     *     *     *     *     *     *
       GGTCTGCGTC CGGCTGAGGC TGCAGAAGCA CCGGCCCCCA GCCGACCCCT GNCGGGGGGA
             1510       1520       1530       1540       1550       1560
        *     *     *     *     *     *     *     *     *     *     *     *
       GACGGAGACC ATGAACAACC TGGNCAACTG CCAGCGTGAG AAGGACATCT CAGTCAGCAT
             1570       1580       1590       1600       1610       1620
        *     *     *     *     *     *     *     *     *     *     *     *
       CATCGGGGNC ACGCAGATCA AGAACACCAA CAAGAAGGCG GACTTCCACG GGACCACAG
             1630       1640       1650       1660       1670       1680
        *     *     *     *     *     *     *     *     *     *     *     *
       NGCCGACAAG AATGGCTTCA AGGCCCGCTA CCCAGNGGTG GACTATAACC TCGTGCAGGA
             1690       1700       1710       1720       1730       1740
        *     *     *     *     *     *     *     *     *     *     *     *
       CCTCAAGGGT GACGACACCG CCGTCAGCCA CGCGCACAGC AAGCGTGACA CCAAGTGNCA
             1750       1760       1770       1780       1790       1800
        *     *     *     *     *     *     *     *     *     *     *     *
       GCCCCAGGGC TCCTCAGGGG AGGAGAAGGG GACCCCCGAC CCACACTCAG GGGGTGGAGG
```

FIG. 22B

```
          1810       1820       1830       1840       1850       1860
           *  *       *  *       *  *       *  *       *  *       *  *
AAGCATCTTG AAAGAAAAAG GCCGGACTTC GGGCTTGTTC AACTTTCAAA AGACAANCAA
          1870       1880       1890       1900       1910       1920
           *  *       *  *       *  *       *  *       *  *       *  *
NGTACAAGTC GGTGTNCGTC ATTTCCGNAG GAGGAAGGNT GACTGCGTCA TAGGAANTTG
          1930       1940       1950       1960       1970       1980
           *  *       *  *       *  *       *  *       *  *       *  *
AGGTNGTAAA NTGGNAGTTG ANNTTGGAAA GNNNTCCCCG GATTCCGNTT TCAAAGTTTT
T
```

NOTCH

This application is a continuation of U.S. application Ser. No. 09/310,685, filed on May 4, 1999, which is continuation-in-part of PCT application PCT/GB97/03058, filed Nov. 6, 1997 and designating the U.S., published as WO 98/20142 on May 14, 1998 and claiming priority to U.K. application nos. GB 9623236.8, GB 9715674.9, and GB 9719350.2, filed Nov. 7, 1996, Jul. 24, 1997 and Sep. 11, 1997, respectively; and each of these applications, each document cited in each of these applications, and all documents cited in the following text, are hereby incorporated herein by reference.

The present invention relates to use of therapeutic compounds in the modification of T-cell activation. In particular it relates to their use in modulating the interaction between Notch protein family members and their ligands and to the use of such compounds in the therapy of conditions such as graft rejection, autoimmunity, allergy, asthma, infectious diseases and tumours.

The controlled interaction between T cells and between antigen presenting cells (APC) and T cells is vital to the function of the human immune system. However in certain pathological states it may be therapeutically beneficial to modify, positively or negatively, such interactions. For example, in conditions such as autoimmunity, allergy and graft rejection it is desirable to induce the downregulation of an immune response by stimulation of negative T cell or T cell-APC interaction. Models of "infectious tolerance" and "linked suppression" suggest that tolerance may be induced in a small number of T cells and that these T cells then transmit this tolerance to other T cells thus preventing an effective immunological attack. In other pathological conditions such as tumour induced immunosuppression, parasitic viral or bacterial infections, immunosuppression is a common feature. In such circumstances it would therefore be desirable to inhibit the T cell interactions passing on the infectious tolerance.

However until now the mechanisms underlying such T cell and T cell-APC interactions have not been understood.

WO 92/19734 purports to disclose the nucleotide sequences of the human Notch and Delta genes and amino acid sequences of their encoded proteins. The disclosure shows that the Notch gene family has been well characterised as essential to the correct embryological cell lineage development of insects such as *Drosophila*.

Proteins belonging to the Notch family are transmembrane receptors that contain several conserved peptide motifs. Each protein within the family displays characteristic extracellular EGF (epidermal growth factor)-like repeats and a juxtamembrane Lin-12/Notch motif. In addition each protein has 6-8 ankyrin repeat motifs on the cytoplasmic tail together with a PEST sequence. The Notch ligands have a diagnostic DSL domain (D. Delta, S, Serrate, L,Lag2) comprising 20-22 amino acids at the amino terminus of the protein and between 3-8 EGF-like repeats on the extracellular surface. The proteins have a short cytoplasmic tail with no conserved functional domains.

Recent evidence suggests that Notch signalling contributes to lineage commitment of immature T cells in the thymus, biasing thymocyte development towards the CD8+ lineage which is independent of MHC recognition (Robey E, et al. Cell 1996, 87:483492). During maturation in the thymus, T cells acquire the ability to distinguish self antigens from those that are non-self, a process termed self tolerance (von Boehmer H, et al. Ann Rev Immunol. 1990;8:531). Mechanisms also exist in the periphery for the induction and maintenance of tolerance and in many respects their importance is under estimated. There are many experimental models of graft rejection, autoimmune disease and specific responses to allergens that clearly illustrate the ability to induce a state of specific unresponsiveness (tolerance or anergy) in the recipient by immunisation with an antigen. From these systems two important findings arise. Firstly, immunisation with a peptide fragment of antigen under selected conditions may inhibit specific responses not only to itself but to other regions in the same molecule provided the intact protein is used for the challenge immunisation (linked suppression; Hoyne G F, et al. J. Exp Med. 1993; 178:183. and Metzler B, Wraith D C. Int. Immunol. 1993;5:1159). Secondly, as best described in experimental models of transplantation is the phenomenon of "infectious tolerance" where it is postulated that immunocompetent cells made tolerant to a specific antigen are able to inhibit other cells from responding and further, that this second population of cells becomes regulatory and tolerant (Qin SX, et al. Science 1993;258:974). The immunological mechanisms underlying these phenomena have not so far been characterised.

The present invention arises from the discovery that the Notch receptor family and its ligands, Delta and Serrate, are expressed on the cell surface of normal adult cells of the peripheral immune system.

Hence there is provided according to the present invention, the use of a Notch-ligand in the manufacture of a medicament for use in immunotherapy.

The expression pattern of the Notch family of receptors and their ligands in the normal peripheral adult immune system has not previously been described but the present inventors have shown that T cells express Notch 1 mRNA constitutively, while Delta expression is limited to only a subset of T cells in the peripheral lymphoid tissues. Serrate expression appears restricted to a subset of antigen presenting cells (APCs) in the periphery (FIG. 1). Hence this receptor ligand family may continue to regulate cell fate decisions in the immune system as has been shown in other tissues, beyond embryonic development (Ellisen L W, et al. Cell 1991;66: 649). Notch signalling may play a central role in the induction of peripheral unresponsiveness (tolerance or anergy) and may provide a physical explanation for linked suppression and infectious tolerance.

The present invention further relates to the use of a Notch-ligand in the treatment of a T cell mediated reaction. Thus, it has been observed that by exposing a population of naive T cells to a Notch-ligand expressed by an APC in the presence of an allergen or antigen, the Notch-ligand is capable of making the T cell population tolerant to said allergen or antigen. Furthermore, this T cell population, when subsequently exposed to a second population of naive T cells is capable of rendering the second population tolerant to said allergen or antigen.

Thus, the invention also relates to the use of a Notch-ligand in affecting linked tolerance and/or bystander tolerance (also known in the art as infectious tolerance).

A further embodiment of the invention relates to the use of a Notch-ligand in the modulation of the expression of a functional Notch-protein or Notch signalling pathways.

In the above described embodiments of the present invention, the Notch-ligand may be exposed to the T cells by incubating/mixing the T cells with antigen presenting cells (APCs) or the like, that express or overexpress a Notch-ligand in the presence of an allergen or antigen. The (over)expression of the Notch-ligand gene may be brought about by the APCs being transfected with a gene capable of expressing a Notch-ligand or by the APCs being exposed to an agent capable of up-regulating expression of endogenous Notch-ligand gene(s).

Suitable agents that influence expression of Notch-ligands include agents that affect the expression of Delta and/or Serrate genes. For instance, for Delta expression, binding of extracellular BMPs (bone morphogenetic proteins, Wilson, P. A. and Hernmati-Brivanlou A.1997 Neuron 18: 699-710, Hemmati-Brivanlou, A and Melton, D. 1997 Cell 88:13-17) to their receptors leads to down-regulated Delta transcription due to the inhibition of the expression of the Achaete/Scute Complex transcription factor. This complex is believed to be directly involved in the regulation of Delta expression. Thus, any agent that inhibits the binding of BMPs to their receptors is capable of producing an increase in the expression of Delta and/or Serrate. Such agents include Noggin. Chordin, Follistatin, Xnr3, FGFs, Fringe and derivatives and variants thereof (see references for noggin-Smith W. C. and Harland, R. M Cell 70:829-840, chordin-Sasai, Yet al., 1994 Cell 79: 779-790). Noggin and Chordin bind to BMPs thereby preventing activation of their signalling cascade which leads to decreased Delta transcription.

In some disease states, the body may be immuno-compromised and it may be desirable to downregulate the expression of Delta and/or Serrate in order to overcome the imposed immunosuppression. Agents that inhibit the expression of Delta and/or Serrate may be used in such circumstances. An example of agents that inhibit the expression of Delta and/or Serrate include the Toll protein (Medzhitov, R. et al., 1997 Nature 388: 394-397) BMPs and other agents that decrease or interfere with the production of Noggin, Chordin, Follistatin. Xnr3, FGFs and Fringe. Thus, the invention further relates to the use of an agent capable of downregulating the expression of Delta or Serrate proteins in the manufacture of a medicament for use in reversing bacteria infection or tumour-induced immunosuppression.

As discussed above, the invention also relates to the modification of Notch-protein expression or presentation on the cell membrane or signalling pathways. These have been shown to be involved in T-cell mediated responses that participate in the induction of tolerance (linked and/or bystander). Agents that enhance the presentation of a fully functional Notch-protein on the cell surface include matrix metalloproteinases such as the product of the Kuzbanian gene of *Drosophila* (Dkuz, Pan, D and Rubin, G. M. 1997 Cell 90: 271-280) and other ADAMALYSIN gene family members. Agents that reduce or interfere with its presentation as a fully functional cell membrane protein may include MMP inhibitors such as hydroxymate-based inhibitors.

The term "antigen presenting cell or the like" as used herein, is not intended to be limited to APCs. The skilled man will understand that any vehicle capable of presenting the desired Notch-ligand to the T cell population may be used for the sake of convenience the term APCs is used to refer to all these. Thus examples of suitable APCs include dendritic cells. L cells, hybridomas, lymphomas, macrophages, B cells or synthetic APCs such as lipid membranes.

When the APCs are transfected with a gene capable of expressing a Notch-ligand, the transfection may be brought about by a virus such as a retrovirus or adenovirus, or by any other vehicle or method capable of delivering a gene to the cells. These include any vehicles or methods shown to be effective in gene therapy and include retroviruses, liposomes, electroporation, other viruses such as adenovirus, adeno-associated virus, herpes virus, vaccinia, calcium phosphate precipitated DNA, DEAE dextran assisted transfection, microinjection, polyethylene glycol, protein-DNA complexes.

Using such vehicles or methods alone or in combination it is possible to site-direct the gene delivery to a particular population of cells, thus enabling the method of the present invention to be performed in vivo. For example, a virus may be used in combination with liposomes in order to increase the efficiency of DNA uptake. The site specificity of the delivery may be achieved by the inclusion of specific proteins (eg a single chain antibody reactive with CD11c for dendritic cells/macrophages) in the viral coat or liposome.

Preferably, constructs through which expression of the gene (eg serrate) is linked to antigen expression would be used. APCs (over)expressing Serrate would therefore also express high levels of the relevant antigen and so preferentially interact with T cells of the appropriate specificity.

A further embodiment of the present invention relates to a molecule comprising a Notch-ligand moiety operably linked to a T cell allergen or antigen moiety such that upon exposure to T cells both moieties are capable of binding to their respective sites. Such a molecule is capable of rendering an antigen/allergen specific T cell tolerant to the allergen or antigen upon which the allergen or antigen moiety is based, as the specificity required of the Notch-ligand moiety is provided by the close proximity of the allergen or antigen moiety.

The antigen or allergen moiety may be, for example, a synthetic MHC-peptide complex. That is a fragment of the MHC molecule bearing the antigen groove bearing an element of the antigen. Such complexes have been described in Altman J D et al Science 1996 274: 94-6.

In a further preferred embodiment, the compound is a fusion protein comprising a segment of Notch or Notch ligand extracellular domain and an immunoglobulin $F_c$ segment, preferably $IgGF_c$ or $IgMF_c$.

In all the above described embodiments of the present invention, it is preferable that the Notch-ligand is of the Serrate family of proteins or Delta family of proteins, derivatives, fragments or analogs thereof.

Diseased or infectious states that may be described as being mediated by T cells include any one or more of asthma, allergy, graft rejection, autoimmunity, tumour induced abberations to the T cell system and infectious diseases such as those caused by *Plasmodium* species, Microfilariae, Helminths, Mycobacteria, HIV, Cytomegalovirus, *Pseudomonas, Toxoplasma, Echinococcus, Haemophilus influenza* type B, measles, Hepatitis C or Toxicara. Thus, with use of the appropriate allergen or antigen, a Notch-ligand may be used in accordance with the present invention to treat the said disease or infection.

The invention also provides a method for detecting immune suppression induced by an invading organism. Such organisms may generate soluble forms of family members of Serrate, Notch and/or Delta or derivatives thereof or proteins that affect their expression in vivo, thus inducing infectious tolerance immunosuppression. The method comprises an assay for the presence of in vivo non-membrane bound Serrate, Delta, Notch or derivatives thereof and preferably comprises an antibody to Serrate, Delta or Notch or their derivatives.

Methods of use in screening assays for the detection of increased or decreased Notch, Delta/Serrate expression and/or processing include:

1. Delta/Serrate, Notch and Fringe expression being assessed following exposure of isolated cells to test compounds in culture using for example:
   (a) at the protein level by specific antibody staining using immunohistochemistry or flow cytometry.
   (b) at the RNA level by quantitative-reverse transcriptase-polymerase chain reaction (RT-PCR). RT-PCR may be performed using a control plasmid with in-built standards for measuring endogenous gene expression with primers specific for Notch 1 and Notch 2, Serrate 1 and Serrate 2, Delta 1 and Delta 2, Delta 3 and Fringe. This construct may be modified as new ligand members are identified.

(c) at the functional level in cell adhesion assays.

Increased Delta/Serrate or Notch expression should lead to increased adhesion between cells expressing Notch and its ligands Delta/Serrate. Test cells will be exposed to a particular treatment in culture and radiolabelled or flourescein labelled target cells (transfected with Notch/Delta/Serrate protein) will be overlayed. Cell mixtures will be incubated at 37 degrees C. for 2 hr. Nonadherent cells will be washed away and the level of adherence measured by the level of radioactivity/immunofluorescence at the plate surface.

Using such methods it is possible to detect compounds or Notch-ligands that affect the expression or processing of a Notch-protein or Notch-ligand. The invention also relates to compounds, or Notch-ligands detectable by these assay methods.

The invention also includes an assay method comprising contacting (a) Notch protein and a ligand capable of binding to the Notch protein with (b) a compound: and determining if the compound affects binding of the ligand to the Notch protein preferably wherein the Notch protein is associated with a T cell.

The Notch-ligands of use in the present invention are preferably Delta or Serrate family member proteins or polypeptides or derivatives thereof. These are preferably obtained using standard techniques of recombinant technology well known to the person skilled in the art. Appropriate gene sequences for use to generate such compounds of the present invention may be obtained from publications such as WO97/01571, WO 96/27610 and WO 92/19734. The invention is not however in any way limited by the Notch, Delta and Serrate invention is not however in any way limited by the Notch, Delta and Serrate sequences disclosed in these publications. More preferably, such Notch, Delta or Serrate or family members, proteins or polypeptides or derivatives therefrom are fragments of the extracellular domains of Notch, Delta or Serrate, or family members or are derivatives of such fragments. As used herein, the term "Notch ligand" further includes any ligand or ligand family member that interacts with a Notch protein family member and includes the group of proteins referred to as "toporythmic proteins" i.e. the protein product of the Delta, Serrate, Deltex and Enhancer of split genes as well as other members of this gene family identifiable by virtue of the ability of their gene sequences to hybridize to, or their homology with Notch, Delta or Serrate proteins, or the ability of their genes to display phenotypic interactions.

Notch, Delta and Serrate were first described in *Drosophila* and therefore represent prototypic proteins of the Notch receptor and Notch-ligand family members respectively. Multiple Notch proteins and ligands have now been described in many invertebrate and vertebrate species but their nomenclature may differ from that used in the fly. For example Notch is a homolog of Lin 12 and Glp 1, Serrate/Delta are homologs of Jagged, Apx1 and Lag-2.

Pharmaceutical formulations of the present invention may be formulated according to principles well known in the art. Thus the nature of the excipient and the amount of activity will depend upon the compound of the present invention which is to be formulated.

Preferably the pharmaceutical compositions are in unit dosage form. Dosages of compounds of the present invention, to be administered to a patient in the form of a pharmaceutical formulation, could be determined by a suitable physician, for instance, taking into account such factors as the age, weight, sex, species, general health/condition of the patient, the condition to be treated, timing of treatments. the $LD_{50}$ of the active ingredient involved in a suitable animal mode (e.g., rodent, mice), and other known factors: and such dosages can be on the order of micrograms to milligrams such as on the order of 0.5 to 500 micrograms, or another suitable amount, or can be computed from Examples herein, e.g., considering the average weight of a typical test animal (such as mice) and the dosages administered thereto (e.g., 100 micrograms), and thus the skilled artisan can determine dosages without undue experimentation.

The preferred administration route of a formulation of the present invention is any one of the usual methods of administration including intramuscular and intra-peritoneal, intravenous injection, intranasal inhalation, lung inhalation subcutaneous, intradermal, intra-articular, intrathecal, topical, and via the alimentary tract (for example, via the Peyers patches).

Examples of compositions of the invention include liquid preparations for orifice, e.g., oral, nasal, anal, vaginal, peroral, intragastric, mucosal (e.g., perlingual, alveolar, gingival, olfactory or respiratory mucosa) etc., administration such as suspensions, syrups or elixirs; preparations for parenteral, subcutaneous, intradermal, intramuscular or intravenous administration (e.g., injectable administration), such as sterile suspensions or emulsions; and, preparations for topical administration, e.g., creams, gels, ointments and the like. Such compositions may be in admixture with a suitable carrier, diluent, or excipient such as sterile water, physiological saline, glucose or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions of the invention are conveniently provided as liquid preparations, e.g., isotonic aqueous solutions, suspensions, emulsions or viscous compositions which may be buffered to a selected pH. If digestive tract absorption is preferred, compositions of the invention can be in the "solid" form of pills, tablets, capsules, caplets and the like, including "solid" preparations which are time-released or which have a liquid filling, e.g., gelatin covered liquid, whereby the gelatin is dissolved in the stomach for delivery to the gut.

If nasal or respiratory (mucosal) administration is desired, compositions may be in a form and dispensed by a squeeze spray dispenser, pump dispenser or aerosol dispenser. Aerosols are usually under pressure by means of a hydrocarbon. Pump dispensers can preferably dispense a metered dose or, a dose having a particular particle size. "A self-pressurized packaging form with a permanently attached continuous or metering valve and designed to dispense products such as sprays, streams, gels, foams, lotions or gases" is a typical term for an "aerosol". An "aerosol" is also "small particles of a liquid or solid suspended in gas." Thus, liquids and/or solids can be in an aerosol form of the invention; and, the particle size thereof can be any suitable amount for absorption by mucosal, e.g., alimentary tract, lungs, nasal mucosa, and the like, such as having a majority of particles by weight, e.g., 90% by wt or greater such as 95% by wt or greater having an average diameter or size of about 10 μm—about 100 μm for nasal absorption, and a majority of particles, e.g., 90% by wt or greater such as 95% by wt or greater having a diameter or size less than about 10 μm, e.g., about 3—about 7 μm for absorption in the lungs; see, e.g., U.S. Pat. No. 5,804,212 and documents cited therein, hereby incorporated herein by reference.

Compositions of the invention can contain pharmaceutically acceptable flavors and/or colors for rendering them more appealing, especially if they are administered orally. The viscous compositions may be in the form of gels, lotions, ointments, creams and the like and will typically contain a sufficient amount of a thickening agent so that the viscosity is from about 2500 to 6500 cps, although more viscous compositions, even up to 10,000 cps may be employed. Viscous compositions have a viscosity preferably of 2500 to 5000 cps, since above that range they become more difficult to administer. However, above that range, the compositions can approach solid or gelatin forms which are then easily administered as a swallowed pill for oral ingestion.

Liquid preparations are normally easier to prepare than gels, other viscous compositions, and solid compositions. Additionally, liquid compositions are somewhat more convenient to administer, especially by injection or orally, to animals, children, particularly small children, and others who may have difficulty swallowing a pill, tablet, capsule or the like, or in multi-dose situations. Viscous compositions, on the other hand, can be formulated within the appropriate viscosity range to provide longer contact periods with mucosa, such as the lining of the stomach or nasal mucosa.

Obviously, the choice of suitable carriers and other additives will depend on the exact route of administration and the nature of the particular dosage form, e.g., liquid dosage form (e.g., whether the composition is to be formulated into a solution, a suspension, gel or another liquid form), or solid dosage form (e.g., whether the composition is to be formulated into a pill, tablet, capsule, caplet, time release form or liquid-filled form).

Solutions, suspensions and gels, normally contain a major amount of water (preferably purified water) in addition to the antigen, lipoprotein and optional adjuvant. Minor amounts of other ingredients such as pH adjusters (e.g., a base such as NaOH), emulsifiers or dispersing agents, buffering agents, preservatives, wetting agents, jelling agents, (e.g., methylcellulose), colors and/or flavors may also be present. The compositions can be isotonic, i.e., it can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount which will achieve the selected viscosity. Viscous compositions are normally prepared from solutions by the addition of such thickening agents.

A pharmaceutically acceptable preservative can be employed to increase the shelf life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected. Those skilled in the art will recognize that the components of the compositions must be selected to be chemically inert with respect to the active ingredient. This will present no problem to those skilled in chemical and pharmaceutical principles, or problems can be readily avoided by reference to standard texts or by simple experiments (not involving undue experimentation), from this disclosure and the documents cited herein.

In addition, compositions of the invention can be administered in conjunction with other therapy in accordance with this invention, or can be administered in conjunction with other therapies for the condition being treated, either simultaneously or sequentially; and, therapy can be administered in intervals suitable for treating the particular condition being treated, without undue experimentation, by the practitioner taking into consideration typical factors, such as those discussed herein.

The compositions of this invention are prepared by mixing the ingredients following generally accepted procedures. For example, the selected components may be simply mixed in a blender, or other standard device to produce a concentrated mixture which may then be adjusted to the final concentration and viscosity by the addition of water or thickening agent and possibly a buffer to control pH or an additional solute to control tonicity. Generally the pH may be from about 3 to 7.5. Compositions can be administered in dosages and by techniques well known to those skilled in the medical and veterinary arts taking into consideration such factors as mentioned herein, e.g., the age, sex, weight, and condition of the particular patient or animal, and the composition form used for administration (e.g., solid vs. liquid). Dosages for humans or other mammals can be determined without undue experimentation by the skilled artisan, from this disclosure, the documents cited herein, the Examples below (e.g., from the Examples involving mice).

The term "derivative" as used herein, in relation to proteins or polypeptides of the present invention includes any substitution of, variation of, modification of, replacement of, deletion of or addition of one (or more) amino acid residues from or to the sequence providing that the resultant protein on polypeptide possesses the capability of modulating Notch-Notch ligand interactions.

The term "variant" as used herein, in relation to proteins or polypeptides of the present invention includes any substitution of, variation of, modification of, replacement of, deletion of or addition of one (or more) amino acid residues from or to the sequence providing that the resultant protein on polypeptide possesses the capability of modulating Notch-Notch ligand interactions.

The term "analog" as used herein, in relation to proteins or polypeptides of the present invention includes any peptidomimetic, that is, a chemical compound that possesses the capability of modulating Notch-Notch ligand interactions in a similar manner to the parent protein or polypeptide. These include compounds that may agonise or antagonise the expression or activity of a Notch-protein or Notch-ligand.

A compound may be considered to modulate Notch-Notch ligand interactions if it is capable of either inhibiting or enhancing the interaction of Notch with its ligands, preferably to an extent sufficient to provide therapeutic efficacy.

The expression "Notch-Notch ligand" as used herein means the interaction between a Notch family member and a ligand capable of binding to one or more such member.

The term therapy as used herein should be taken to encompass diagnostic and prophylactic applications.

The term "medical" includes human and veterinary applications.

As used herein, the terms protein and polypeptide may be assumed to be synonymous, protein merely being used in a general sense to indicate a relatively longer amino acid sequence than that present in a polypeptide.

The present invention will now be described by way of non-limiting example, with reference to the accompanying drawings, in which:

FIG. 1 shows the results of in situ hybridisations carried out as described in Example 1 herein;

FIG. 4 shows the results of the experiment described in Example 6.

FIGS. 10A-10F show sequences (SEQ ID NO:1 and SEQ ID NO:2).

FIGS. 11A-11G show sequences (SEQ ID NO:3 and SEQ ID NO:4).

FIGS. 12A-12G show sequences (SEQ ID NO:5 and SEQ ID NO:6).

FIGS. 13A and 13B show a sequence (SEQ ID NO:7).

FIGS. 14A and 14B show a sequence (SEQ ID NO:8).

FIGS. 15A-15C show a sequence (SEQ ID NO:9).

FIGS. 16A and 16B show a sequence (SEQ ID NO: 10).

FIG. 17 shows a sequence (SEQ ID NO:11).

Figure 18B:
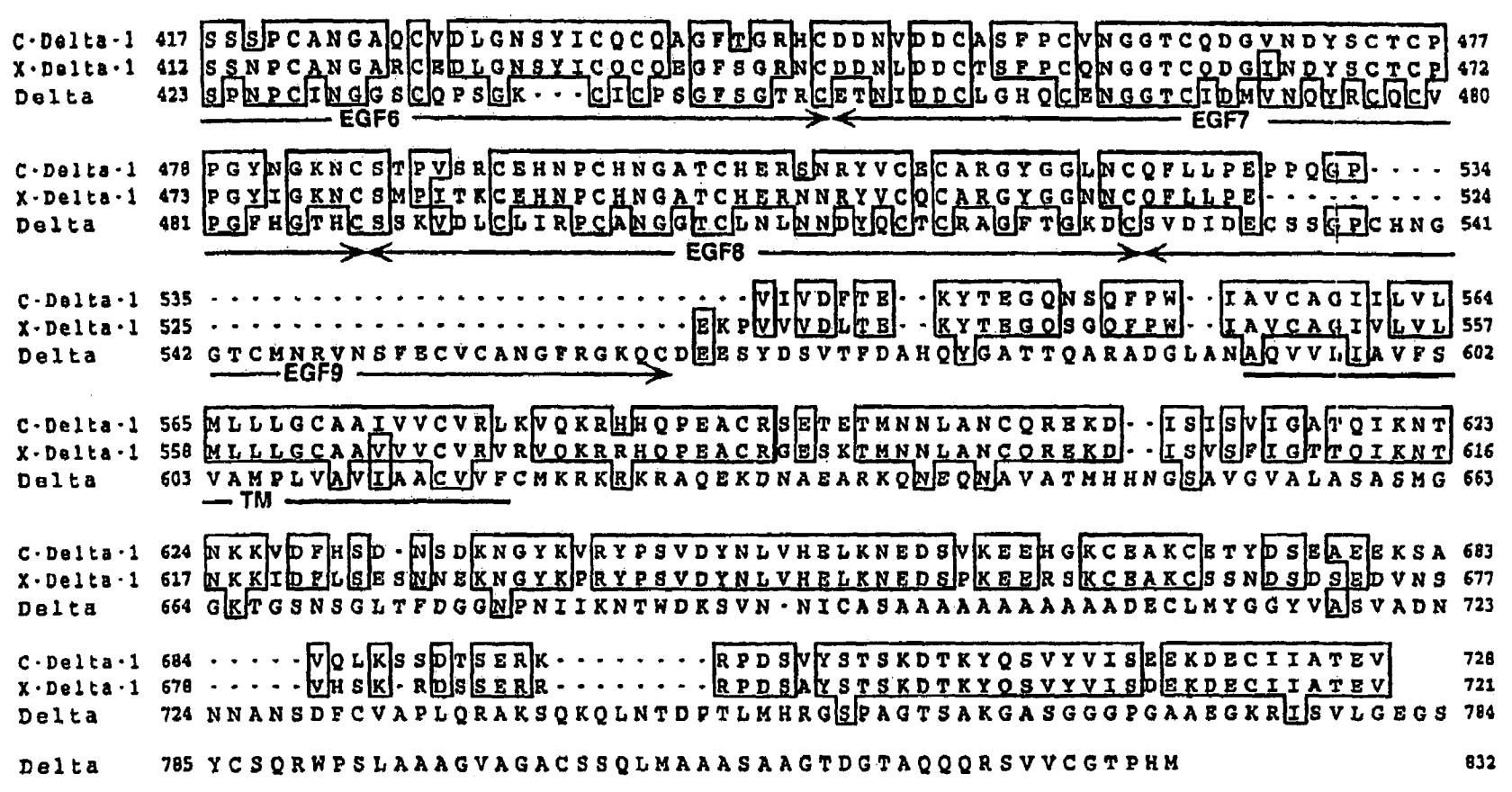

FIGS. 18A and 18B show sequences (SEQ ID NO:11, SEQ ID NO:12 and SEQ ID NO:2).

FIGS. 19A and 19B show a sequence (SEQ ID NO:13).

FIG. 20 shows a sequence (SEQ ID NO:14).

FIGS. 21A and 21B show a sequence (SEQ ID NO:15).

FIGS. 22A-22C show a sequence (SEQ ID NO:16).

Figure 23A:
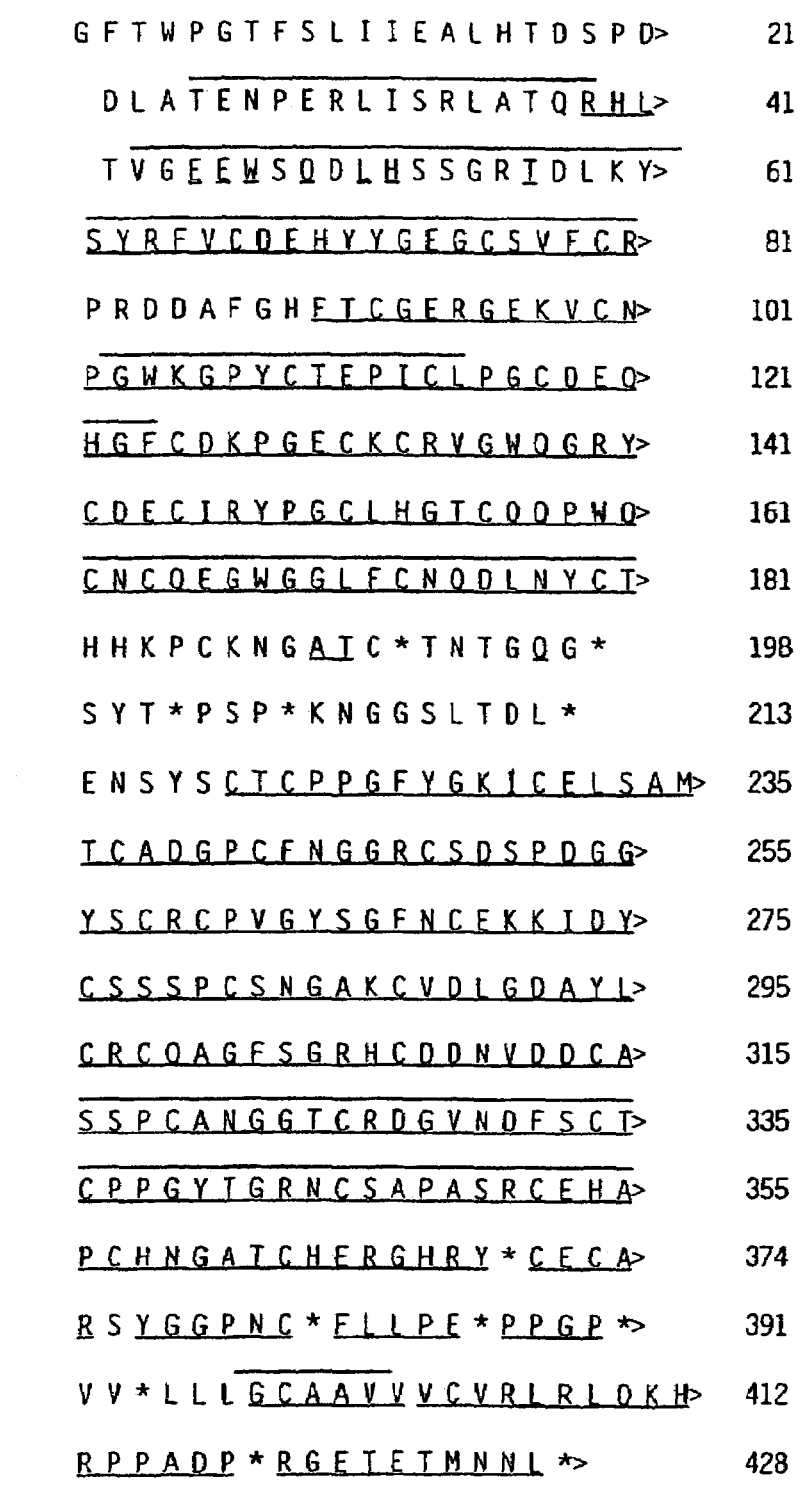
Figure 23B:
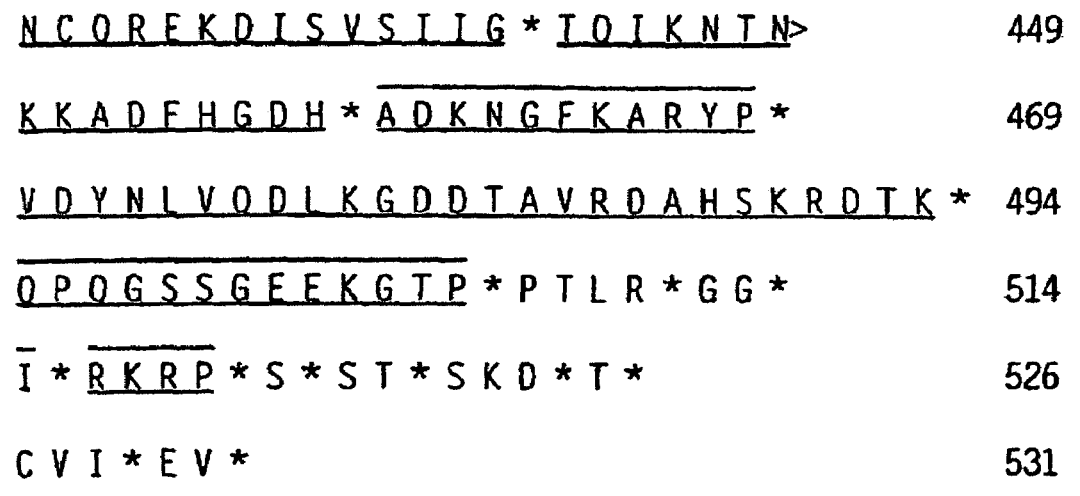

FIGS. 23A and 23B show a sequence (SEQ ID NOs:17-32).

EXAMPLE 1

Figure 2:
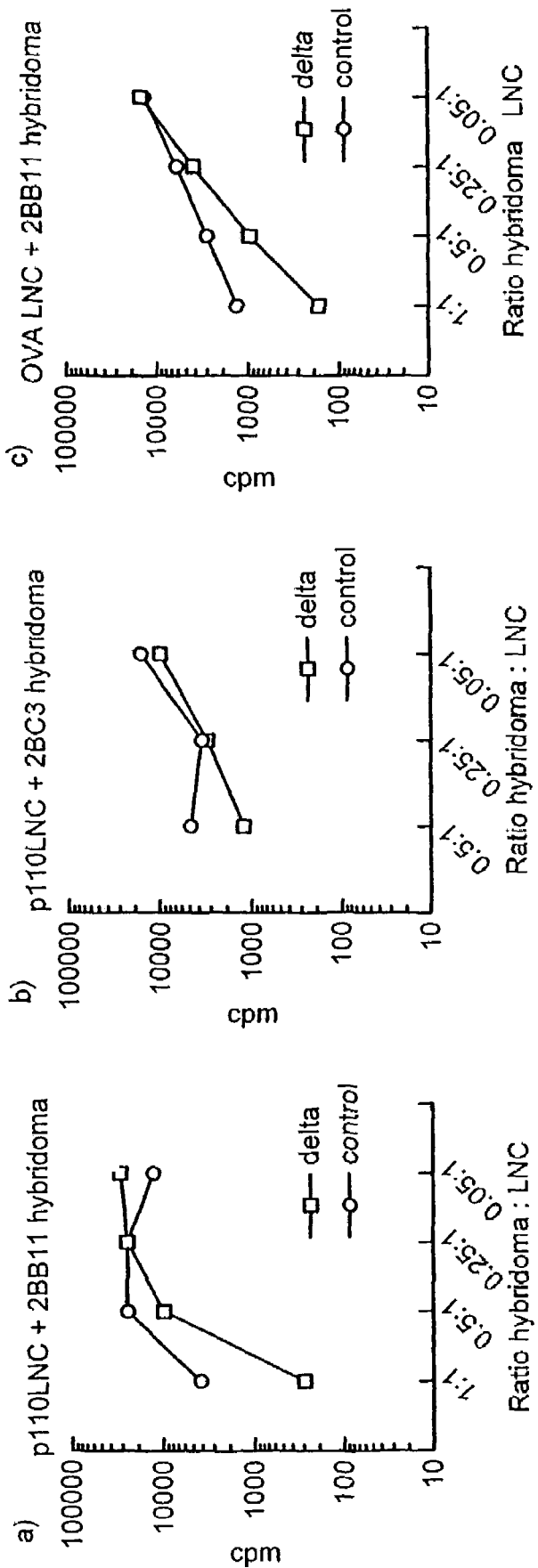
FIG. 2 shows the results of the experiment described in Example 4.

Notch, Delta and Serrate are Expressed in the Peripheral Immune System

Antisense RNA probes specific for Notch 1, Delta 1 and Serrate 1 were synthesized and incorporated with digoxigenin labelled-UTP. Each probe was dissolved in hybridisation buffer, heated to 70° C. for 5-10 minutes and added to TESPA coated slides containing 10 mm sections of spleen or thymus that had been previously fixed with 4% paraformaldehyde+ PBS. Slides were hybridized overnight at 65° C. The following day, slides were washed twice at 65° C. and twice at room temperature (RT) with 1×SSC/50% Formamide/0.1% Tween 20. Slides were washed twice with 0.1M maleic acid/0.15M NaCl/0.1% tween 20 pH 7.5 (MABT) buffer at RT and then blocked for 2 h with MABT+20% goat serum+296 Boehringer blocking reagent (BBR). Slides were incubated overnight at RT with anti-digoxidenin Fab fragments. After four washes with MABT slides were washed a further two times in alkaline substrate buffer. The presence of bound anti-sense RNA probes was detected by incubating slides in substrate buffer containing NBT+BCIP in the dark. Slides were conterstained with haemotoxylin and mounted in Depx mounting medium.

Results: The results of these hybridisations are shown in FIG. 1, that shows that in a spleen from a 3 month old mouse, Delta and Serrate are expressed by isolated cells in the periarteriolar sheath and not in the germinal centre(gc). Notch is expressed in many cells again in the periarteriolar sheath.

EXAMPLE 2

Production of Delta-Fc Fusion Protein

The pIG-1 [D. Simmons, "Cloning cell surface molecules by transient surface expression in mammalian cells" pp 93-128, Cellular Interactions in Development Ed. D. Hartley, pub. Ox. Uni. Press (1993)] expression vector allows production of a fusion protein that contains the extracellular portion of Delta 1 linked to the human IgG1-$F_c$ domain. A restriction enzyme fragment that contained only the extracellular domain of the Delta 1 protein was cloned into the pIG-1 vector. The resultant plasmid was transformed into *E. Coli* MC 1061, and grown in SOB containing 10 µg/ml tetracycline/ampicillin. Purified vector was used to transfect COS cells in vitro. COS cells were grown to 50-75% confluency and transfected with 10 µg of plasmid DNA per dish by DEAE-dextran method. At 24 h post transfection the culture medium was replaced with culture medium containing 1% FCS and cells were cultured for a further 3-6 days in vitro. Cells were spun for 5 mins/5000 rpm to pellet cells and debris, the supernatant was removed and stored until required. The Delta-Fc fusion was purified from culture supernatants by adding 2 ml of 50% slurry of protein a Sepharose (Phamacia) and rotated overnight at 4° C. Sepharose beads were isolated by passing culture supernatants through a 0.45 mm filter, washed and transferred to a 10 ml plastic column. The Delta-$F_c$ fusion construct was eluted with 2 ml of elution buffer pH 4.0. The eluate was neutralised by the addition of 1M Tris base.

EXAMPLE 3

Examples of Models in which the Notch-Ligand Signalling Pathway May be Investigated Peripheral tolerance to self antigens can be analysed in T cell receptor (TCR) transgenic mice in which the TCR ligand is expressed as a self antigen only in the periphery. Peripheral tolerance to transplantation antigens can be induced in several ways including recipient pre-treatment with T cell antibodies or blockade of costimulation. It is thereby possible to demonstrate both linked suppression and infectious tolerance. Peripheral tolerance to allergens may be induced by the intranasal delivery of allergen derived peptides. The expression of Notch-Notch ligands is measured on cells recruited into the airways and/or lymphoid tissues following allergen inhalation and modifications in tolerance demonstrated. Furthermore, in experimental models of infections with infectious agents, the expression of Notch-Notch ligands can be measured on the organism (pathogen) and immunocompetent cells in the host.

EXAMPLE 4

Delta Expressing Hybridomas can Inhibit the Responses of Antigen Primed Lymphocytes Mice were immunised with a synthetic peptide containing an immunodominant epitope of the house dust mite allergen (HDM), Der p1 (p110-31), or with ovalbumin (OVA, hen egg white protein). One week later the lymph node cells (LNCs) were removed and cell suspensions made. Lymph nodes from animals immunised with different antigens were kept separate. These cells are referred to as primed LNCs.

T cell hybridomas were transfected with either full length Delta or a control plasmid, such that delta was expressed as a membrane protein. After two days in culture the hybridomas were irradiated to prevent them from proliferating or from producing cytokines. Therefore, the only response which was measured in the assay comes from the lymph node cells alone.

The irradiated hybridomas were added in increasing numbers to cultures containing the primed LNCs. The appropriate antigen (i.e. p110-131 or OVA) was added and the cells cultured for 24 hours. Supernatent fluids were then collected and assayed for IL-2 (a major T cell growth factor) content. Proliferative responses of the lymph node cells after 72 hours were also measured.

Results: Lymph node cells cultured in the presence of irradiated hybridomas that expressed a control plasmid still proliferated as shown in FIG. 2 and secreted IL-2 when stimulated in culture with the appropriate antigen. Their responsiveness was maintained at a ratio of 1:1 LNC:hybridoma. In contrast, the proliferative response and production of IL-2 by lymph node cells was reduced by at least 88% when cultured in the presence of hybridomas expressing full length Delta (at a ratio of 1:1) with the appropriate antigen. Hybridomas transfected with control virus (open circles), delta virus (open squares). FIG. 2 shows the data presented as counts per minute (cpm) $^3$H-Tdr incorporation 72 hours after the beginning of culture. Cpm of lymph node cells (LNC) cultured with hybridomas expressing delta or control constructs. Total numbers of cells/well=$4\times10^5$ (i.e the number of LNCs varies according to the ratio of hybridomas to LNC, so the cpm will vary). p110-131 LNC are cells primed with Der p1 (p110-131), OVA LNC are cells primed with OVA. 2BB11 and 2BC3 are two different Der p1 reactive hybridomas.

Figure 8A:
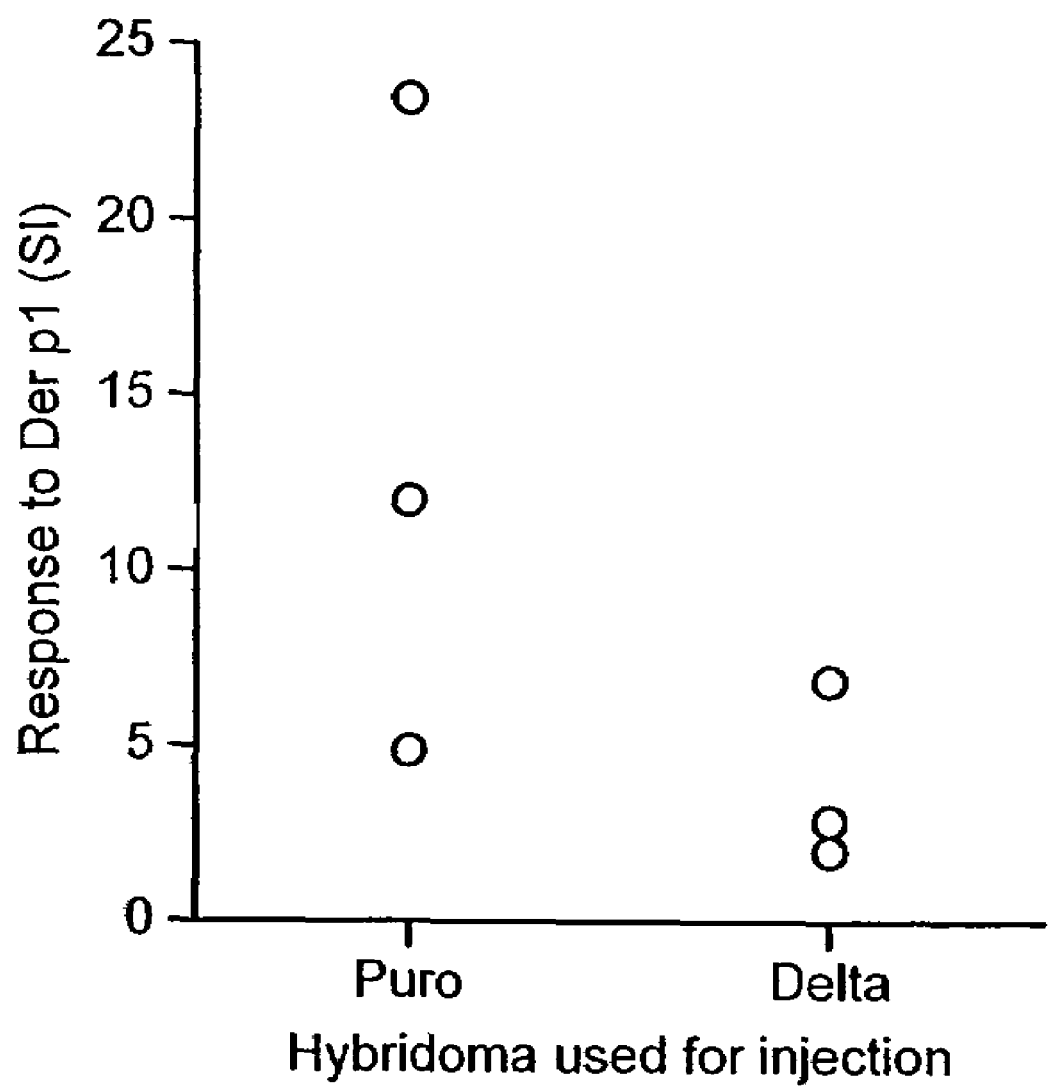
FIGS. 8a and 8b show the results of the experiment described in Example 10.
Figure 8B:
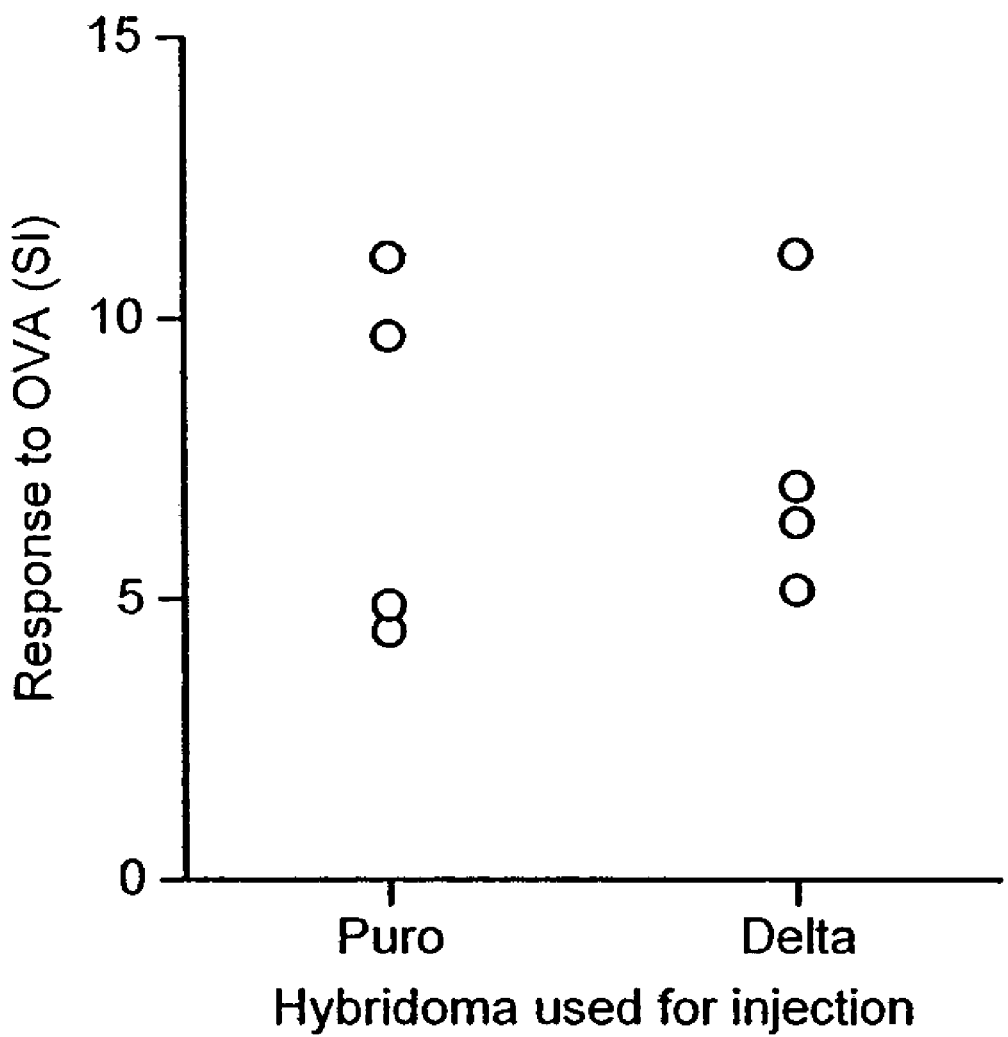
Figure 9:
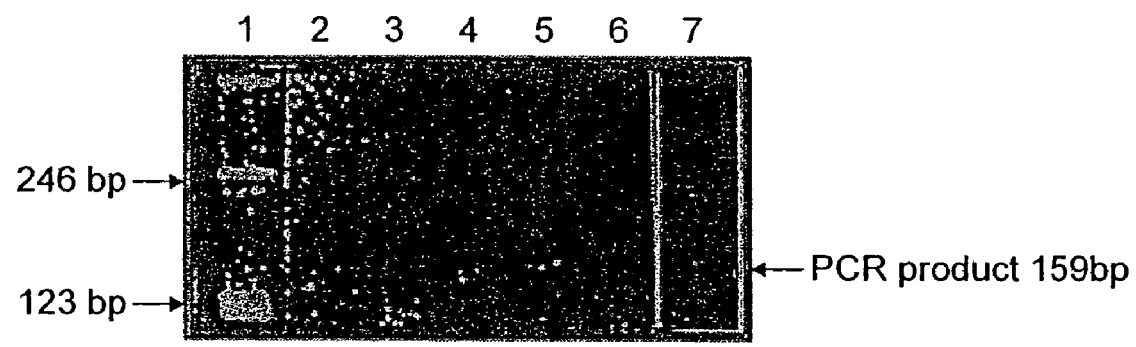
FIG. 9 shows the results of the experiment described in Example 11.
Figure 18A:
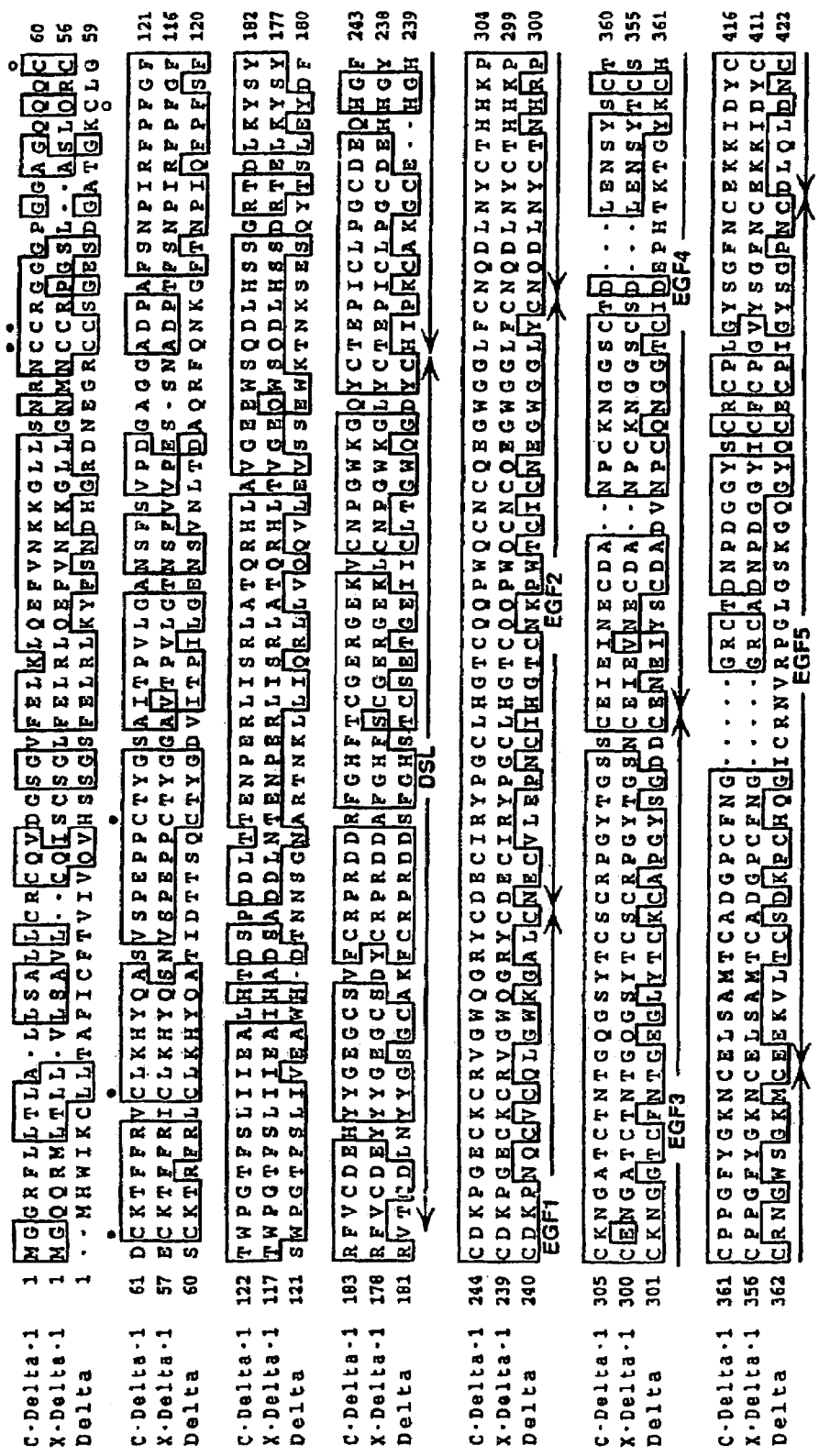

These data show that inhibition of responses by Delta expressing T cells can be delivered in trans. Although in this culture system Delta expressing T hybridomas specific for Derp 1 were able to inhibit the response of OVA primed T cells, this apparent lack of specificity appears to be due to the close proximity of cells forced by the culture system. Indeed, the data shown in FIGS. 8a and 8b show that in animals the delta expressing hybridoma must share antigen specificity with the immunogen for there to be an modulating effect on the immune response to that immunogen. In this case it appears that the delta expressing T cells can only be brought into proximity with the responding T cells if they recognise the same antigen on the same APC.

EXAMPLE 5

Serrate Expressing Dendritic Cells Prevent Antigen Priming of T Lymphocytes

Dendritic cells (DCs) are the primary antigen presenting cell in the immune system and are critical for stimulating T cell responses. DCs were obtained from the spleen and transfected with either a retrovirus allowing expression of the full length Serrate protein or a control retrovirus. The DCs were also pulsed with the HDM peptide p110-131 for 3 hours in vitro at 37° C. The DCs were then washed and used to immunise naive mice subcutaneously using $10^5$ cells/mouse. After 7 days the draining LNCs were recovered and restimulated in culture with peptide at $4\times10^5$ cells/well. Since the mice were only immunised with peptide-pulsed DCs this gives us a measure of the ability of these cells to prime an immune response.

Figure 3:
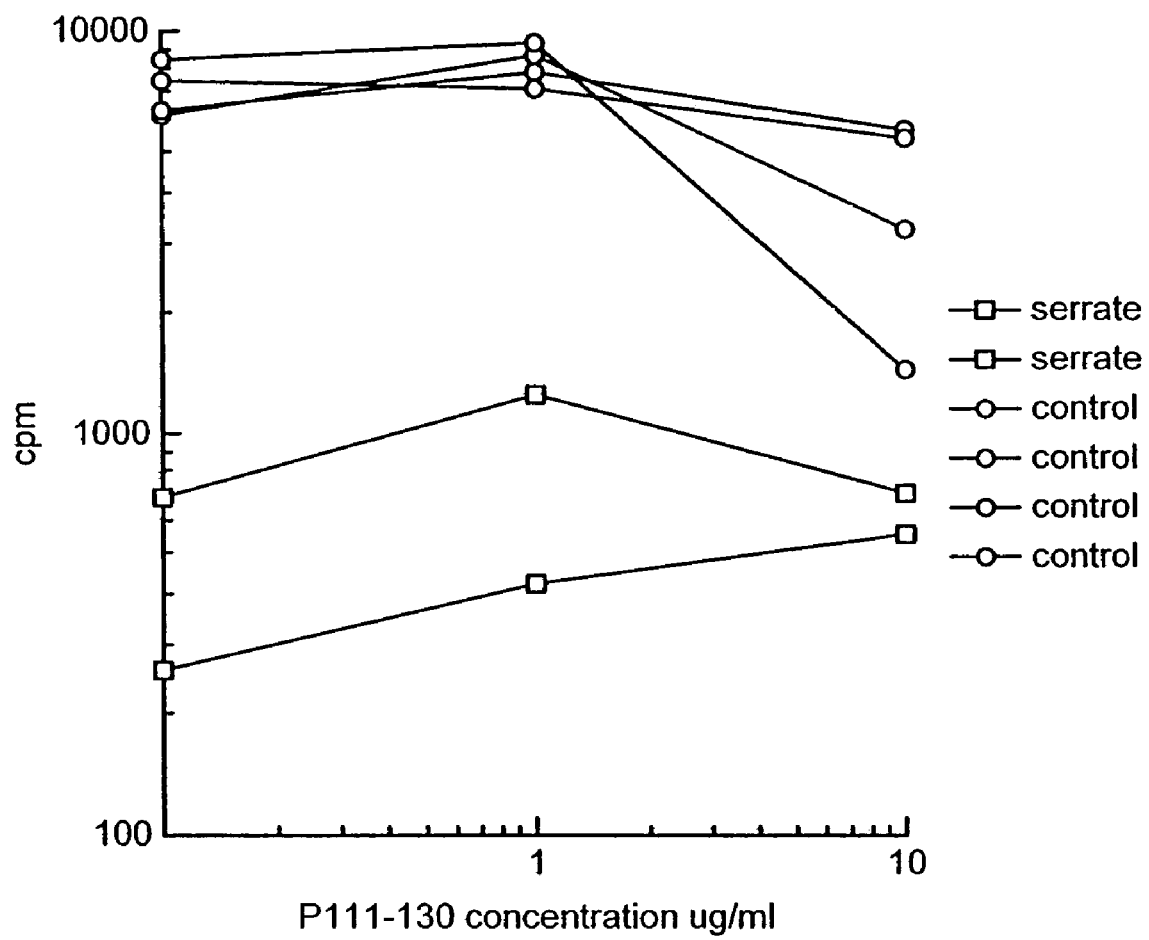
FIG. 3 shows the results of the experiment described in Example 5.

Results: FIG. 3 shows the data presented as cpm of LNCs 72 hours after culture from animals immunised with control transfected (open circles) or serrated transfected (open squares) dendritic cells (DCs).

Immunisation of mice with DCs expressing Serrate resulted in a 10 fold decrease in the number of cells recovered from lymph nodes when compared to immunisation with control DCs. We further found that LNCs from mice immunised with DCs+Serrate failed to proliferate (93% reduction on control values, FIG. 3) or secrete IL-2 when compared to cells from mice immunised with control DCs.

EXAMPLE 6

Delta Expressing T Cell Hybridomas are Able to Inhibit the Development of Immunity to Der p 1 Antigen in Animals T cell hybridomas (reactive with Der p 1) were transfected with a retrovirus containing mouse Delta such that Delta was expressed on the cell surface or with a control retrovirus. C57 BL mice were injected with 10 million irradiated hybridomas i.p. and inmmunised with 50 microgram Der p 1 emulsified in Complete Freunds Adjuvant (CFA) sub-cutaneously. After 7 days the draining lymph node cells were collected and cultured at $4\times10^5$ cells/well with Der p 1 (10 microgram/ml), peptide 110-131 of Der p 1 (10 microgram/ml), or peptide 81-102 of Der p 1 (10 microgram/ml). Cultures were incubated at 37° C. for 72 hours and tritiated thymidine added for the final 8 hours of culture. Results of proliferation assays of cells from animals injected with control transfected (puro) or Delta transfected (Delta-FL) are shown in FIG. 4.

Results: LNC from animals injected with control virus transfected hybridomas produced high levels of IL-2 and proliferated in culture in the presence of Der p 1, peptide 110-131 or peptide 81-102. In contrast, cells from animals injected with Delta expressing hybridomas made no response to any of the Der p 1 antigens (FIG. 4).

EXAMPLE 7

Delta Expressing Human T Cells Can Block the Response of Normal T Cells

An influenza-reactive human T cell clone (HA1.7) was transfected with mouse Delta using a retroviral construct to allow cell surface expression of the Delta protein. Mixing of this cell population with normal HA1.7 prevented subsequent reactivity of these normal HA1.7 with peptide HA306-318 and antigen presenting cells. $5\times10^5$ HA1.7 were mixed with $1\times10^6$ irradiated DRB1*0101 pripheral blood mononuclear cells (PBMC)+1 microgram HA306-318 and cultured at 37° C. 6 hours later 5% lymphocult (IL-2 containing medium) was added in a total volume of 1 ml. 24 hours after the initiation of culture Delta or control retrovirus or nothing was added. 7 days after the start of culture, cells were harvested, washed and the transfected cells irradiated. The transfected cells were mixed at a ratio of 2:1 with untreated HA1.7 and cultured for 2 days. Mixed cultures were then harvested, washed and plated out using $2 \times 10^4$ viable cells/well together with a) $2.5 \times 10^4$ DRB1*0101 PBMCs (medium)

b) $2.5 \times 10^4$ DRB1*0101 PBMCs+peptide (Ag+ APC)

c) 5% lymphocult (IL-2)

Figure 5:
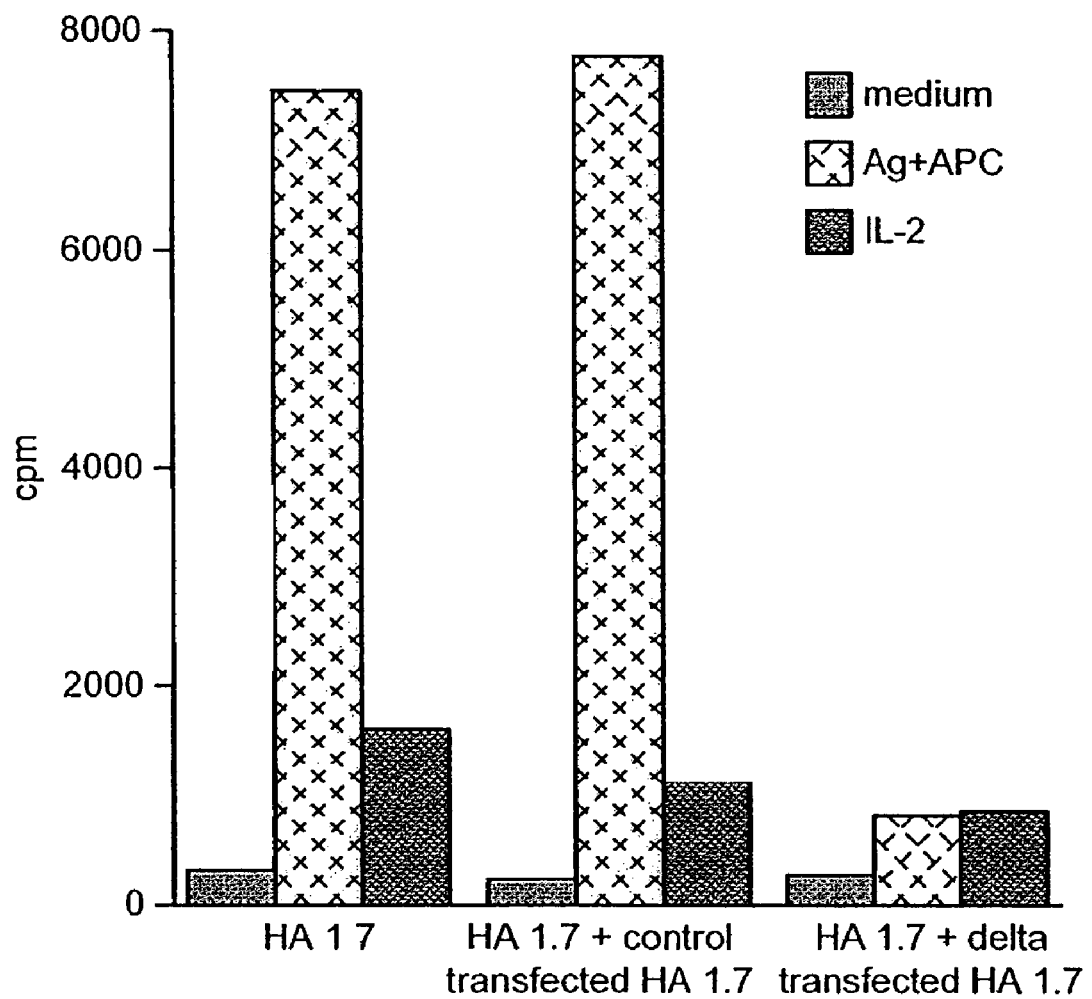
FIG. 5 shows the results of the experiment described in Example 7.
Figure 6:
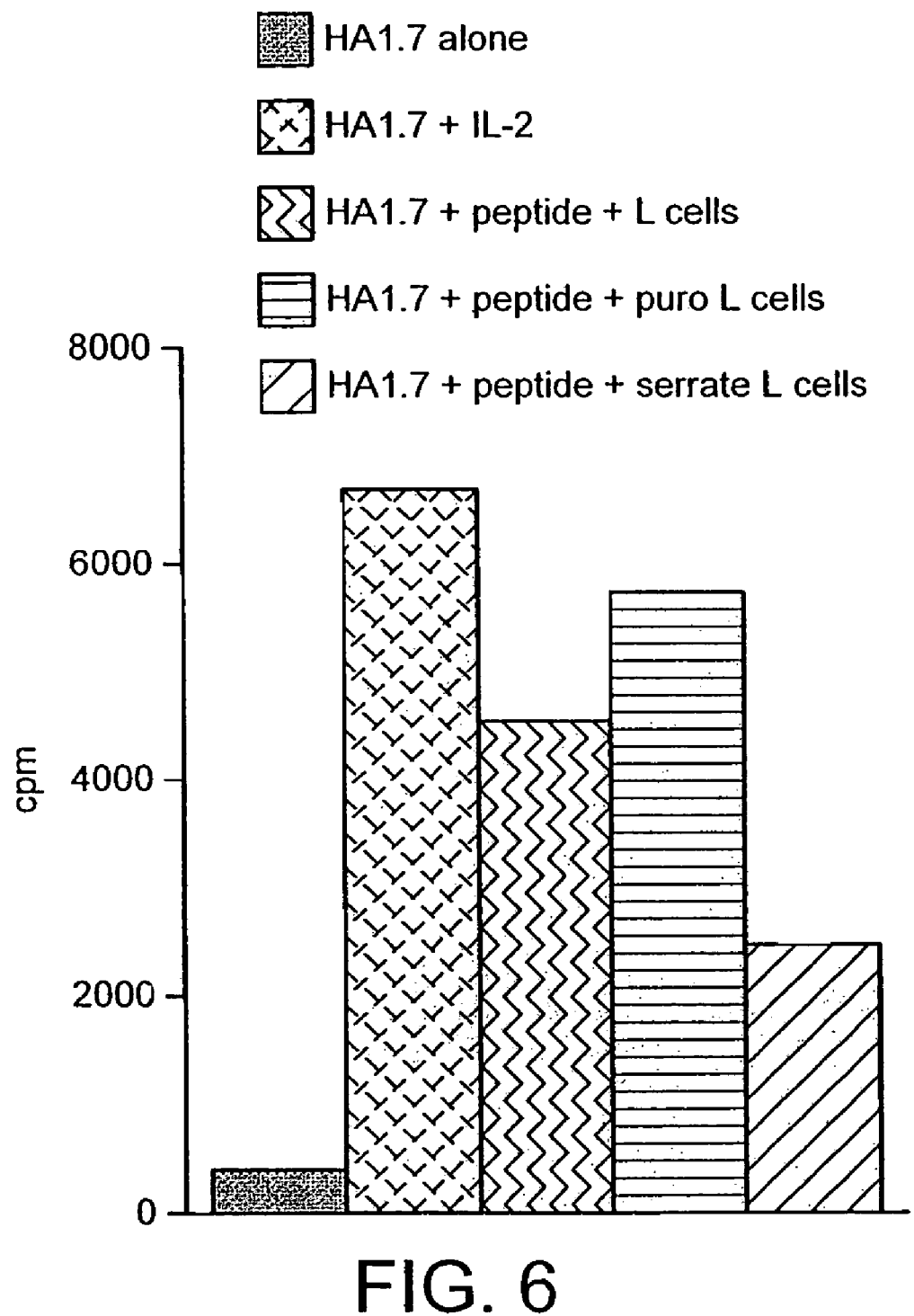
FIG. 6 shows the results of the experiment described in Example 8.
Figure 7:
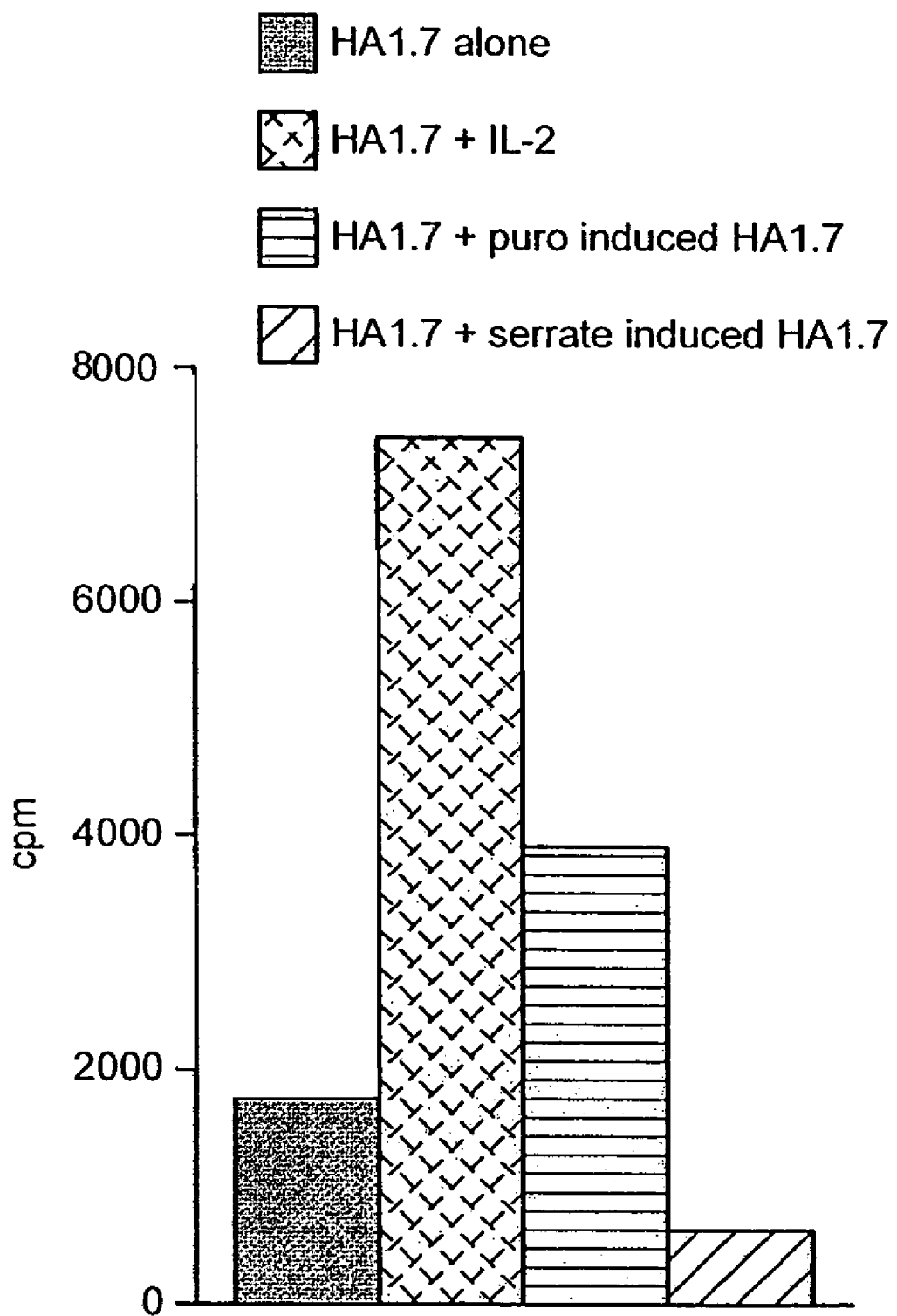
FIG. 7 shows the results of the experiment described in Example 9.

Cells were harvested after 68 hours with the addition of tritiated thymidine for the final 8 hours. The results are shown in FIG. 5.

Results: Following culture alone or with control virus transfected HA1.7, untreated HA1.7 responds well to peptide+antigen presenting cells. Incubation with Delta transfected irradiated HA1.7 completely prevents the response of untreated HA1.7 to antigen+APC. However, such cells respond as well as untreated or control virus incubated HA1.7 to IL-2, indicating that they are not simply unable to proliferate (FIG. 5).

EXAMPLE 8

Serrate Expression by Antigen Presenting Cells Prevents T Cell Responses

Clone HA1.7 was mixed with peptide HA306-318 (1.0 microgram/ml) in the presence of L cells expressing HLA-DRB1*0101(as antigen presenting cells), using $2\times10^4$ of each cell type. The L cells were transfected with either control (puro) or serrate (serrate L cells) expressing retrovirus. The proliferative response was measured after 72 hours following addition of tritiated thymidine for the last 8 hours of culture. Results are shown in FIG. 6 for HA1.7 cultures:

a) alone b) +IL-2 c) +peptide +DRB1*0101-L cells d) +peptide +DRB1*0101-L cells transfected with control virus e) +peptide +DRB1*0101-L cells transfected with serrate virus Results: HA1.7 stimulated by serrate expressing L cells responded poorly to antigen when compared with those stimulated by control transfected L cells (FIG. 6).

EXAMPLE 9

Serrate Expressing Antigen Presenting Cells Induce Regulatory T Cells

Clone HA1.7 was mixed with peptide HA306-318 and L cells (expressing DRB1*0101 as antigen presenting cells) in the presence of 2% IL-2. The L cells were transfected with either control or serrate expressing retrovirus. After 7 days in culture, the HA1.7 were harvested washed and irradiated before being mixed with fresh HA1.7 (using $2\times10^4$ each population). Cells were cultured for a further 2 days before being stimulated with peptide (1.0 microgram/ml)+normal antigen presenting cells (DRB1*0101 PBMCs). The proliferative response was measured after 72 hours following addition of tritiated thymidine for the last 8 hours of culture. The results are shown in FIG. 7 for fresh HA1.7 cultured:

a) alone b) +IL-2 c) +control virus induced HA1.7, then peptide +DRB1*0101 PBMC d) +serrate virus induced HA1.7, then peptide +DRB1*0101 PBMC Results: HA1.7 induced by serrate expressing L cells (Serrate induced HA1.7) prevented the response of normal HA1.7 to a normal antigenic stimulus (FIG. 7). This shows the ability of cells tolerised by exposure to serrate, to pass on their tolerance to a naive cell population (infectious/bystander tolerance).

EXAMPLE 10

The Regulation Induced by Delta Expressing T Cells is Antigen Specific

Mice were injected with $10^7$ T cell hybridoma cells transduced with either delta or control retrovirus. The hybridoma was 2BC3 which has specificity for peptide 110-131 of Der p 1. At the same time, animals received either Der p 1 or ovalbumin emulsified in complete Freund's adjuvant. 7 days later, lymph node cells were removed and $4\times10^5$ cells were cultured in the presence of Der p1 or ovalbumin (using the same antigen that they had already been immunised with).

The production of IL-2 was measured 24 hours after the start of culture. Stimulation indexes for IL-2 production are shown in FIGS. 8*a* (responses of animals immunised with Der p1) and 8b (responses of animals immunised with OVA) for animals injected with hybridomas transfected with control (puro) or Delta (delta) retrovirus.

Results: The response to Der p1 in animals injected with delta expressing 2BC3 hybridomas was virtually completely abolished whereas the response to ovalbumin was unaffected. These data are shown in FIGS. 8*a* and 8*b* where each dot represents the IL-2 production by an individual mouse to antigen as a stimulation index (SI) of control responses (no antigen added).

EXAMPLE 11

Delta is Expressed on T Cells During the Induction of Tolerance

HA1.7 was cultured in the presence of peptide HA306-318 (50 μg/ml) in the absence of APCs. Such conditions result in a state of tolerance in the HA1.7. After 0, 30, 120, 240 or 360 minutes, cells ($1.5\times10^6$) were harvested, pelleted and frozen. RNA was prepared from cell pellets by homogenisation in guanidium thiocyanate solution followed by CsCl density centrifugation. 1 μg RNA was converted into cDNA using an oligo dT primer. Of the resultant cDNA, 1/20th was used in PCR (40 cycles) using primers specific for the human delta homolog. PCR samples were analysed by gel electrophoresis (FIG. 9) wherein lane 1, marker, lane 2, t-0, lane 3, t=30 min, lane 4, t=120 min, lane 5, t=240 min, lane 6,t=360 min and lane 7 is the negative control.

Results.: Resting HA1.7 did not express Delta mRNA, but transcripts appeared within 2 hours of initiation of the tolerisation protocol.

EXAMPLE 12

Analysis of Notch 1, Serrate 1 and Delta 1 Expression During the Induction of Tolerance by Immunohistology and in Site Hybridisation C57 BL/6J mice were treated intranasally with either 100 microgram Der p1 peptide 110-131 or a control solution (phosphate buffered saline, PBS) on three consecutive days. Intranasal administration of antigen in this way is known to induce tolerance to the antigen. Some animals were then rested for 2 weeks before being rechallenged with antigen by injection of 50 μg Der p 1/CFA subcutaneously into the base of the tail. The superficial lymph nodes and spleens of animals were harvested at various time points thereafter (d0 being the first day of intranasal treatment or antigen rechallenge) and processed for immunohistology or in situ hybridisation. For immunohistology, tissues were frozen and 3 μm sections cut, fixed in ice cold acetone and stained with polyclonal antibodies specific for Notch 1 and Serrate 1. Bound antibody was detected using a horseradish peroxidase conjugated goat anti-rabbit antibody developed with diaminobenzidine as the substrate. Delta 1 specific antibodies were not available for the study. For in situ hybridisation, frozen tissues were sectioned and fixed in 4% paraformaldehyde. Sections were hybridised with digoxigenin coupled antisense RNA probes specific for Notch 1, Serrate 1 and Delta 1 at 65° C. Bound probe was detected by alkaline phosphatase conjugated goat anti-digoxigenin antibody developed using NBT and BCIP as the substrate. Data shown in tables 1 and 2 are for immunohistology and in situ hybridisation respectively. Data represent the analysis of tissues from 5 separate mice after intranasal peptide alone (PBS/p 110-131 primary) or intranasal and subcutaneous antigen (PBS/p110-131 rechallenge).

+ weak staining, ++ moderate staining, +++ stong staining.

Results:

Basal levels of Notch, Delta and Serrate are expressed in control mice receiving only PBS. Mice dosed intranasally with PBS and subcutaneously with antigen showed a moderate increase in expression of all three molecules within 8 days of rechallenge. Animals given either intranasal peptide alone or intranasal peptide followed by antigen rechallenge showed the same pattern of increased expression of Notch Delta and Serrate which was more rapid and greater than in control mice.

TABLE 1

Expression of Notch and Serrate proteins during the induction of tolerance

| treatment | day 0 | day 1 | day 4 | day 8 | day 12 |
|---|---|---|---|---|---|
| Notch 1 | | | | | |
| PBS primary | + | + | + | + | + |
| PBS rechallenge | + | + | + | +/++ | +/++ |
| p110-131 primary | + | + | ++ | +++ | +++ |
| p110-131 rechallenge | + | + | ++ | +++ | +++ |
| Serrate 1 | | | | | |
| PBS primary | + | + | + | + | + |
| PBS rechallenge | + | + | + | +/++ | +/++ |
| p110-131 primary | + | + | ++ | +++ | +++ |
| p110-131 rechallenge | + | + | ++ | +++ | +++ |

TABLE 2

Expression of Notch, Delta and Serrate transcripts during the induction of tolerance

| treatment | day 0 | day 1 | day 4 | day 8 | day 12 |
|---|---|---|---|---|---|
| Notch 1 | | | | | |
| PBS primary | + | + | + | + | + |
| PBS rechallenge | + | + | + | +/++ | +/++ |
| p110-131 primary | + | + | ++ | +++ | +++ |
| p110-131 rechallenge | + | + | ++ | +++ | +++ |
| Serrate 1 | | | | | |
| PBS primary | + | + | + | + | + |
| PBS rechallenge | + | + | + | +/++ | +/++ |
| p110-131 primary | + | + | ++ | +++ | +++ |
| p110-131 rechallenge | + | + | ++ | +++ | +++ |
| Delta 1 | | | | | |
| PBS primary | + | + | + | + | + |
| PBS rechallenge | + | + | + | +/++ | +/++ |
| p110-131 primary | + | + | ++ | +++ | +++ |
| p110-131 rechallenge | + | + | ++ | +++ | +++ |

Other modifications of the present invention will be apparent to those skilled in the present art.

The invention claimed is:

1. A method of reducing T-cell activation by administering a Notch ligand comprising a DSL domain to a patient in need thereof, wherein the Notch ligand is Serrate or Delta, wherein the Notch ligand interacts with a Notch receptor, thereby reducing T-cell activation, and wherein the T-cell activation occurs with autoimmune disease.

2. The method of claim 1, wherein the Notch ligand is Serrate.

3. The method of claim 1, wherein the Notch ligand is Delta.

4. The method of claim 1, wherein the Notch ligand is administered in the presence of an antigen.

5. The method of claim 1, wherein the Notch ligand is administered in a pharmaceutical composition.

* * * * *

SEQUENCE LISTING

<160> NUMBER OF SEQ ID NOS: 32

<210> SEQ ID NO 1
<211> LENGTH: 2892
<212> TYPE: DNA
<213> ORGANISM: Drosophila sp.

<400> SEQUENCE: 1

```
gaattcggag gaattattca aaacataaac acaataaaca atttgagtag ttgccgcaca      60
cacacacaca cacagcccgt ggattattac actaaaagcg acactcaatc caaaaaatca     120
gcaacaaaaa catcaataaa catgcattgg attaaatgtt tattaacagc attcatttgc     180
ttcacagtca tcgtgcaggt tcacagttcc ggcagctttg agttgcgcct gaagtacttc     240
agcaacgatc acgggcggga caacgagggt cgctgctgca gcggggagtc ggacggagcg     300
```

```
acgggcaagt gcctgggcag ctgcaagacg cggttttcgcg tctgcctaaa gcactaccag    360
gccaccatcg acaccacctc ccagtgcacc tacgggacg tgatcacgcc cattctcggc     420
gagaactcgg tcaatctgac cgacgcccag cgcttccaga caagggctt cacgaatccc     480 atccagttcc ccttctcgtt ctcatggccg ggtaccttct cgctgatcgt cgaggcctgg    540
catgatacga acaatagcgg caatgcgcga accaacaagc tcctcatcca gcgactcttg    600
gtgcagcagg tactggaggt gtcctccgaa tggaagacga caagtcgga atcgcagtac     660 acgtcgctgg agtacgattt ccgtgtcacc tgcgatctca actactacgg atccggctgt    720
gccaagttct gccggccccg cgacgattca tttggacact cgacttgctc ggagacgggc    780
gaaattatct gtttgaccgg atggcagggc gattactgtc acatacccaa atgcgccaaa    840
ggctgtgaac atggacattg cgacaaacgc aatcaatgcg tttgccaact gggctggaag    900
ggagccttgt gcaacgagtg cgttctggaa ccgaactgca tccatggcac ctgcaacaaa    960
ccctggactt gcatctgcaa cgagggttgg ggaggcttgt actgcaacca ggatctgaac   1020
tactgcacca accacagacc ctgcaagaat ggcggaacct gcttcaacac cggcgaggga   1080
ttgtacacat gcaaatgcgc tccaggatac agtggtgatg attgcgaaaa tgagatctac   1140
tcctgcgatg ccgatgtcaa tccctgccag aatggtggta cctgcatcga tgagccgcac   1200
acaaaaaccg gctacaagtg tcattgcgcc aacggctgga gcggaaagat gtgcgaggag   1260
aaagtgctca cgtgttcgga caaaccctgt catcagggaa tctgccgcaa cgttcgtcct   1320
ggcttgggaa gcaagggtca gggctaccag tgcgaatgtc ccattggcta cagcggaccc   1380
aactgcgatc tccagctgga caactgcagt ccgaatccat gcataaacgg tggaagctgt   1440
cagccgagcg gaaagtgtat ttgcccagcg ggatttttcgg gaacgagatg cgagaccaac   1500
attgacgatt gtcttggcca ccagtgcgag aacggaggca cctgcatagg tatggtcaac   1560
caatatcgct gccaatgcgt tcccggtttc catggcaccc actgtagtag caaagttgac   1620
ttgtgcctca tcagaccgtg tgccaatgga ggaacctgct tgaatctcaa caacgattac   1680
cagtgcacct gtcgtgcggg atttactggc aaggattgct ctgtggacat cgatgagtgc   1740
agcagtggac cctgtcataa cggcggcact tgcatgaacc gcgtcaattc gttcgaatgc   1800
gtgtgtgcca atggtttcag gggcaagcag tgcgatgagg agtcctacga ttcggtgacc   1860
ttcgatgccc accaatatgg agcgaccaca caagcgagag ccgatggttt gaccaatgcc   1920
caggtagtcc taattgctgt tttctccgtt gcgatgcctt tggtggcggt tattgcggcg   1980
tgcgtggtct tctgcatgaa gcgcaagcgt aagcgtgctc aggaaaagga cgacgcggag   2040
gccaggaagc agaacgaaca gaatgcggtg gccacaatgc atcacaatgg cagtggggtg   2100
ggtgtagctt tggcttcagc ctctctgggc ggcaaaactg gcagcaacag cggtctcacc   2160
ttcgatggcg gcaacccgaa tatcatcaaa acacctggg acaagtcggt caacaacatt   2220
tgtgcctcag cagcagcagc ggcggcgcg gcagcagcgg cggacgagtg tctcatgtac   2280
ggcggatatg tggcctcggt ggcggataac aacaatgcca actcatactt ttgtgtggct   2340
ccgctacaaa gagccaagtc gcaaaagcaa ctcaacaccg atcccacgct catgcaccgc   2400
ggttcgccgg caggcagctc agccaaggga gcgtctggcg gaggaccggg agcggcggag   2460
ggcaagagga tctctgtttt aggcgagggt tcctactgta gccagcgttg gcctcgttg    2520 gcggcggcg gagtggccgg agcctgttca tcccagctaa tggctgcagc ttcggcagcg   2580
ggcagcggag cggggacggc gcaacagcag cgatccgtgg tctgcggcac tccgcatatg   2640
taactccaaa aatccggaag ggctcctggt aaatccggag aaatccgcat ggaggagctg   2700
```

-continued

```
acagcacata cacaaagaaa agactgggtt gggttcaaaa tgtgagagag acgccaaaat    2760
gttgttgttg attgaagcag tttagtcgtc acgaaaaatg aaaaatctgt aacaggcata    2820
actcgtaaac tccctaaaaa atttgtatag taattagcaa agctgtgacc cagccgtttc    2880
gatcccgaat tc                                                        2892
```

<210> SEQ ID NO 2
<211> LENGTH: 833
<212> TYPE: PRT
<213> ORGANISM: Drosophila sp.

<400> SEQUENCE: 2

| Met<br>1 | His | Trp | Ile | Lys<br>5 | Cys | Leu | Leu | Thr | Ala<br>10 | Phe | Ile | Cys | Phe | Thr<br>15 | Val |
|---|---|---|---|---|---|---|---|---|---|---|---|---|---|---|---|

Ile Val Gln Val His Ser Ser Gly Ser Phe Glu Leu Arg Leu Lys Tyr
            20                  25                  30

Phe Ser Asn Asp His Gly Arg Asp Asn Glu Gly Arg Cys Cys Ser Gly
        35                  40                  45

Glu Ser Asp Gly Ala Thr Gly Lys Cys Leu Gly Ser Cys Lys Thr Arg
    50                  55                  60

Phe Arg Val Cys Leu Lys His Tyr Gln Ala Thr Ile Asp Thr Thr Ser
65                  70                  75                  80

Gln Cys Thr Tyr Gly Asp Val Ile Thr Pro Ile Leu Gly Glu Asn Ser
                85                  90                  95

Val Asn Leu Thr Asp Ala Gln Arg Phe Gln Asn Lys Gly Phe Thr Asn
            100                 105                 110

Pro Ile Gln Phe Pro Phe Ser Phe Ser Trp Pro Gly Thr Phe Ser Leu
        115                 120                 125

Ile Val Glu Ala Trp His Asp Thr Asn Asn Ser Gly Asn Ala Arg Thr
    130                 135                 140

Asn Lys Leu Leu Ile Gln Arg Leu Leu Val Gln Val Leu Glu Val
145                 150                 155                 160

Ser Ser Glu Trp Lys Thr Asn Lys Ser Glu Ser Gln Tyr Thr Ser Leu
                165                 170                 175

Glu Tyr Asp Phe Arg Val Thr Cys Asp Leu Asn Tyr Tyr Gly Ser Gly
            180                 185                 190

Cys Ala Lys Phe Cys Arg Pro Arg Asp Asp Ser Phe Gly His Ser Thr
        195                 200                 205

Cys Ser Glu Thr Gly Glu Ile Ile Cys Leu Thr Gly Trp Gln Gly Asp
    210                 215                 220

Tyr Cys His Ile Pro Lys Cys Ala Lys Gly Cys Glu His Gly His Cys
225                 230                 235                 240

Asp Lys Arg Asn Gln Cys Val Cys Gln Leu Gly Trp Lys Gly Ala Leu
                245                 250                 255

Cys Asn Glu Cys Val Leu Glu Pro Asn Cys Ile His Gly Thr Cys Asn
            260                 265                 270

Lys Pro Trp Thr Cys Ile Cys Asn Glu Gly Trp Gly Gly Leu Tyr Cys
        275                 280                 285

Asn Gln Asp Leu Asn Tyr Cys Thr Asn His Arg Pro Cys Lys Asn Gly
    290                 295                 300

Gly Thr Cys Phe Asn Thr Gly Glu Gly Leu Tyr Thr Cys Lys Cys Ala
305                 310                 315                 320

Pro Gly Tyr Ser Gly Asp Asp Cys Glu Asn Glu Ile Tyr Ser Cys Asp
                325                 330                 335

-continued

```
Ala Asp Val Asn Pro Cys Gln Asn Gly Gly Thr Cys Ile Asp Glu Pro
            340                 345                 350
His Thr Lys Thr Gly Tyr Lys Cys His Cys Ala Asn Gly Trp Ser Gly
            355                 360                 365
Lys Met Cys Glu Glu Lys Val Leu Thr Cys Ser Asp Lys Pro Cys His
            370                 375                 380
Gln Gly Ile Cys Arg Asn Val Arg Pro Gly Leu Gly Ser Lys Gly Gln
385                 390                 395                 400
Gly Tyr Gln Cys Glu Cys Pro Ile Gly Tyr Ser Gly Pro Asn Cys Asp
                405                 410                 415
Leu Gln Leu Asp Asn Cys Ser Pro Asn Pro Cys Ile Asn Gly Gly Ser
            420                 425                 430
Cys Gln Pro Ser Gly Lys Cys Ile Cys Pro Ala Gly Phe Ser Gly Thr
            435                 440                 445
Arg Cys Glu Thr Asn Ile Asp Asp Cys Leu Gly His Gln Cys Glu Asn
            450                 455                 460
Gly Gly Thr Cys Ile Asp Met Val Asn Gln Tyr Arg Cys Gln Cys Val
465                 470                 475                 480
Pro Gly Phe His Gly Thr His Cys Ser Ser Lys Val Asp Leu Cys Leu
                485                 490                 495
Ile Arg Pro Cys Ala Asn Gly Gly Thr Cys Leu Asn Leu Asn Asn Asp
            500                 505                 510
Tyr Gln Cys Thr Cys Arg Ala Gly Phe Thr Gly Lys Asp Cys Ser Val
            515                 520                 525
Asp Ile Asp Glu Cys Ser Ser Gly Pro Cys His Asn Gly Gly Thr Cys
            530                 535                 540
Met Asn Arg Val Asn Ser Phe Glu Cys Val Cys Ala Asn Gly Phe Arg
545                 550                 555                 560
Gly Lys Gln Cys Asp Glu Glu Ser Tyr Asp Ser Val Thr Phe Asp Ala
                565                 570                 575
His Gln Tyr Gly Ala Thr Thr Gln Ala Arg Ala Asp Gly Leu Thr Asn
            580                 585                 590
Ala Gln Val Val Leu Ile Ala Val Phe Ser Val Ala Met Pro Leu Val
            595                 600                 605
Ala Val Ile Ala Ala Cys Val Val Phe Cys Met Lys Arg Lys Arg Lys
            610                 615                 620
Arg Ala Gln Glu Lys Asp Asp Ala Glu Ala Arg Lys Gln Asn Glu Gln
625                 630                 635                 640
Asn Ala Val Ala Thr Met His His Asn Gly Ser Gly Val Gly Val Ala
            645                 650                 655
Leu Ala Ser Ala Ser Leu Gly Gly Lys Thr Gly Ser Asn Ser Gly Leu
            660                 665                 670
Thr Phe Asp Gly Gly Asn Pro Asn Ile Ile Lys Asn Thr Trp Asp Lys
            675                 680                 685
Ser Val Asn Asn Ile Cys Ala Ser Ala Ala Ala Ala Ala Ala Ala Ala
            690                 695                 700
Ala Ala Ala Asp Glu Cys Leu Met Tyr Gly Gly Tyr Val Ala Ser Val
705                 710                 715                 720
Ala Asp Asn Asn Ala Asn Ser Tyr Phe Cys Val Ala Pro Leu Gln
                725                 730                 735
Arg Ala Lys Ser Gln Lys Gln Leu Asn Thr Asp Pro Thr Leu Met His
            740                 745                 750
```

```
Arg Gly Ser Pro Ala Gly Ser Ser Ala Lys Gly Ala Ser Gly Gly
        755                 760                 765

Pro Gly Ala Ala Glu Gly Lys Arg Ile Ser Val Leu Gly Glu Gly Ser
        770                 775                 780

Tyr Cys Ser Gln Arg Trp Pro Ser Leu Ala Ala Ala Gly Val Ala Gly
785                 790                 795                 800

Ala Cys Ser Ser Gln Leu Met Ala Ala Ser Ala Ala Gly Ser Gly
                805                 810                 815

Ala Gly Thr Ala Gln Gln Gln Arg Ser Val Val Cys Gly Thr Pro His
        820                 825                 830

Met
```

<210> SEQ ID NO 3
<211> LENGTH: 6464
<212> TYPE: DNA
<213> ORGANISM: Homo sapiens

<400> SEQUENCE: 3

```
gaattcccct ccccccttttt tccatgcagc tgatctaaaa gggaataaaa ggctgcgcat    60
aatcataata ataaaagaag gggagcgcga gagaaggaaa gaaagccggg aggtggaaga   120
ggaggggggag cgtctcaaag aagcgatcag aataataaaa ggaggccggg ctctttgcct   180
tctggaacgg gccgctcttg aaagggcttt tgaaaagtgg tgttgttttc cagtcgtgca   240
tgctccaatc ggcggagtat attagagccg gacgcggcc gcaggggcag cggcgacggc    300
agcaccggcg gcagcaccag cgcgaacagc agcggcggcg tcccgagtgc ccgcggcggc   360
gcgcgcagcg atgcgttccc cacggacacg cggccggtcc gggcgccccc taagcctcct   420
gctcgccctg ctctgtgccc tgcgagccaa ggtgtgtggg gcctcgggtc agttcgagtt   480
ggagatcctg tccatgcaga acgtgaacgg ggagctgcag aacgggaact gctgcggcgg   540
cgcccggaac ccgggagacc gcaagtgcac ccgcgacgtg tgtgacacat acttcaaagt   600
gtgcctcaag gagtatcagt cccgcgtcac ggccgggggg ccctgcagct tcggctcagg   660
gtccacgcct gtcatcgggg gcaacacctt caacctcaag gccagccgcg caacgacccc  720
gaaccgcatc gtgctgcctt tcagtttcgc ctggccgagg tcctatacgt tgcttgtgga   780
ggcgtgggat tccagtaatg acaccgttca acctgacagt attattgaaa aggcttctca   840
ctcgggcatg atcaaccca gccggcagtg gcagacgctg aagcagaaca cgggcgttgc   900
ccactttgag tatcagatcc gcgtgacctg tgatgactac tactatgct ttggctgtaa   960
taagttctgc cgccccagag atgacttctt tggacactat gcctgtgacc agaatggcaa  1020
caaaacttgc atggaaggct ggatgggccc cgaatgtaac agagctattt gccgacaagg  1080
ctgcagtcct aagcatgggt cttgcaaact cccaggtgac tgcaggtgcc agtacggctg  1140
gcaaggcctg tactgtgata agtgcatccc acacccggga tgcgtccacg gcatctgtaa  1200
tgagccctgg cagtgcctct gtgagaccaa ctggggcggc cagctctgtg acaaagatct  1260
caattactgt gggactcatc agccgtgtct caacggggga acttgtagca acacaggccc  1320
tgacaaatat cagtgttcct gccctgaggg gtattcagga cccaactgtg aaattgctga  1380
gcacgcctgc ctctctgatc cctgtcacaa cagaggcagc tgtaaggaga cctccctggg  1440
ctttgagtgt gagtgttccc caggctggac cggccccaca tgctctacaa acattgatga  1500
ctgttctcct aataactgtt cccacggggg cacctgccag gacctggtta acggatttaa  1560
gtgtgtgtgc cccccacagt ggactgggaa aacgtgccag ttagatgcaa atgaatgtga  1620
```

```
ggccaaacct tgtgtaaacg ccaaatcctg taagaatctc attgccagct actactgcga    1680
ctgtcttccc ggctggatgg gtcagaattg tgacataaat attaatgact gccttggcca    1740
gtgtcagaat gacgcctcct gtcgggattt ggttaatggt tatcgctgta tctgtccacc    1800
tggctatgca ggcgatcact gtgagagaga catcgatgaa tgtgccagca acccctgttt    1860 gaatggggt cactgtcaga atgaaatcaa cagattccag tgtctgtgtc ccactggttt     1920
ctctggaaac ctctgtcagc tggacatcga ttattgtgag cctaatccct gccagaacgg    1980
tgcccagtgc tacaaccgtg ccagtgacta tttctgcaag tgccccgagg actatgaggg    2040
caagaactgc tcacacctga agaccactg ccgcacgacc ccctgtgaag tgattgacag      2100
ctgcacagtg gccatggctt ccaacgacac acctgaaggg gtgcggtata tttcctccaa    2160
cgtctgtggt cctcacggga agtgcaagag tcagtcggga ggcaaattca cctgtgactg    2220
taacaaaggc ttcacgggaa catactgcca tgaaaatatt aatgactgtg agagcaaccc    2280
ttgtagaaac ggtggcactt gcatcgatgg tgtcaactcc tacaagtgca tctgtagtga    2340
cggctgggag ggggcctact gtgaaaccaa tattaatgac tgcagccaga acccctgcca    2400 caatggggc acgtgtcgcg acctggtcaa tgacttctac tgtgactgta aaaatgggtg     2460
gaaaggaaag acctgccact cacgtgacag tcagtgtgat gaggccacgt gcaacaacgg    2520
tggcacctgc tatgatgagg gggatgcttt taagtgcatg tgtcctggcg ctgggaagg     2580 aacaacctgt aacatagccc gaaacagtag ctgcctgccc aaccccctgcc ataatggggg   2640 cacatgtgtg gtcaacggcg agtccttac gtgcgtctgc aaggaaggct gggaggggcc     2700
catctgtgct cagaatacca atgactgcag ccctcatccc tgttacaaca gcggcacctg    2760
tgtggatgga caactggt accggtgcga atgtgccccg ggttttgctg ggcccgactg       2820
cagaataaac atcaatgaat gccagtcttc accttgtgcc tttggagcga cctgtgtgga    2880
tgagatcaat ggctaccggt gtgtctgccc tccagggcac agtggtgcca agtgccagga    2940
agtttcaggg agaccttgca tcaccatggg gagtgtgata ccagatgggg ccaaatggga    3000
tgatgactgt aatacctgcc agtgcctgaa tggacggatc gcctgctcaa aggtctggtg    3060
tggccctcga ccttgcctgc tccacaaagg gcacagcgag tgccccagcg ggcagagctg    3120
catccccatc ctggacgacc agtgcttcgt ccacccctgc actggtgtgg gcgagtgtcg    3180
gtcttccagt ctccagccgg tgaagacaaa gtgcacctct gactcctatt accaggataa    3240
ctgtgcgaac atcacattta cctttaacaa ggagatgatg tcaccaggtc ttactacgga    3300
gcacatttgc agtgaattga ggaatttgaa tattttgaag aatgtttccg ctgaatattc    3360
aatctacatc gcttgcgagc cttccccttc agcgaacaat gaaatacatg tggccatttc    3420
tgctgaagat atacgggatg atgggaaccc gatcaaggaa atcactgaca aaataatcga    3480
tcttgttact aaacgtgatg gaaacagctc gctgattgct gccgttgaag aagtaagagt    3540
tcagaggcgg cctctgaaga acagaacaga tttccttgtt cccttgctga gctctgtctt    3600
aactgtggct tggatctgtt gcttggtgac ggccttctac tggtgcctgc ggaagcggcg    3660
gaagccgggc agccacacac actcagcctc tgaggacaac accaccaaca acgtgcggga    3720
gcagctgaac cagatcaaaa accccattga gaaacatggg gccaacacgg tcccatcaa     3780 ggattacgag aacaagaact ccaaaatgtc taaaataagg acacacaatt ctgaagtaga    3840
agaggacgac atggacaaac accagcagaa agcccggttt gccaagcagc ggcgtacac     3900 gctggtagac agagaagaga agcccccccaa cggcacgccg acaaaacacc caaactggac    3960
aaacaaacag gacaacagag acttggaaag tgcccagagc ttaaaccgaa tggagtacat    4020
```

```
cgtatagcag accgcgggca ctgccgccgc taggtagagt ctgagggctt gtagttcttt    4080
aaactgtcgt gtcatactcg agtctgaggc cgttgctgac ttagaatccc tgtgttaatt    4140
tagtttgaca agctggctta cactggcaat ggtagttctg tggttggctg ggaaatcgag    4200
tggcgcatct cacagctatg caaaaagcta gtcaacagta cccctggttg tgtgtcccct    4260
tgcagccgac acggtctcgg atcaggctcc caggagctgc ccagcccct ggtactttga     4320
gctcccactt ctgccagatg tctaatggtg atgcagtctt agatcatagt tttatttata    4380
tttattgact cttgagttgt ttttgtatat tggttttatg atgacgtaca agtagttctg    4440
tatttgaaag tgcctttgca gctcagaacc acagcaacga tcacaaatga ctttattatt    4500
tatttttttt aattgtattt ttgttgttgg gggaggggag actttgatgt cagcagttgc    4560
tggtaaaatg aagaatttaa agaaaaaatg tccaaaagta gaactttgta tagttatgta    4620
aataattctt ttttattaat cactgtgtat atttgattta ttaacttaat aatcaagagc    4680
cttaaaacat cattccttt tatttatatg tatgtgttta gaattgaagg ttttgatag      4740
cattgtaagc gtatggcttt atttttttga actcttctca ttacttgttg cctataagcc    4800
aaaaaggaaa gggtgttttg aaaatagttt attttaaaac aataggatgg gctacacgta    4860
cataggtaaa taatagcacc gtactggtta tgatgatgaa ataactgga aacttgaaag     4920
cttgtggtaa tggcagataa agatggttca cctgggaaat taaaacttga atggttgtac    4980
agaaaagcac agagtggaat gcacatcaat gacagtaagg gagttagttc taggaacagc    5040
tcctgaacag taagattccc gcaatagtct ccgcctcgtt cgtctatggt atgcatccca    5100
ttcattttct tcttctgatt attgtcatct ttccctttgc caaatgggca gttattgttt    5160
cagggagaga agctgctcat tggccaatca ttctggtgtg cagtgctcca tcggattcta    5220
catgtccaac aaggcatgtc tggatgatgc aatgtctgtc tgaccccgg aattccgtgc     5280
agagacaaca ttctagacag atatacactt tttattatta acaaactttg ccacaacct     5340
ttgatgtata aattgccgga tttccccagt cctttcattg tggctttgga caggagcagg    5400
ctcacttgtc tgcttcaggc tgcctttctc ttgggttgca cctcagttct tacttattta    5460
tttatttttga gtggagcata ggggcctctt ccaaaatggg tagagctcag gggctttctt    5520
attgaaatgg tcacatgata aaaacgggct gaaaaggag agttccagga gaaaagccca     5580
gaaaaggccc ctcctcagaa gacagccttt aagcctcttg cttactgaag gaagccccac    5640
cttctagcac tgaggccggg tctgatcttc cagaggagtt ggaggagtcc atgagaatgg    5700
ccaccattct tgcttgctgc tgctgatgtt gcagttttga gagaacagcg ggatccttgt    5760
tgtcctctag agacttgagt ctgtcactga cattttttca gttcctttgc tcatagacca    5820
tacgaggaat tagtgatgtg tcagttgaga gttcacaatc tcattgttca tttaattcac    5880
tttaaagttg tcaatttctg tgtgagtaac ctgtaaaaga cacctttcca gaaagagtttt   5940
gccgtctgtt tgaaaaaaaa atctttataa actttcctaa gtatctggat ttggattcct    6000
tatttggaga gaaaatgtac cctgtctcca ccaaaaatac aaaaattagc caggcttggt    6060
ggtgcacacc ggtaatccca gcaactctgg agactaaggc aggaagaatc gcttgaccca    6120
ggagggtcga ggctacaatg agttgaaacc gcgccactgc actccagcct gggcgacagt    6180
gcgaggccct gtctcaaaaa taaaataaaa taaataaata aattagccag atactgtgtg    6240
cacgcctgca gtcccagcta ttctggaagc tgaggtggga agatggttaa gcctgagagg    6300
acaaagctgc agtgagtcat gtttgcatca ctgcactcca gcctgggtga cagagcaaga    6360
```

```
cctgtctaa aaaacaaaaa caggccgggt gtggtggctc atgcctgcca tcccagtgct    6420
ttgggaggca gaggttggca taatcccagc gctctgggaa ttcc                   6464
```

<210> SEQ ID NO 4
<211> LENGTH: 1218
<212> TYPE: PRT
<213> ORGANISM: Homo sapiens

<400> SEQUENCE: 4

```
Met Arg Ser Pro Arg Thr Arg Gly Arg Ser Gly Arg Pro Leu Ser Leu
1               5                   10                  15

Leu Leu Ala Leu Leu Cys Ala Leu Arg Ala Lys Val Cys Gly Ala Ser
                20                  25                  30

Gly Gln Phe Glu Leu Glu Ile Leu Ser Met Gln Asn Val Asn Gly Glu
            35                  40                  45

Leu Gln Asn Gly Asn Cys Cys Gly Gly Ala Arg Asn Pro Gly Asp Arg
        50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Pro Asn Arg Ile Val Leu Pro Phe Ser Phe Ala Trp
        115                 120                 125

Pro Arg Ser Tyr Thr Leu Leu Val Glu Ala Trp Asp Ser Ser Asn Asp
130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                165                 170                 175

Ala His Phe Glu Tyr Gln Ile Arg Val Thr Cys Asp Asp Tyr Tyr Tyr
            180                 185                 190

Gly Phe Gly Cys Asn Lys Phe Cys Arg Pro Arg Asp Asp Phe Phe Gly
        195                 200                 205

His Tyr Ala Cys Asp Gln Asn Gly Asn Lys Thr Cys Met Glu Gly Trp
210                 215                 220

Met Gly Pro Glu Cys Asn Arg Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Ile Cys Asn Glu Pro Trp Gln Cys Leu Cys Glu Thr Asn Trp
        275                 280                 285

Gly Gly Gln Leu Cys Asp Lys Asp Leu Asn Tyr Cys Gly Thr His Gln
    290                 295                 300

Pro Cys Leu Asn Gly Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
            340                 345                 350

Glu Thr Ser Leu Gly Phe Glu Cys Glu Cys Ser Pro Gly Trp Thr Gly
```

-continued

```
                355                 360                 365
Pro Thr Cys Ser Thr Asn Ile Asp Asp Cys Ser Pro Asn Asn Cys Ser
    370                 375                 380
His Gly Gly Thr Cys Gln Asp Leu Val Asn Gly Phe Lys Cys Val Cys
385                 390                 395                 400
Pro Pro Gln Trp Thr Gly Lys Thr Cys Gln Leu Asp Ala Asn Glu Cys
                405                 410                 415
Glu Ala Lys Pro Cys Val Asn Ala Lys Ser Cys Lys Asn Leu Ile Ala
                420                 425                 430
Ser Tyr Tyr Cys Asp Cys Leu Pro Gly Trp Met Gly Gln Asn Cys Asp
                435                 440                 445
Ile Asn Ile Asn Asp Cys Leu Gly Gln Cys Gln Asn Asp Ala Ser Cys
    450                 455                 460
Arg Asp Leu Val Asn Gly Tyr Arg Cys Ile Cys Pro Pro Gly Tyr Ala
465                 470                 475                 480
Gly Asp His Cys Glu Arg Asp Ile Asp Glu Cys Ala Ser Asn Pro Cys
                485                 490                 495
Leu Asn Gly Gly His Cys Gln Asn Glu Ile Asn Arg Phe Gln Cys Leu
                500                 505                 510
Cys Pro Thr Gly Phe Ser Gly Asn Leu Cys Gln Leu Asp Ile Asp Tyr
    515                 520                 525
Cys Glu Pro Asn Pro Cys Gln Asn Gly Ala Gln Cys Tyr Asn Arg Ala
    530                 535                 540
Ser Asp Tyr Phe Cys Lys Cys Pro Glu Asp Tyr Glu Gly Lys Asn Cys
545                 550                 555                 560
Ser His Leu Lys Asp His Cys Arg Thr Thr Pro Cys Glu Val Ile Asp
                565                 570                 575
Ser Cys Thr Val Ala Met Ala Ser Asn Asp Thr Pro Glu Gly Val Arg
                580                 585                 590
Tyr Ile Ser Ser Asn Val Cys Gly Pro His Gly Lys Cys Lys Ser Gln
                595                 600                 605
Ser Gly Gly Lys Phe Thr Cys Asp Cys Asn Lys Gly Phe Thr Gly Thr
    610                 615                 620
Tyr Cys His Glu Asn Ile Asn Asp Cys Glu Ser Asn Pro Cys Arg Asn
625                 630                 635                 640
Gly Gly Thr Cys Ile Asp Gly Val Asn Ser Tyr Lys Cys Ile Cys Ser
                645                 650                 655
Asp Gly Trp Glu Gly Ala Tyr Cys Glu Thr Asn Ile Asn Asp Cys Ser
                660                 665                 670
Gln Asn Pro Cys His Asn Gly Gly Thr Cys Arg Asp Leu Val Asn Asp
                675                 680                 685
Phe Tyr Cys Asp Cys Lys Asn Gly Trp Lys Gly Lys Thr Cys His Ser
    690                 695                 700
Arg Asp Ser Gln Cys Asp Glu Ala Thr Cys Asn Asn Gly Gly Thr Cys
705                 710                 715                 720
Tyr Asp Glu Gly Asp Ala Phe Lys Cys Met Cys Pro Gly Gly Trp Glu
                725                 730                 735
Gly Thr Thr Cys Asn Ile Ala Arg Asn Ser Ser Cys Leu Pro Asn Pro
                740                 745                 750
Cys His Asn Gly Gly Thr Cys Val Val Asn Gly Glu Ser Phe Thr Cys
                755                 760                 765
Val Cys Lys Glu Gly Trp Glu Gly Pro Ile Cys Ala Gln Asn Thr Asn
    770                 775                 780
```

-continued

```
Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
                805                 810                 815

Cys Arg Ile Asn Ile Asn Glu Cys Gln Ser Ser Pro Cys Ala Phe Gly
            820                 825                 830

Ala Thr Cys Val Asp Glu Ile Asn Gly Tyr Arg Cys Val Cys Pro Pro
        835                 840                 845

Gly His Ser Gly Ala Lys Cys Gln Glu Val Ser Gly Arg Pro Cys Ile
    850                 855                 860

Thr Met Gly Ser Val Ile Pro Asp Gly Ala Lys Trp Asp Asp Asp Cys
865                 870                 875                 880

Asn Thr Cys Gln Cys Leu Asn Gly Arg Ile Ala Cys Ser Lys Val Trp
                885                 890                 895

Cys Gly Pro Arg Pro Cys Leu Leu His Lys Gly His Ser Glu Cys Pro
            900                 905                 910

Ser Gly Gln Ser Cys Ile Pro Ile Leu Asp Asp Gln Cys Phe Val His
        915                 920                 925

Pro Cys Thr Gly Val Gly Glu Cys Arg Ser Ser Ser Leu Gln Pro Val
    930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr
                965                 970                 975

Glu His Ile Cys Ser Glu Leu Arg Asn Leu Asn Ile Leu Lys Asn Val
            980                 985                 990

Ser Ala Glu Tyr Ser Ile Tyr Ile Ala Cys Glu Pro Ser Pro Ser Ala
        995                 1000                1005

Asn Asn Glu Ile His Val Ala Ile Ser Ala Glu Asp Ile Arg Asp
    1010                1015                1020

Asp Gly Asn Pro Ile Lys Glu Ile Thr Asp Lys Ile Ile Asp Leu
    1025                1030                1035

Val Thr Lys Arg Asp Gly Asn Ser Ser Leu Ile Ala Ala Val Glu
    1040                1045                1050

Glu Val Arg Val Gln Arg Arg Pro Leu Lys Asn Arg Thr Asp Phe
    1055                1060                1065

Leu Val Pro Leu Leu Ser Ser Val Leu Thr Val Ala Trp Ile Cys
    1070                1075                1080

Cys Leu Val Thr Ala Phe Tyr Trp Cys Leu Arg Lys Arg Arg Lys
    1085                1090                1095

Pro Gly Ser His Thr His Ser Ala Ser Glu Asp Asn Thr Thr Asn
    1100                1105                1110

Asn Val Arg Glu Gln Leu Asn Gln Ile Lys Asn Pro Ile Glu Lys
    1115                1120                1125

His Gly Ala Asn Thr Val Pro Ile Lys Asp Tyr Glu Asn Lys Asn
    1130                1135                1140

Ser Lys Met Ser Lys Ile Arg Thr His Asn Ser Glu Val Glu Glu
    1145                1150                1155

Asp Asp Met Asp Lys His Gln Gln Lys Ala Arg Phe Ala Lys Gln
    1160                1165                1170

Pro Ala Tyr Thr Leu Val Asp Arg Glu Glu Lys Pro Pro Asn Gly
    1175                1180                1185
```

```
Thr Pro Thr Lys His Pro Asn Trp Thr Asn Lys Gln Asp Asn Arg
    1190            1195                1200

Asp Leu Glu Ser Ala Gln Ser Leu Asn Arg Met Glu Tyr Ile Val
    1205            1210                1215

<210> SEQ ID NO 5
<211> LENGTH: 4483
<212> TYPE: DNA
<213> ORGANISM: Homo sapiens

<400> SEQUENCE: 5
```

| | | | | | |
|---|---|---|---|---|---|
| ggccggggcc | gggcgggcgg | gtcgcggggg | caatgcgggc | gcagggccgg | gggcgccttc | 60 |
| cccggcggct | gctgctgctg | ctggcgctct | gggtgcaggc | ggcgcggccc | atgggctatt | 120 |
| tcgagctgca | gctgagcgcg | ctgcggaacg | tgaacgggga | gctgctgagc | ggcgcctgct | 180 |
| gtgacggcga | cggccggaca | acgcgcgcgg | ggggctgcgg | ccacgacgag | tgcgacaccg | 240 |
| ctcctttacc | ctcatcgtgg | aggcctggga | ctgggacaac | gataccaccc | cgaatgagga | 300 |
| gctgctgatc | gagcgagtgt | cgcatgccgg | catgatcaac | ccggaggacc | gctggaagag | 360 |
| cctgcacttc | agcggccacg | tggcgcacct | ggagctgcag | atccgcgtgc | gctgcgacga | 420 |
| gaactactac | agcgccactt | gcaacaagtt | ctgccggccc | cgcaatgact | ttttcggcca | 480 |
| ctacacctgc | gaccagtacg | gcaacaaggc | ctgcatggac | ggctggatgg | gcaaggagtg | 540 |
| caaggaagct | gtgtgtaaac | aagggtgtaa | tttgctccac | gggggatgca | ccgtgcctgg | 600 |
| ggagtgcagg | tgcagctacg | gctggcaagg | gaggttctgc | gatgagtgtg | tcccctaccc | 660 |
| cggctgcgtg | catggcagtt | gtgtggagcc | ctggcagtgc | aactgtgaga | ccaactgggg | 720 |
| cggcctgctc | tgtgacaaag | acctgaacta | ctgtggcagc | caccaccct | gcaccaacgg | 780 |
| aggcacgtgc | atcaacgccg | agcctgacca | gtaccgctgc | acctgccctg | acggctactc | 840 |
| gggcaggaac | tgtgagaagg | ctgagcacgc | ctgcacctcc | aacccgtgtg | ccaacggggg | 900 |
| ctcttgccat | gaggtgccgt | ccggcttcga | atgccactgc | ccatcgggct | ggagcgggcc | 960 |
| cacctgtgcc | cttgacatcg | atgagtgtgc | ttcgaacccg | tgtgcggccg | gtggcacctg | 1020 |
| tgtggaccag | gtggacggct | tgagtgcat | ctgccccgag | cagtggtgg | gggccaccctg | 1080 |
| ccagctggac | gccaatgagt | gtgaagggaa | gccatgcctt | aacgcttttt | cttgcaaaaa | 1140 |
| cctgattggc | ggctattact | gtgattgcat | cccgggctgg | aagggcatca | actgccatat | 1200 |
| caacgtcaac | gactgtcgcg | ggcagtgtca | gcatggggc | acctgcaagg | acctggtgaa | 1260 |
| cgggtaccag | tgtgtgtgcc | cacggggctt | cggaggccgg | cattgcgagc | tggaacgaga | 1320 |
| caagtgtgcc | agcagcccct | gccacagcgg | cggcctctgc | gaggacctgg | ccgacggctt | 1380 |
| ccactgccac | tgccccagg | gcttctccgg | gcctctctgt | gaggtggatg | tcgacctttg | 1440 |
| tgagccaagc | ccctgccgga | acggcgctcg | ctgctataac | ctggagggtg | actattactg | 1500 |
| cgcctgccct | gatgactttg | gtggcaagaa | ctgctccgtg | ccccgcgagc | cgtgccctgg | 1560 |
| cggggcctgc | agagtgatcg | atggctgcgg | gtcagacgcg | gggcctggga | tgcctggcac | 1620 |
| agcagcctcc | ggcgtgtgtg | gccccatgg | acgctgcgtc | agccagccag | ggggcaactt | 1680 |
| ttcctgcatc | tgtgacagtg | gctttactgg | cacctactgc | catgagaaca | ttgacgactg | 1740 |
| cctgggccag | ccctgccgca | atggggcac | atgcatcgat | gaggtggacg | ccttccgctg | 1800 |
| cttctgcccc | agcggttggg | agggcgagct | ctgcgacacc | aatcccaacg | actgccttcc | 1860 |
| cgatccctgc | cacagccgcg | gccgctgcta | cgacctggtc | aatgacttct | actgtgcgtg | 1920 |
| cgacgacggc | tggaagggca | agacctgcca | ctcacgcgag | ttccagtgcg | atgcctacac | 1980 |

```
ctgcagcaac ggtggcacct gctacgacag cggcgacacc ttccgctgcg cctgcccccc   2040
cggctggaag ggcagcacct gcgccgtcgc caagaacagc agctgcctgc ccaacccctg   2100
tgtgaatggt ggcacctgcg tgggcagcgg ggcctccttc cctgcatct gccgggacgg   2160 ctgggagggt cgtacttgca ctcacaatac caacgactgc aaccctctgc cttgctacaa   2220
tggtggcatc tgtgttgacg gcgtcaactg gttccgctgc gagtgtgcac ctggcttcgc   2280
ggggcctgac tgccgcatca acatcgacga gtgccagtcc tcgccctgtg cctacggggc   2340
cacgtgtgtg gatgagatca acgggtatcg ctgtagctgc ccacccggcc gagccggccc   2400
ccggtgccag gaagtgatcg ggttcgggag atcctgctgg tcccggggca ctccgttccc   2460
acacggaagc tcctgggtgg aagactgcaa cagctgccgc tgcctggatg ccgccgtga   2520 ctgcagcaag gtgtggtgcg gatggaagcc ttgtctgctg gccggccagc ccgaggccct   2580
gagcgcccag tgcccactgg ggcaaaggtg cctggagaag gccccaggcc agtgtctgcg   2640
accaccctgt gaggcctggg gggagtgcgg cgcagaagag ccaccgagca cccctgcct   2700 gccacgctcc ggcccctgg acaataactg tgcccgcctc accttgcatt tcaaccgtga   2760
ccacgtgccc cagggcacca cggtgggcgc catttgctcc gggatccgct ccctgccagc   2820
cacaagggct gtggcacggg accgcctgct ggtgttgctt tgcgaccggg cgtcctcggg   2880
ggccagtgct gtggaggtgg ccgtgtcctt cagccctgcc agggacctgc ctgacagcag   2940
cctgatccag ggcgcggccc acgccatcgt ggccgccatc cccagcgggg gaacagctc   3000 actgctcctg gctgtcaccg aggtcaaggt ggagacggtt gttacgggcg gctcttccac   3060
aggtctgctg gtgcctgtgc tgtgtggtgc cttcagcgtg ctgtggctgg cgtgcgtggt   3120
cctgtgcgtg tggtggacac gcaagcgcag gaaagagcgg gagaggagcc ggctgccgcg   3180
ggaggagagc gccaacaacc agtgggcccc gctcaacccc atccgcaacc ccattgagcg   3240 gccgggggg cacaaggacg tgctctacca gtgcaagaac ttcactccac cgccgcgcag   3300
gcgctgcccg ggccggccgg ccacgcggcc gtcaggagg atgaggagga cgaggatctt   3360
ggccgcggtg aggaggactc cctggaggcg gagaagttcc tctcacacaa attcaccaaa   3420
gatcctggcc gctcgccggg gaggccggcc cactgggcct caggccccaa agtggacaac   3480
cgcgcggtca ggagcatcaa tgaggcccgc tacgtcggca agggaagtag gcggctgca   3540 gctgggccgg gacccagggc cctcggtggg agccatgccg tctgccggac ccggaggccg   3600
aggccatgtg catagtttct ttattttgtg taaaaaaacc accaaaaaca aaaaccaaat   3660 gtttatttc tacgtttctt taaccttgta taaattattc agtaactgtc aggctgaaaa   3720
caatggagta ttctcggata gttgctattt ttgtaaagta gccgtgcgtg gcactcgctg   3780
tatgaaagga gagagcaaag ggtgtctgcg tcgtcaccaa atcgtcgcgt ttgttaccag   3840
aggttgtgca ctgtttacag aatcttcctt ttattcctca ctcgggtttc tctgtgctcc   3900
aggccaaagt gccggtgaga cccatggctg tgttggtgtg gccatggct gttggtggga   3960 cccgtggctg atggtgtggc ctgtggctgt cggtgggact cgtggctgtc aatgggacct   4020
gtggctgtcg gtgggaccta cggtggtcgg tgggaccctg gttattgatg tggccctggc   4080
tgccggcacg gcccgtggct gttgacgcac ctgtggttgt tagtgggcc tgaggtcatc   4140 ggcgtggccc aaggccggca ggtcaacctc gcgcttgctg ccagtccac cctgcctgcc   4200 gtctgtgctt cctcctgccc agaacgcccg ctccagcgat ctctccactg tgctttcaga   4260
agtgcccttc ctgctgcgca gttctcccat cctgggacgg cggcagtatt gaagctcgtg   4320
```

-continued

```
acaagtgcct tcacacagac ccctcgcaac tgtccacgcg tgccgtggca ccaggcgctg   4380
cccacctgcc ggccccggcc gcccctcctc gtgaaagtgc attttttgtaa atgtgtacat   4440 attaaaggaa gcactctgta taaaaaaaaa aaaccggaat tcc                    4483
```

<210> SEQ ID NO 6
<211> LENGTH: 1257
<212> TYPE: PRT
<213> ORGANISM: Homo sapiens

<400> SEQUENCE: 6

```
Met Ile Asn Pro Glu Asp Arg Trp Lys Ser Leu His Phe Ser Gly His
1               5                   10                  15

Val Ala His Leu Glu Leu Gln Ile Arg Val Arg Cys Asp Glu Asn Tyr
            20                  25                  30

Tyr Ser Ala Thr Cys Asn Lys Phe Cys Arg Pro Arg Asn Asp Phe Phe
        35                  40                  45

Gly His Tyr Thr Cys Asp Gln Tyr Gly Asn Lys Ala Cys Met Asp Gly
    50                  55                  60

Trp Met Gly Lys Glu Cys Lys Glu Ala Val Cys Lys Gln Gly Cys Asn
65                  70                  75                  80

Leu Leu His Gly Gly Cys Thr Val Pro Gly Glu Cys Arg Cys Ser Tyr
                85                  90                  95

Gly Trp Gln Gly Arg Phe Cys Asp Glu Cys Val Pro Tyr Pro Gly Cys
            100                 105                 110

Val His Gly Ser Cys Val Glu Pro Trp Gln Cys Asn Cys Glu Thr Asn
        115                 120                 125

Trp Gly Gly Leu Leu Cys Asp Lys Asp Leu Asn Tyr Cys Gly Ser His
    130                 135                 140

His Pro Cys Thr Asn Gly Gly Thr Cys Ile Asn Ala Glu Pro Asp Gln
145                 150                 155                 160

Tyr Arg Cys Thr Cys Pro Asp Gly Tyr Ser Gly Arg Asn Cys Glu Lys
                165                 170                 175

Ala Glu His Ala Cys Thr Ser Asn Pro Cys Ala Asn Gly Gly Ser Cys
            180                 185                 190

His Glu Val Pro Ser Gly Phe Glu Cys His Cys Pro Ser Gly Trp Ser
        195                 200                 205

Gly Pro Thr Cys Ala Leu Asp Ile Asp Glu Cys Ala Ser Asn Pro Cys
    210                 215                 220

Ala Ala Gly Gly Thr Cys Val Asp Gln Val Asp Gly Phe Glu Cys Ile
225                 230                 235                 240

Cys Pro Glu Gln Trp Val Gly Ala Thr Cys Gln Leu Asp Ala Asn Glu
                245                 250                 255

Cys Glu Gly Lys Pro Cys Leu Asn Ala Phe Ser Cys Lys Asn Leu Ile
            260                 265                 270

Gly Gly Tyr Tyr Cys Asp Cys Ile Pro Gly Trp Lys Gly Ile Asn Cys
        275                 280                 285

His Ile Asn Val Asn Asp Cys Arg Gly Gln Cys Gln His Gly Gly Thr
    290                 295                 300

Cys Lys Asp Leu Val Asn Gly Tyr Gln Cys Val Cys Pro Arg Gly Phe
305                 310                 315                 320

Gly Gly Arg His Cys Glu Leu Glu Arg Asp Lys Cys Ala Ser Ser Pro
                325                 330                 335

Cys His Ser Gly Gly Leu Cys Glu Asp Leu Ala Asp Gly Phe His Cys
            340                 345                 350
```

```
His Cys Pro Gln Gly Phe Ser Gly Pro Leu Cys Glu Val Asp Val Asp
        355                 360                 365

Leu Cys Glu Pro Ser Pro Cys Arg Asn Gly Ala Arg Cys Tyr Asn Leu
    370                 375                 380

Glu Gly Asp Tyr Tyr Cys Ala Cys Pro Asp Asp Phe Gly Gly Lys Asn
385                 390                 395                 400

Cys Ser Val Pro Arg Glu Pro Cys Pro Gly Gly Ala Cys Arg Val Ile
                405                 410                 415

Asp Gly Cys Gly Ser Asp Ala Gly Pro Gly Met Pro Gly Thr Ala Ala
            420                 425                 430

Ser Gly Val Cys Gly Pro His Gly Arg Cys Val Ser Gln Pro Gly Gly
            435                 440                 445

Asn Phe Ser Cys Ile Cys Asp Ser Gly Phe Thr Gly Thr Tyr Cys His
    450                 455                 460

Glu Asn Ile Asp Asp Cys Leu Gly Gln Pro Cys Arg Asn Gly Gly Thr
465                 470                 475                 480

Cys Ile Asp Glu Val Asp Ala Phe Arg Cys Phe Cys Pro Ser Gly Trp
                485                 490                 495

Glu Gly Glu Leu Cys Asp Thr Asn Pro Asn Asp Cys Leu Pro Asp Pro
                500                 505                 510

Cys His Ser Arg Gly Arg Cys Tyr Asp Leu Val Asn Asp Phe Tyr Cys
        515                 520                 525

Ala Cys Asp Asp Gly Trp Lys Gly Lys Thr Cys His Ser Arg Glu Phe
    530                 535                 540

Gln Cys Asp Ala Tyr Thr Cys Ser Asn Gly Gly Thr Cys Tyr Asp Ser
545                 550                 555                 560

Gly Asp Thr Phe Arg Cys Ala Cys Pro Pro Gly Trp Lys Gly Ser Thr
                565                 570                 575

Cys Ala Val Ala Lys Asn Ser Ser Cys Leu Pro Asn Pro Cys Val Asn
            580                 585                 590

Gly Gly Thr Cys Val Gly Ser Gly Ala Ser Phe Ser Cys Ile Cys Arg
            595                 600                 605

Asp Gly Trp Glu Gly Arg Thr Cys Thr His Asn Thr Asn Asp Cys Asn
    610                 615                 620

Pro Leu Pro Cys Tyr Asn Gly Gly Ile Cys Val Asp Gly Val Asn Trp
625                 630                 635                 640

Phe Arg Cys Glu Cys Ala Pro Gly Phe Ala Gly Pro Asp Cys Arg Ile
                645                 650                 655

Asn Ile Asp Glu Cys Gln Ser Ser Pro Cys Ala Tyr Gly Ala Thr Cys
            660                 665                 670

Val Asp Glu Ile Asn Gly Tyr Arg Cys Ser Cys Pro Pro Gly Arg Ala
            675                 680                 685

Gly Pro Arg Cys Gln Glu Val Ile Gly Phe Gly Arg Ser Cys Trp Ser
    690                 695                 700

Arg Gly Thr Pro Phe Pro His Gly Ser Ser Trp Val Glu Asp Cys Asn
705                 710                 715                 720

Ser Cys Arg Cys Leu Asp Gly Arg Arg Asp Cys Ser Lys Val Trp Cys
                725                 730                 735

Gly Trp Lys Pro Cys Leu Leu Ala Gly Gln Pro Glu Ala Leu Ser Ala
            740                 745                 750

Gln Cys Pro Leu Gly Gln Arg Cys Leu Glu Lys Ala Pro Gly Gln Cys
            755                 760                 765
```

-continued

```
Leu Arg Pro Pro Cys Glu Ala Trp Gly Glu Cys Gly Ala Glu Pro
    770                 775                 780

Pro Ser Thr Pro Cys Leu Pro Arg Ser Gly His Leu Asp Asn Asn Cys
785                 790                 795                 800

Ala Arg Leu Thr Leu His Phe Asn Arg Asp His Val Pro Gln Gly Thr
                    805                 810                 815

Thr Val Gly Ala Ile Cys Ser Gly Ile Arg Ser Leu Pro Ala Thr Arg
                820                 825                 830

Ala Val Ala Arg Asp Arg Leu Leu Val Leu Cys Asp Arg Ala Ser
    835                 840                 845

Ser Gly Ala Ser Ala Val Glu Val Ala Val Ser Phe Ser Pro Ala Arg
    850                 855                 860

Asp Leu Pro Asp Ser Ser Leu Ile Gln Gly Ala Ala His Ala Ile Val
865                 870                 875                 880

Ala Ala Ile Thr Gln Arg Gly Asn Ser Ser Leu Leu Leu Ala Val Thr
                    885                 890                 895

Glu Val Lys Val Glu Thr Val Val Thr Gly Gly Ser Ser Thr Gly Leu
                900                 905                 910

Leu Val Pro Val Leu Cys Gly Ala Phe Ser Val Leu Trp Leu Ala Cys
                915                 920                 925

Val Val Leu Cys Val Trp Trp Thr Arg Lys Arg Lys Glu Arg Glu
    930                 935                 940

Arg Ser Arg Leu Pro Arg Glu Glu Ser Ala Asn Asn Gln Trp Ala Pro
945                 950                 955                 960

Leu Asn Pro Ile Arg Asn Pro Ile Glu Arg Pro Gly His Lys Asp
                965                 970                 975

Val Leu Tyr Gln Cys Lys Asn Phe Thr Pro Pro Arg Arg Cys
    980                 985                 990

Pro Gly Arg Pro Ala Thr Arg Pro  Ser Gly Arg Met Arg  Arg Thr Arg
        995                 1000                1005

Ile Leu  Ala Ala Val Arg  Arg  Thr Pro Trp Arg  Arg Ser Ser
    1010                1015                1020

Ser His  Thr Asn Ser Pro Lys  Ile Leu Ala Ala Arg  Arg Gly Gly
    1025                1030                1035

Arg Pro  Thr Gly Pro Gln Ala  Pro Lys Trp Thr Thr  Ala Arg Ser
    1040                1045                1050

Gly Ala  Ser Met Arg Pro Ala  Thr Ser Ala Arg Glu  Val Gly Arg
    1055                1060                1065

Leu Gln  Leu Gly Arg Asp Pro  Gly Pro Ser Val Gly  Ala Met Pro
    1070                1075                1080

Ser Ala  Gly Pro Gly Gly Arg  Gly His Val His Ser  Phe Phe Ile
    1085                1090                1095

Leu Cys  Lys Lys Thr Thr Lys  Asn Lys Asn Gln Met  Phe Ile Phe
    1100                1105                1110

Tyr Val  Ser Leu Thr Leu Tyr  Lys Leu Phe Ser Asn  Cys Gln Ala
    1115                1120                1125

Glu Asn  Asn Gly Val Phe Ser  Asp Ser Cys Tyr Phe  Cys Lys Val
    1130                1135                1140

Ala Val  Arg Gly Thr Arg Cys  Met Lys Gly Glu Ser  Lys Gly Cys
    1145                1150                1155

Leu Arg  Arg His Gln Ile Val  Ala Phe Val Thr Arg  Gly Cys Ala
    1160                1165                1170

Leu Phe  Thr Glu Ser Ser Phe  Tyr Ser Ser Leu Gly  Phe Leu Cys
```

```
           1175                1180                1185
Ala Pro Gly Gln Ser Ala Gly Glu Thr His Gly Cys Val Gly Val
   1190                1195                1200

Ala His Gly Cys Trp Trp Asp Pro Trp Leu Met Val Trp Pro Val
   1205                1210                1215

Ala Val Gly Gly Thr Arg Gly Cys Gln Trp Asp Leu Trp Leu Ser
   1220                1225                1230

Val Gly Pro Thr Val Val Gly Gly Thr Leu Val Ile Asp Val Ala
   1235                1240                1245

Leu Ala Ala Gly Thr Ala Arg Gly Cys
   1250                1255

<210> SEQ ID NO 7
<211> LENGTH: 3582
<212> TYPE: DNA
<213> ORGANISM: Gallus sp.

<400> SEQUENCE: 7
caggtggcgt cagcatcggg acagttcgag ctggagatct tatccgtgca gaatgtgaac        60
ggcgtgctgc agaacgggaa ctgctgcgac ggcactcgaa accccggaga taaaaagtgc       120
accagagatg agtgtgacac ctactttaaa gtttgcctga aggagtacca gtcgcgggtc       180
actgctggcg gcccttgcag cttcggatcc aaatccaccc ctgtcatcgg cgggaatacc       240
ttcaatttaa agtacagccg gaataatgaa agaaccggaa ttgttatccc tttcacgttc       300
gcctggccga tcctacacg ttgcttgtt gaggcatggg attacaatga taactctact       360
aatcccgatc gcataattga aaggcatcc cactctggca tgatcaatcc aagccgtcag       420
tggcagacgt tgaaacataa cacaggagct gcccactttg agtatcaaat ccgtgtgact       480
tgcgcagaac attactatgg ctttggatgc aacaagtttt gtcgaccgag agatgacttc       540
ttcactcacc atacctgtga ccagaatggc aacaaaacct gcttggaagg ctggacggga       600
ccagaatgca acaaagctat tgtcgtcagg gatgtagcc caagcatgg ttcttgcaca       660 gttccaggag agtgcaggtg tcagtatgga tggcaaggcc agtactgtga taagtgcatt       720
ccacacccgg gatgtgtcca tggcacttgc attgaaccat ggcagtgcct ctgtgaaacc       780
aactggggtg tcagctctg tgacaaagac ctgaactact gtggaaccca cccaccctgt       840
ttgaatggtg gtacctgcag caacactggc cccgataaat accagtgttc ctgccctgag       900
ggttactcag acagaactg tgaaatagcg gagcatgcgt gcctctctga tccgtgccac       960
aacggaggaa gctgcctaga acgtctaca ggatttgaat gtgtgtgtgc acctggctgg      1020 gctgaccaa cttgcactga taatattgat gattgttctc caaatccctg tggtcatgga      1080
ggaacttgcc aagatctagt tgatggattt aagtgtattt gcccacctca gtggactggc      1140
aaaacatgcc agctagatgc gaatgaatgt gagggcaaac cctgtgtcaa tgccaactcc      1200
tgcaggaact tgattggcag ctactattgt gactgcatta ctggctggtc tggccacaac      1260
tgtgatataa atattaatga ttgtcgtgga caatgtcaga atggaggatc ctgtcgggac      1320
ttggttaatg gttatcggtg catctgttca cctggctatg caggagatca ctgtgagaaa      1380
gacatcaatg aatgtgcaag taaccccttgc atgaatgggg gtcactgcca ggatgaaatc      1440
aatggattcc aatgtctgtg tcctgctggt ttctcaggaa acctctgtca gctggatata      1500
gactactgtg agccaaaccc ttgccagaac ggtgcccagt gcttcaatct gctatggac      1560 tatttctgta actgccctga agattacgaa ggcaagaact gctcccacct gaaagatcac      1620
```

-continued

```
tgccgcacaa ctccttgtga agtaatcgac agctgtacag tggcagtggc ttctaacagc    1680
acaccagaag gagttcgtta catttcttca aatgtctgtg gtcctcatgg aaaatgcaag    1740
agccaagcag gtggaaaatt cacctgtgaa tgcaacaaag gattcactgg cacctactgt    1800
catgagaata tcaatgactg tgagagcaac ccctgtaaaa atggtggcac ttgtattgac    1860
ggtgtaaact cctacaaatg tatttgtagt gatggatggg aaggaacata ttgtgaaaca    1920
aatattaatg actgcagtaa aaaccccctgc acaatggaga gaacttgccg agacttggtc    1980
aatgacttct tctgtgaatg taaaaatggg tggaaggaa aaacttgcca ctctcgtgac     2040
agccagtgtg atgaggcaac atgcaataat ggaggaacat gttatgatga gggggacact    2100
ttcaagtgca tgtgtcctgc aggatgggaa ggagccactt gtaatatagc aaggaacagc    2160
agctgcctgc caaaccccctg tcacaatggt ggtacctgtg tagttagtgg ggattctttc    2220
acttgtgtct gcaaggaggg ctgggaagga ccgacatgta ctcagaacac aaatgactgc    2280
agtcctcatc cttgttacaa cagtggtact tgtgtggatg gagacaactg gtaccgctgt    2340
gagtgcgctc ccggcttcgc aggtcccgac tgtaggatca acatcaatga atgtcagtct    2400
tcaccctgtg cctttgggc tacttgtgtg atgaaatta tgggtaccg ttgcatttgt       2460
ccaccgggtc gcagtggtcc aggatgccag gaagttacag ggaggccttg ctttaccagt    2520
attcgagtaa tgccagacgg tgctaagtgg gatgatgact gtaatacttg tcagtgtttg    2580
aatggaaaag tcacctgttc taaggttttgg tgtggtcctc gaccttgtat aatacatgcc   2640
aaaggtcata atgaatgccc agctggacac gcttgtgttc ctgttaaaga agaccattgt    2700
ttcactcatc cttgtgctgc agtgggtgaa tgctggcctt ctaatcagca gcctgtgaag    2760
accaaatgca attctgattc ttattaccaa gataattgtg ccaacatcac cttcaccttt    2820
aataaggaaa tgatggcacc aggccttacc acggagcaca tttgcagtga attgaggaat    2880
ctgaatatcc tgaagaatgt ttctgctgaa tattccatct atattacctg tgagccttca    2940
cacttggcaa ataatgaaat acatgttgct atttctgctg aagatatagg agaagatgaa    3000
aacccaatca ggaaatcac agataagatt attgaccttg tcagtaagcg tgatggaaac    3060
aacacactaa ttgctgcagt cgcagaagtc agagtacaaa ggcgaccagt taagaacaaa    3120
acagatttct tggtgccatt actgagctca gtcttaacag tagcctggat ctgctgtctg    3180
gtaactgttt tctattggtg cattcaaaag cgcagaaagc agagcagcca tactcacaca    3240
gcatctgatg acaacaccac caacaacgta agggagcagc tgaatcagat taaaaaccc     3300
atagagaaac acggagcaaa tactgttcca attaaagact atgaaaacaa aaactctaaa    3360
atcgccaaaa taaggacgca caattcagaa gtggaggaag atgacatgga caaacaccag    3420
caaaaggccc ggtttgccaa gcagccagcg tacactttgg tagacagaga tgaaaagcca    3480
cccaacagca cacccacaaa acacccaaac tggacaaata aacaggacaa cagagacttg    3540
gaaagtgcaa aaagtttaaa tagaatggag tacattgtat ag                       3582
```

<210> SEQ ID NO 8
<211> LENGTH: 1193
<212> TYPE: PRT
<213> ORGANISM: Gallus sp.

<400> SEQUENCE: 8

```
Gln Val Ala Ser Ala Ser Gly Gln Phe Glu Leu Glu Ile Leu Ser Val
 1               5                  10                  15

Gln Asn Val Asn Gly Val Leu Gln Asn Gly Asn Cys Cys Asp Gly Thr
            20                  25                  30
```

```
Arg Asn Pro Gly Asp Lys Lys Cys Thr Arg Asp Glu Cys Asp Thr Tyr
            35                  40                  45

Phe Lys Val Cys Leu Lys Glu Tyr Gln Ser Arg Val Thr Ala Gly Gly
    50                  55                  60

Pro Cys Ser Phe Gly Ser Lys Ser Thr Pro Val Ile Gly Gly Asn Thr
65                  70                  75                  80

Phe Asn Leu Lys Tyr Ser Arg Asn Asn Glu Lys Asn Arg Ile Val Ile
                85                  90                  95

Pro Phe Thr Phe Ala Trp Pro Arg Ser Tyr Thr Leu Leu Val Glu Ala
            100                 105                 110

Trp Asp Tyr Asn Asp Asn Ser Thr Asn Pro Asp Arg Ile Ile Glu Lys
            115                 120                 125

Ala Ser His Ser Gly Met Ile Asn Pro Ser Arg Gln Trp Gln Thr Leu
        130                 135                 140

Lys His Asn Thr Gly Ala Ala His Phe Glu Tyr Gln Ile Arg Val Thr
145                 150                 155                 160

Cys Ala Glu His Tyr Tyr Gly Phe Gly Cys Asn Lys Phe Cys Arg Pro
                165                 170                 175

Arg Asp Asp Phe Phe Thr His Thr Cys Asp Gln Asn Gly Asn Lys
            180                 185                 190

Thr Cys Leu Glu Gly Trp Thr Gly Pro Glu Cys Asn Lys Ala Ile Cys
        195                 200                 205

Arg Gln Gly Cys Ser Pro Lys His Gly Ser Cys Thr Val Pro Gly Glu
    210                 215                 220

Cys Arg Cys Gln Tyr Gly Trp Gln Gly Gln Tyr Cys Asp Lys Cys Ile
225                 230                 235                 240

Pro His Pro Gly Cys Val His Gly Thr Cys Ile Glu Pro Trp Gln Cys
                245                 250                 255

Leu Cys Glu Thr Asn Trp Gly Gly Gln Leu Cys Asp Lys Asp Leu Asn
            260                 265                 270

Tyr Cys Gly Thr His Pro Pro Cys Leu Asn Gly Gly Thr Cys Ser Asn
        275                 280                 285

Thr Gly Pro Asp Lys Tyr Gln Cys Ser Cys Pro Glu Gly Tyr Ser Gly
    290                 295                 300

Gln Asn Cys Glu Ile Ala Glu His Ala Cys Leu Ser Asp Pro Cys His
305                 310                 315                 320

Asn Gly Gly Ser Cys Leu Glu Thr Ser Thr Gly Phe Glu Cys Val Cys
                325                 330                 335

Ala Pro Gly Trp Ala Gly Pro Thr Cys Thr Asp Asn Ile Asp Asp Cys
            340                 345                 350

Ser Pro Asn Pro Cys Gly His Gly Gly Thr Cys Gln Asp Leu Val Asp
        355                 360                 365

Gly Phe Lys Cys Ile Cys Pro Pro Gln Trp Thr Gly Lys Thr Cys Gln
    370                 375                 380

Leu Asp Ala Asn Glu Cys Glu Gly Lys Pro Cys Val Asn Ala Asn Ser
385                 390                 395                 400

Cys Arg Asn Leu Ile Gly Ser Tyr Tyr Cys Asp Cys Ile Thr Gly Trp
                405                 410                 415

Ser Gly His Asn Cys Asp Ile Asn Ile Asn Asp Cys Arg Gly Gln Cys
            420                 425                 430

Gln Asn Gly Gly Ser Cys Arg Asp Leu Val Asn Gly Tyr Arg Cys Ile
        435                 440                 445
```

```
Cys Ser Pro Gly Tyr Ala Gly Asp His Cys Glu Lys Asp Ile Asn Glu
        450                 455                 460

Cys Ala Ser Asn Pro Cys Met Asn Gly Gly His Cys Gln Asp Glu Ile
465                     470                  475                 480

Asn Gly Phe Gln Cys Leu Cys Pro Ala Gly Phe Ser Gly Asn Leu Cys
                    485                 490                 495

Gln Leu Asp Ile Asp Tyr Cys Glu Pro Asn Pro Cys Gln Asn Gly Ala
            500                 505                 510

Gln Cys Phe Asn Leu Ala Met Asp Tyr Phe Cys Asn Cys Pro Glu Asp
        515                 520                 525

Tyr Glu Gly Lys Asn Cys Ser His Leu Lys Asp His Cys Arg Thr Thr
    530                 535                 540

Pro Cys Glu Val Ile Asp Ser Cys Thr Val Ala Val Ala Ser Asn Ser
545                 550                 555                 560

Thr Pro Glu Gly Val Arg Tyr Ile Ser Ser Asn Val Cys Gly Pro His
                565                 570                 575

Gly Lys Cys Lys Ser Gln Ala Gly Gly Lys Phe Thr Cys Glu Cys Asn
            580                 585                 590

Lys Gly Phe Thr Gly Thr Tyr Cys His Glu Asn Ile Asn Asp Cys Glu
        595                 600                 605

Ser Asn Pro Cys Lys Asn Gly Gly Thr Cys Ile Asp Gly Val Asn Ser
    610                 615                 620

Tyr Lys Cys Ile Cys Ser Asp Gly Trp Glu Gly Thr Tyr Cys Glu Thr
625                 630                 635                 640

Asn Ile Asn Asp Cys Ser Lys Asn Pro Cys His Asn Gly Gly Thr Cys
                645                 650                 655

Arg Asp Leu Val Asn Asp Phe Phe Cys Glu Cys Lys Asn Gly Trp Lys
            660                 665                 670

Gly Lys Thr Cys His Ser Arg Asp Ser Gln Cys Asp Glu Ala Thr Cys
        675                 680                 685

Asn Asn Gly Gly Thr Cys Tyr Asp Glu Gly Asp Thr Phe Lys Cys Met
    690                 695                 700

Cys Pro Ala Gly Trp Glu Gly Ala Thr Cys Asn Ile Ala Arg Asn Ser
705                 710                 715                 720

Ser Cys Leu Pro Asn Pro Cys His Asn Gly Gly Thr Cys Val Val Ser
                725                 730                 735

Gly Asp Ser Phe Thr Cys Val Cys Lys Glu Gly Trp Glu Gly Pro Thr
            740                 745                 750

Cys Thr Gln Asn Thr Asn Asp Cys Ser Pro His Pro Cys Tyr Asn Ser
        755                 760                 765

Gly Thr Cys Val Asp Gly Asp Asn Trp Tyr Arg Cys Glu Cys Ala Pro
    770                 775                 780

Gly Phe Ala Gly Pro Asp Cys Arg Ile Asn Ile Asn Glu Cys Gln Ser
785                 790                 795                 800

Ser Pro Cys Ala Phe Gly Ala Thr Cys Val Asp Glu Ile Asn Gly Tyr
                805                 810                 815

Arg Cys Ile Cys Pro Pro Gly Arg Ser Gly Pro Gly Cys Gln Glu Val
            820                 825                 830

Thr Gly Arg Pro Cys Phe Thr Ser Ile Arg Val Met Pro Asp Gly Ala
        835                 840                 845

Lys Trp Asp Asp Asp Cys Asn Thr Cys Gln Cys Leu Asn Gly Lys Val
    850                 855                 860

Thr Cys Ser Lys Val Trp Cys Gly Pro Arg Pro Cys Ile Ile His Ala
```

-continued

```
                865               870               875               880
Lys Gly His Asn Glu Cys Pro Ala Gly His Ala Cys Val Pro Val Lys
                    885                   890                   895
Glu Asp His Cys Phe Thr His Pro Cys Ala Ala Val Gly Glu Cys Trp
                    900                   905                   910
Pro Ser Asn Gln Gln Pro Val Lys Thr Lys Cys Asn Ser Asp Ser Tyr
                    915                   920                   925
Tyr Gln Asp Asn Cys Ala Asn Ile Thr Phe Thr Phe Asn Lys Glu Met
                    930                   935                   940
Met Ala Pro Gly Leu Thr Thr Glu His Ile Cys Ser Glu Leu Arg Asn
945                     950                   955                   960
Leu Asn Ile Leu Lys Asn Val Ser Ala Glu Tyr Ser Ile Tyr Ile Thr
                    965                   970                   975
Cys Glu Pro Ser His Leu Ala Asn Asn Glu Ile His Val Ala Ile Ser
                    980                   985                   990
Ala Glu Asp Ile Gly Glu Asp Glu  Asn Pro Ile Lys Glu  Ile Thr Asp
                    995                  1000                  1005
Lys Ile  Ile Asp Leu Val Ser  Lys Arg Asp Gly Asn  Asn Thr Leu
    1010                 1015                  1020
Ile Ala  Ala Val Ala Glu Val  Arg Val Gln Arg Arg  Pro Val Lys
    1025                 1030                  1035
Asn Lys  Thr Asp Phe Leu Val  Pro Leu Leu Ser Ser  Val Leu Thr
    1040                 1045                  1050
Val Ala  Trp Ile Cys Cys Leu  Val Thr Val Phe Tyr  Trp Cys Ile
    1055                 1060                  1065
Gln Lys  Arg Arg Lys Gln Ser  Ser His Thr His Thr  Ala Ser Asp
    1070                 1075                  1080
Asp Asn  Thr Thr Asn Asn Val  Arg Glu Gln Leu Asn  Gln Ile Lys
    1085                 1090                  1095
Asn Pro  Ile Glu Lys His Gly  Ala Asn Thr Val Pro  Ile Lys Asp
    1100                 1105                  1110
Tyr Glu  Asn Lys Asn Ser Lys  Ile Ala Lys Ile Arg  Thr His Asn
    1115                 1120                  1125
Ser Glu  Val Glu Glu Asp Asp  Met Asp Lys His Gln  Gln Lys Ala
    1130                 1135                  1140
Arg Phe  Ala Lys Gln Pro Ala  Tyr Thr Leu Val Asp  Arg Asp Glu
    1145                 1150                  1155
Lys Pro  Pro Asn Ser Thr Pro  Thr Lys His Pro Asn  Trp Thr Asn
    1160                 1165                  1170
Lys Gln  Asp Asn Arg Asp Leu  Glu Ser Ala Gln Ser  Leu Asn Arg
    1175                 1180                  1185
Met Glu  Tyr Ile Val
    1190

<210> SEQ ID NO 9
<211> LENGTH: 2088
<212> TYPE: DNA
<213> ORGANISM: Gallus sp.

<400> SEQUENCE: 9
gaattcggca cgaggttttt ttttttttt tcccctctt ttctttcttt tccttttgcc      60
atccgaaaga gctgtcagcc gccgccgggc tgcacctaaa ggcgtcggta gggggataac    120
agtcagagac cctcctgaaa gcaggagacg ggacggtacc cctccggctc tgcggggcgg    180
```

-continued

```
ctgcggcccc tccgttcttt cccctcccc gagagacact cttcctttcc cccacgaag      240 acacaggggc aggaacgcga gcgctgcccc tccgccatgg gaggccgctt cctgctgacg      300
ctcgccctcc tctcggcgct gctgtgccgc tgccaggttg acggctccgg ggtgttcgag      360
ctgaagctgc aggagtttgt caacaagaag gggctgctca gcaaccgcaa ctgctgccgg      420 ggggcggcc ccggaggcgc cgggcagcag cagtgcgact gcaagacctt cttccgcgtc      480
tgcctgaagc actaccaggc cagcgtctcc cccgagccgc cctgcaccta cggcagcgcc      540 atcaccccg tcctcggcgc caactccttc agcgtccccg acggcgcggg cggcgccgac      600
cccgccttca gcaaccccat ccgcttcccc ttcggcttca cctggcccgg caccttctcg      660
ctcatcatcg aggctctgca caccgactcc cccgacgacc tcaccacaga aaaccccgag      720
cgcctcatca gccgcctggc cacccagagg cacctggcgg tgggcgagga gtggtcccag      780
gacctgcaca gcagcggccg caccgacctc aagtactcct atcgctttgt gtgtgatgag      840
cactactacg gggaaggctg ctctgtcttc tgccggcccc gtgacgaccg cttcggtcac      900
ttcacctgtg gagagcgtgg cgagaaggtc tgcaacccag gctggaaggg ccagtactgc      960
actgagccga tttgcttgcc tgggtgtgac gagcagcacg gcttctgcga caaacctggg     1020
gaatgcaagt gcagagtggg ttggcagggg cggtactgtg acgagtgcat ccgatacccca     1080 ggctgcctgc acggtacctg tcagcagcca tggcagtgca actgccagga aggctggggc     1140 ggcctttct gcaaccagga cctgaactac tgcactcacc acaagccatg caagaatggt     1200
cggtgtacgt ggttgtggcc agtcccctcg atgtgaacaa gaacggctgg acccatgtgt     1260
ggctccagct gcgagattga aatcaacgaa tgtgatgcca cccttgcaa gaatggtgga     1320 agctgcacgg atctcgagaa cagctattcc tgtacctgcc ccccaggctt ctatggtaaa     1380
aactgtgagc tgagtgcaat gacttgtgct gatggaccgt gcttcaatgg agggcgatgc     1440
actgacaacc ctgatggtgg atacagctgc cgctgcccac tgggttattc tgggttcaac     1500
tgtgaaaaga aaatcgatta ctgcagttcc agcccttgtg ctaatggagc ccagtgcgtt     1560
gacctgggga actcctacat atgccagtgc caggctggct tcactggcag gcactgtgac     1620
gacaacgtgg acgattgcgc ctccttcccc tgcgtcaatg gagggacctg tcaggatggg     1680
gtcaacgact actcctgcac ctgccccccg ggatacaacg ggaagaactg cagcacgccg     1740
gtgagcagat gcgagcacaa cccctgccac aatggggcca cctgccacga gagaagcaac     1800
cgctacgtgt gcgagtgcgc tcgggctac ggcggcctca actgccagtt cctgctcccc     1860
gagccacctc aggggccggt catcgttgac ttcaccgaga agtacacaga gggccagaac     1920
agccagtttc cctggatcgc agtgtgcgcc gggattattc tggtcctcat gctgctgctg     1980
taccagtcgg tgtacgtcat atcagaagag aaagatgagt gcatcatagc aactgaggtg     2040
taaaacagac gtgacgtggc aaagcttatc gataccgtca tcaagctt                  2088
```

<210> SEQ ID NO 10
<211> LENGTH: 2883
<212> TYPE: DNA
<213> ORGANISM: Gallus sp.
<220> FEATURE:
<221> NAME/KEY: misc_feature
<222> LOCATION: (829)..(830)
<223> OTHER INFORMATION: n is a, c, g, or t

<400> SEQUENCE: 10

```
gaattcggca cgaggttttt tttttttttt ttccctctt ttctttcttt tccttttgcc       60
atccgaaaga gctgtcagcc gccgccgggc tgcacctaaa ggcgtcggta gggggataac     120
```

```
agtcagagac cctcctgaaa gcaggagacg ggacggtacc cctccggctc tgcggggcgg      180
ctgcggcccc tccgttcttt cccctcccc gagagacact cttcctttcc ccccacgaag       240
acacaggggc aggaacgcga gcgctgcccc tccgccatgg gaggccgctt cctgctgacg      300
ctcgccctcc tctcggcgct gctgtgccgc tgccaggttg acggctccgg ggtgttcgag      360
ctgaagctgc aggagtttgt caacaagaag gggctgctca gcaaccgcaa ctgctgccgg      420
gggggcggcc ccggaggcgc cgggcagcag cagtgcgact gcaagacctt cttccgcgtc      480
tgcctgaagc actaccaggc cagcgtctcc cccgagccgc cctgcaccta cggcagcgcc      540 atcaccccg tcctcggcgc caactccttc agcgtccccg acggcgcggg cggcgccgac       600
cccgccttca gcaaccccat ccgcttcccc ttcggcttca cctggcccgg caccttctcg      660
ctcatcatcg aggctctgca caccgactcc cccgacgacc tcaccacaga aaaccccgag      720
cgcctcatca gccgcctggc cacccagagg cacctggcgg tgggcgagga gtggtcccag      780
gacctgcaca gcagcggccg caccgacctc aagtactcct atcgctttnn gtgtgatgag      840
cactactacg gggaaggctg ctctgtcttc tgccggcccc gtgacgaccg cttcggtcac      900
ttcacctgtg gagagcgtgg cgagaaggtc tgcaacccag gctggaaggg ccagtactgc      960
actgagccga tttgcttgcc tgggtgtgac gagcagcacg gcttctgcga caaacctggg     1020
gaatgcaagt gcagagtggg ttggcagggg cggtactgtg acgagtgcat ccgatacccca    1080 ggctgcctgc acgtacctg tcagcagcca tggcagtgca actgccagga aggctggggc      1140 ggcctttttct gcaaccagga cctgaactac tgcactcacc acaagccatg caagaatggt    1200
gccacatgca ccaacaccgg tcaggggagc tacacttgtt cttgccgacc tgggtacaca     1260
ggctccagct gcgagattga aatcaacgaa tgtgatgcca cccttgcaa gaatggtgga      1320 agctgcacgg atctcgagaa cagctattcc tgtacctgcc ccccaggctt ctatggtaaa     1380
aactgtgagc tgagtgcaat gacttgtgct gatggaccgt gcttcaatgg agggcgatgc     1440
actgacaacc ctgatggtgg atacagctgc cgctgcccac tgggttattc tgggttcaac    1500
tgtgaaaaga aaatcgatta ctgcagttcc agcccttgtg ctaatggagc ccagtgcgtt    1560
gacctgggga actcctacat atgccagtgc caggctggct tcactggcag gcactgtgac    1620
gacaacgtgg acgattgcgc ctccttcccc tgcgtcaatg gagggacctg tcaggatggg    1680
gtcaacgact actcctgcac ctgccccccg ggatacaacg ggaagaactg cagcacgccg    1740
gtgagcagat gcgagcacaa ccctgccac aatggggcca cctgccacga gagaagcaac     1800
cgctacgtgt gcgagtgcgc tcggggctac ggcggcctca actgccagtt cctgctcccc    1860
gagccacctc aggggccggt catcgttgac ttcaccgaga agtacacaga gggccagaac    1920
agccagtttc cctggatcgc agtgtgcgcc gggattattc tggtcctcat gctgctgctg    1980
ggttgcgccg ccatcgtcgt ctgcgtcagg ctgaaggtgc agaagaggca ccaccagccc    2040
gaggcctgca ggagtgaaac ggagaccatg aacaacctgg cgaactgcca gcgcgagaag    2100
gacatctcca tcagcgtcat cggtgccact cagattaaaa acacaaataa gaaagtagac    2160
tttcacagcg ataactccga taaaaacggc tacaaagtta gatacccatc agtggattac    2220
aatttggtgc atgaactcaa gaatgaggac tctgtgaaag aggagcatgg caaatgcgaa    2280
gccaagtgtg aaacgtatga ttcagaggca gaagagaaaa gcgcagtaca gctaaaaagt    2340
agtgacactt ctgaaagaaa acggccagat tcagtatatt ccacttcaaa ggacacaaag    2400
taccagtcgg tgtacgtcat atcagaagag aaagatgagt gcatcatagc aactgaggtt    2460
```

```
agtatcccac ctggcagtcg gacaagtctt ggtgtgtgat cccatccag cgcaggtcag    2520 ggcggccaaa ccattctacc tgctgccaca gtcatctgta cccaatgaaa actggccacc    2580
ttcagtctgt ggcactgcag acgttgaaaa aacttgttgt ggattaacat aagctccagt    2640
gggggttaca gggacagcaa tttttgcagg caagggtata actgtagtgc agttgtagct    2700
tactaaccct actgactcat tctttcgtgt gcttcctgca gagcctgttt ttgcttggca    2760
ttgaggtgaa gtcctgaccc tctgcatcct catagtcctc tgctttcttt ttattaacct    2820
cttctggtct ctgcttgtgt tttctctcaa caggtgtaaa acagacgtga cgtggcaaag    2880
ctt                                                                 2883
```

<210> SEQ ID NO 11
<211> LENGTH: 728
<212> TYPE: PRT
<213> ORGANISM: Gallus sp.

<400> SEQUENCE: 11

```
Met Gly Gly Arg Phe Leu Leu Thr Leu Ala Leu Leu Ser Ala Leu Leu
1               5                   10                  15

Cys Arg Cys Gln Val Asp Gly Ser Gly Val Phe Glu Leu Lys Leu Gln
            20                  25                  30

Glu Phe Val Asn Lys Lys Gly Leu Leu Ser Asn Arg Asn Cys Cys Arg
        35                  40                  45

Gly Gly Gly Pro Gly Gly Ala Gly Gln Gln Gln Cys Asp Cys Lys Thr
    50                  55                  60

Phe Phe Arg Val Cys Leu Lys His Tyr Gln Ala Ser Val Ser Pro Glu
65                  70                  75                  80

Pro Pro Cys Thr Tyr Gly Ser Ala Ile Thr Pro Val Leu Gly Ala Asn
                85                  90                  95

Ser Phe Ser Val Pro Asp Gly Ala Gly Gly Ala Asp Pro Ala Phe Ser
            100                 105                 110

Asn Pro Ile Arg Phe Pro Phe Gly Phe Thr Trp Pro Gly Thr Phe Ser
        115                 120                 125

Leu Ile Ile Glu Ala Leu His Thr Asp Ser Pro Asp Asp Leu Thr Thr
    130                 135                 140

Glu Asn Pro Glu Arg Leu Ile Ser Arg Leu Ala Thr Gln Arg His Leu
145                 150                 155                 160

Ala Val Gly Glu Glu Trp Ser Gln Asp Leu His Ser Ser Gly Arg Thr
                165                 170                 175

Asp Leu Lys Tyr Ser Tyr Arg Phe Val Cys Asp Glu His Tyr Tyr Gly
            180                 185                 190

Glu Gly Cys Ser Val Phe Cys Arg Pro Arg Asp Asp Arg Phe Gly His
        195                 200                 205

Phe Thr Cys Gly Glu Arg Gly Glu Lys Val Cys Asn Pro Gly Trp Lys
    210                 215                 220

Gly Gln Tyr Cys Thr Glu Pro Ile Cys Leu Pro Gly Cys Asp Glu Gln
225                 230                 235                 240

His Gly Phe Cys Asp Lys Pro Gly Glu Cys Lys Cys Arg Val Gly Trp
                245                 250                 255

Gln Gly Arg Tyr Cys Asp Glu Cys Ile Arg Tyr Pro Gly Cys Leu His
            260                 265                 270

Gly Thr Cys Gln Gln Pro Trp Gln Cys Asn Cys Gln Glu Gly Trp Gly
        275                 280                 285

Gly Leu Phe Cys Asn Gln Asp Leu Asn Tyr Cys Thr His His Lys Pro
```

-continued

```
                290                 295                 300
Cys Lys Asn Gly Ala Thr Cys Thr Asn Thr Gly Gln Gly Ser Tyr Thr
305                 310                 315                 320

Cys Ser Cys Arg Pro Gly Tyr Thr Gly Ser Ser Cys Glu Ile Glu Ile
                325                 330                 335

Asn Glu Cys Asp Ala Asn Pro Cys Lys Asn Gly Gly Ser Cys Thr Asp
                340                 345                 350

Leu Glu Asn Ser Tyr Ser Cys Thr Cys Pro Pro Gly Phe Tyr Gly Lys
                355                 360                 365

Asn Cys Glu Leu Ser Ala Met Thr Cys Ala Asp Gly Pro Cys Phe Asn
370                 375                 380

Gly Gly Arg Cys Thr Asp Asn Pro Asp Gly Gly Tyr Ser Cys Arg Cys
385                 390                 395                 400

Pro Leu Gly Tyr Ser Gly Phe Asn Cys Glu Lys Lys Ile Asp Tyr Cys
                405                 410                 415

Ser Ser Ser Pro Cys Ala Asn Gly Ala Gln Cys Val Asp Leu Gly Asn
                420                 425                 430

Ser Tyr Ile Cys Gln Cys Gln Ala Gly Phe Thr Gly Arg His Cys Asp
                435                 440                 445

Asp Asn Val Asp Asp Cys Ala Ser Phe Pro Cys Val Asn Gly Gly Thr
                450                 455                 460

Cys Gln Asp Gly Val Asn Asp Tyr Ser Cys Thr Cys Pro Pro Gly Tyr
465                 470                 475                 480

Asn Gly Lys Asn Cys Ser Thr Pro Val Ser Arg Cys Glu His Asn Pro
                485                 490                 495

Cys His Asn Gly Ala Thr Cys His Glu Arg Ser Asn Arg Tyr Val Cys
                500                 505                 510

Glu Cys Ala Arg Gly Tyr Gly Gly Leu Asn Cys Gln Phe Leu Leu Pro
                515                 520                 525

Glu Pro Pro Gln Gly Pro Val Ile Val Asp Phe Thr Glu Lys Tyr Thr
                530                 535                 540

Glu Gly Gln Asn Ser Gln Phe Pro Trp Ile Ala Val Cys Ala Gly Ile
545                 550                 555                 560

Ile Leu Val Leu Met Leu Leu Leu Gly Cys Ala Ala Ile Val Val Cys
                565                 570                 575

Val Arg Leu Lys Val Gln Lys Arg Lys Lys Gln Pro Glu Ala Cys Arg
                580                 585                 590

Ser Glu Thr Glu Thr Met Asn Asn Leu Ala Asn Cys Gln Arg Glu Lys
                595                 600                 605

Asp Ile Ser Ile Ser Val Ile Gly Ala Thr Gln Ile Lys Asn Thr Asn
610                 615                 620

Lys Lys Val Asp Phe His Ser Asp Asn Ser Asp Lys Asn Gly Tyr Lys
625                 630                 635                 640

Val Arg Tyr Pro Ser Val Asp Tyr Asn Leu Val His Glu Leu Lys Asn
                645                 650                 655

Glu Asp Ser Val Lys Glu His Gly Lys Cys Glu Ala Lys Cys Glu
                660                 665                 670

Thr Tyr Asp Ser Glu Ala Glu Lys Ser Ala Val Gln Leu Lys Ser
                675                 680                 685

Ser Asp Thr Ser Glu Arg Lys Arg Pro Asp Ser Val Tyr Ser Thr Ser
                690                 695                 700

Lys Asp Thr Lys Tyr Gln Ser Val Tyr Val Ile Ser Glu Glu Lys Asp
705                 710                 715                 720
```

```
Glu Cys Ile Ile Ala Thr Glu Val
                725

<210> SEQ ID NO 12
<211> LENGTH: 721
<212> TYPE: PRT
<213> ORGANISM: Xenopus sp.

<400> SEQUENCE: 12

Met Gly Gln Gln Arg Met Leu Thr Leu Leu Val Leu Ser Ala Val Leu
1               5                   10                  15

Cys Gln Ile Ser Cys Ser Gly Leu Phe Glu Leu Arg Leu Gln Glu Phe
                20                  25                  30

Val Asn Lys Lys Gly Leu Leu Gly Asn Met Asn Cys Cys Arg Pro Gly
            35                  40                  45

Ser Leu Ala Ser Leu Gln Arg Cys Glu Cys Lys Thr Phe Phe Arg Ile
        50                  55                  60

Cys Leu Lys His Tyr Gln Ser Asn Val Ser Pro Glu Pro Pro Cys Thr
65                  70                  75                  80

Tyr Gly Gly Ala Val Thr Pro Val Leu Gly Thr Asn Ser Phe Val Val
                85                  90                  95

Pro Glu Ser Ser Asn Ala Asp Pro Thr Phe Ser Asn Pro Ile Arg Phe
            100                 105                 110

Pro Phe Gly Phe Thr Trp Pro Gly Thr Phe Ser Leu Ile Ile Glu Ala
        115                 120                 125

Ile His Ala Asp Ser Ala Asp Asp Leu Asn Thr Glu Asn Pro Glu Arg
130                 135                 140

Leu Ile Ser Arg Leu Ala Thr Gln Arg His Leu Thr Val Gly Glu Gln
145                 150                 155                 160

Trp Ser Gln Asp Leu His Ser Ser Asp Arg Thr Glu Leu Lys Tyr Ser
                165                 170                 175

Tyr Arg Phe Val Cys Asp Glu Tyr Tyr Tyr Gly Glu Gly Cys Ser Asp
            180                 185                 190

Tyr Cys Arg Pro Arg Asp Asp Ala Phe Gly His Phe Ser Cys Gly Glu
        195                 200                 205

Lys Gly Glu Lys Leu Cys Asn Pro Gly Trp Lys Gly Leu Tyr Cys Thr
210                 215                 220

Glu Pro Ile Cys Leu Pro Gly Cys Asp Glu His His Gly Tyr Cys Asp
225                 230                 235                 240

Lys Pro Gly Glu Cys Lys Cys Arg Val Gly Trp Gln Gly Arg Tyr Cys
                245                 250                 255

Asp Glu Cys Ile Arg Tyr Pro Gly Cys Leu His Gly Thr Cys Gln Gln
            260                 265                 270

Pro Trp Gln Cys Asn Cys Gln Glu Gly Trp Gly Gly Leu Phe Cys Asn
        275                 280                 285

Gln Asp Leu Asn Tyr Cys Thr His His Lys Pro Cys Glu Asn Gly Ala
290                 295                 300

Thr Cys Thr Asn Thr Gly Gln Gly Ser Tyr Thr Cys Ser Cys Arg Pro
305                 310                 315                 320

Gly Tyr Thr Gly Ser Asn Cys Glu Ile Glu Val Asn Glu Cys Asp Ala
                325                 330                 335

Asn Pro Cys Lys Asn Gly Gly Ser Cys Ser Asp Leu Glu Asn Ser Tyr
            340                 345                 350

Thr Cys Ser Cys Pro Pro Gly Phe Tyr Gly Lys Asn Cys Glu Leu Ser
```

```
                355                 360                 365
Ala Met Thr Cys Ala Asp Gly Pro Cys Phe Asn Gly Gly Arg Cys Ala
        370                 375                 380

Asp Asn Pro Asp Gly Gly Tyr Ile Cys Phe Cys Pro Gly Val Tyr Ser
385                 390                 395                 400

Gly Phe Asn Cys Glu Lys Lys Ile Asp Tyr Cys Ser Ser Asn Pro Cys
                405                 410                 415

Ala Asn Gly Ala Arg Cys Glu Asp Leu Gly Asn Ser Tyr Ile Cys Gln
                420                 425                 430

Cys Gln Glu Gly Phe Ser Gly Arg Asn Cys Asp Asp Asn Leu Asp Asp
            435                 440                 445

Cys Thr Ser Phe Pro Cys Gln Asn Gly Gly Thr Cys Gln Asp Gly Ile
        450                 455                 460

Asn Asp Tyr Ser Cys Thr Cys Pro Pro Gly Tyr Ile Gly Lys Asn Cys
465                 470                 475                 480

Ser Met Pro Ile Thr Lys Cys Glu His Asn Pro Cys His Asn Gly Ala
                485                 490                 495

Thr Cys His Glu Arg Asn Asn Arg Tyr Val Cys Gln Cys Ala Arg Gly
            500                 505                 510

Tyr Gly Gly Asn Asn Cys Gln Phe Leu Leu Pro Glu Glu Lys Pro Val
        515                 520                 525

Val Val Asp Leu Thr Glu Lys Tyr Thr Glu Gly Ser Gly Gln Phe
530                 535                 540

Pro Trp Ile Ala Val Cys Ala Gly Ile Val Leu Val Leu Met Leu Leu
545                 550                 555                 560

Leu Gly Cys Ala Ala Val Val Val Cys Val Arg Val Arg Val Gln Lys
                565                 570                 575

Arg Arg His Gln Pro Glu Ala Cys Arg Gly Glu Ser Lys Thr Met Asn
            580                 585                 590

Asn Leu Ala Asn Cys Gln Arg Glu Lys Asp Ile Ser Val Ser Phe Ile
            595                 600                 605

Gly Thr Thr Gln Ile Lys Asn Thr Asn Lys Lys Ile Asp Phe Leu Ser
        610                 615                 620

Glu Ser Asn Asn Glu Lys Asn Gly Tyr Lys Pro Arg Tyr Pro Ser Val
625                 630                 635                 640

Asp Tyr Asn Leu Val His Glu Leu Lys Asn Glu Asp Ser Pro Lys Glu
                645                 650                 655

Glu Arg Ser Lys Cys Glu Ala Lys Cys Ser Ser Asn Asp Ser Asp Ser
            660                 665                 670

Glu Asp Val Asn Ser Val His Ser Lys Arg Asp Ser Ser Glu Arg Arg
        675                 680                 685

Arg Pro Asp Ser Ala Tyr Ser Thr Ser Lys Asp Thr Lys Tyr Gln Ser
        690                 695                 700

Val Tyr Val Ile Ser Asp Glu Lys Asp Glu Cys Ile Ile Ala Thr Glu
705                 710                 715                 720

Val

<210> SEQ ID NO 13
<211> LENGTH: 2692
<212> TYPE: DNA
<213> ORGANISM: Mus sp.

<400> SEQUENCE: 13
ctgcaggaat tcsmycgcat gctcccggcc gccatgggcc gtcggagcgc gctagccctt    60
```

```
gccgtggtct ctgccctgct gtgccaggtc tggagctccg gcgtatttga gctgaagctg      120
caggagttcg tcaacaagaa ggggctgctg gggaaccgca actgctgccg cggggggctct     180 ggcccgcctt cgcgcctgcag gaccttcttt cgcgtatgcc tcaagcacta ccaggccagc    240
gtgtcaccgg agccaccctg cacctacggc agtgccgtca cgccagtgct gggtgtcgac      300
tccttcagcc tgcctgatgg cgcaggcatc gaccccgcct tcagcaaccc catccgattc      360
cccttcggct tcacctggcc aggtaccttc tctctgatca ttgaagccct ccatacagac      420
tctcccgatg acctcgcaac agaaaaccca gaaagactca tcagccgcct gaccacacag      480
aggcacctca ctgtgggaga agaatggtct caggaccttc acagtagcgg ccgcacagac      540
ctccggtact cttaccggtt tgtgtgtgac gagcactact acggagaagg ttgctctgtg      600
ttctgccgac ctcgggatga cgcctttggc cacttcacct gcggggacag aggggagaag      660
atgtgcgacc ctggctggaa aggccagtac tgcactgacc caatctgtct gccagggtgt      720
gatgaccaac atggatactg tgacaaacca ggggagtgca agtgcagagt tggctggcag      780
ggccgctact gcgatgagtg catccgatac ccaggttgtc tccatggcac tgccagcaa      840 ccctggcagt gtaactgcca ggaaggctgg gggggccttt tctgcaacca agacctgaac      900
tactgtactc accataagcc gtgcaggaat ggagccaccct gcaccaacac gggccagggg     960
agctacacat gttcctgccg acctgggtat acaggtgcca actgtgagct ggaagtagat      1020
gagtgtgctc ctagcccctg caagaacgga gcgagctgca cggaccttga ggacagcttc      1080
tcttgcacct gccctcccgg cttctatggc aaggtctgtg agctgagcgc catgacctgt      1140
gcagatggcc cttgcttcaa tggaggacga tgttcagata ccctgacgg aggctacacc      1200 tgccattgcc ccttgggctt ctctggcttc aactgtgaga gaagatgga tctctgcggc      1260 tcttccccctt gttctaacgg tgccaagtgt gtggacctcg caactctta cctgtgccgg     1320 tgccaggctg gcttctccgg gaggtactgc gaggacaatg tggatgactg tgcctcctcc      1380
ccgtgtgcaa atgggggcac ctgccgggac agtgtgaacg acttctcctg tacctgccca     1440
cctggctaca cggcaagaa ctgcagcgcc cctgtcagca ggtgtgagca tgcaccctgc      1500
cataatgggg ccacctgcca ccagagggc cagcgctaca tgtgtgagtg cgcccagggc     1560 tatgcggcc ccaactgcca gtttctgctc cctgagccac caccaggcc catggtggtg       1620 gacctcagtg agaggcatat ggagagccag ggcgggccct tcccctgggt ggccgtgtgt     1680
gccggggtgg tgcttgtcct cctgctgctg ctgggctgtg ctgctgtggt ggtctgcgtc      1740
cggctgaagc tacagaaaca ccagcctcca cctgaaccct gtgggggaga gacagaaacc      1800
atgaacaacc tagccaattg ccagcgcgag aaggacgttt ctgttagcat cattgggctc      1860
acccagatca agaacaccaa caagaaggcg actttcacg gggaccatgg agccgagaag      1920
agcagcttta aggtccgata ccccactgtg gactataacc tcgttcgaga cctcaaggga     1980
gatgaagcca cggtcaggga tacacacagc aaacgtgaca ccaagtgcca gtcacagagc     2040
tctgcaggag aagagaagat cgccccaaca cttaggggtg gggagattcc tgacagaaaa     2100
aggccagagt ctgtctactc tacttcaaag gacaccaagt accagtcggt gtatgttctg     2160
tctgcagaaa aggatgagtg tgttatagcg actgaggtgt aagatggaag cgatgtggca     2220
aaattcccat ttctcttaaa taaaattcca aggatatagc cccgatgaat gctgctgaga     2280
gaggaaggga gaggaaaccc agggactgct gctgagaacc aggttcaggc gaacgtggtt     2340
ctctcagagt tagcagaggc gcccgacact gccagcctag gctttggctg ccgctggact     2400
```

```
gcctgctggt tgttcccatt gcactatgga cagttgcttt gaagagtata tatttaaatg    2460
gacgagtgac ttgattcata taggaagcac gcactgccca cacgtctatc ttggattact    2520
atgagccagt ctttccttga actagaaaca caactgcctt tattgtcctt tttgatactg    2580
agatgtgttt ttttttttc ctagacggga aaaagaaaac gtgtgttatt tttttttggga    2640 tttgtaaaaa tattttcat gattatggga gagctcccaa cgcgttggag gt             2692
```

<210> SEQ ID NO 14
<211> LENGTH: 722
<212> TYPE: PRT
<213> ORGANISM: Mus sp.

<400> SEQUENCE: 14

```
Met Gly Arg Arg Ser Ala Leu Ala Leu Ala Val Val Ser Ala Leu Leu
1               5                   10                  15

Cys Gln Val Trp Ser Ser Gly Val Phe Glu Leu Lys Leu Gln Glu Phe
            20                  25                  30

Val Asn Lys Lys Gly Leu Leu Gly Asn Arg Asn Cys Cys Arg Gly Gly
        35                  40                  45

Ser Gly Pro Pro Cys Ala Cys Arg Thr Phe Phe Arg Val Cys Leu Lys
    50                  55                  60

His Tyr Gln Ala Ser Val Ser Pro Glu Pro Pro Cys Thr Tyr Gly Ser
65                  70                  75                  80

Ala Val Thr Pro Val Leu Gly Val Asp Ser Phe Ser Leu Pro Asp Gly
                85                  90                  95

Ala Gly Ile Asp Pro Ala Phe Ser Asn Pro Ile Arg Phe Pro Phe Gly
            100                 105                 110

Phe Thr Trp Pro Gly Thr Phe Ser Leu Ile Ile Glu Ala Leu His Thr
        115                 120                 125

Asp Ser Pro Asp Asp Leu Ala Thr Glu Asn Pro Glu Arg Leu Ile Ser
    130                 135                 140

Arg Leu Thr Thr Gln Arg His Leu Thr Val Gly Glu Glu Trp Ser Gln
145                 150                 155                 160

Asp Leu His Ser Ser Gly Arg Thr Asp Leu Arg Tyr Ser Tyr Arg Phe
                165                 170                 175

Val Cys Asp Glu His Tyr Tyr Gly Glu Gly Cys Ser Val Phe Cys Arg
            180                 185                 190

Pro Arg Asp Asp Ala Phe Gly His Phe Thr Cys Gly Asp Arg Gly Glu
        195                 200                 205

Lys Met Cys Asp Pro Gly Trp Lys Gly Gln Tyr Cys Thr Asp Pro Ile
    210                 215                 220

Cys Leu Pro Gly Cys Asp Asp Gln His Gly Tyr Cys Asp Lys Pro Gly
225                 230                 235                 240

Glu Cys Lys Cys Arg Val Gly Trp Gln Gly Arg Tyr Cys Asp Glu Cys
                245                 250                 255

Ile Arg Tyr Pro Gly Cys Leu His Gly Thr Cys Gln Gln Pro Trp Gln
            260                 265                 270

Cys Asn Cys Gln Glu Gly Trp Gly Gly Leu Phe Cys Asn Gln Asp Leu
        275                 280                 285

Asn Tyr Cys Thr His His Lys Pro Cys Arg Asn Gly Ala Thr Cys Thr
    290                 295                 300

Asn Thr Gly Gln Gly Ser Tyr Thr Cys Ser Cys Arg Pro Gly Tyr Thr
305                 310                 315                 320

Gly Ala Asn Cys Glu Leu Glu Val Asp Glu Cys Ala Pro Ser Pro Cys
```

```
                    325                 330                 335
Lys Asn Gly Ala Ser Cys Thr Asp Leu Glu Asp Ser Phe Ser Cys Thr
                340                 345                 350
Cys Pro Pro Gly Phe Tyr Gly Lys Val Cys Glu Leu Ser Ala Met Thr
                355                 360                 365
Cys Ala Asp Gly Pro Cys Phe Asn Gly Gly Arg Cys Ser Asp Asn Pro
                370                 375                 380
Asp Gly Gly Tyr Thr Cys His Cys Pro Leu Gly Phe Ser Gly Phe Asn
385                 390                 395                 400
Cys Glu Lys Lys Met Asp Leu Cys Gly Ser Ser Pro Cys Ser Asn Gly
                405                 410                 415
Ala Lys Cys Val Asp Leu Gly Asn Ser Tyr Leu Cys Arg Cys Gln Ala
                420                 425                 430
Gly Phe Ser Gly Arg Tyr Cys Glu Asp Asn Val Asp Asp Cys Ala Ser
                435                 440                 445
Ser Pro Cys Ala Asn Gly Gly Thr Cys Arg Asp Ser Val Asn Asp Phe
                450                 455                 460
Ser Cys Thr Cys Pro Pro Gly Tyr Thr Gly Lys Asn Cys Ser Ala Pro
465                 470                 475                 480
Val Ser Arg Cys Glu His Ala Pro Cys His Asn Gly Ala Thr Cys His
                485                 490                 495
Gln Arg Gly Gln Arg Tyr Met Cys Glu Cys Ala Gln Gly Tyr Gly Gly
                500                 505                 510
Pro Asn Cys Gln Phe Leu Leu Pro Glu Pro Pro Gly Pro Met Val
                515                 520                 525
Val Asp Leu Ser Glu Arg His Met Glu Ser Gln Gly Gly Pro Phe Pro
530                 535                 540
Trp Val Ala Val Cys Ala Gly Val Val Leu Val Leu Leu Leu Leu Leu
545                 550                 555                 560
Gly Cys Ala Ala Val Val Cys Val Arg Leu Lys Leu Gln Lys His
                565                 570                 575
Gln Pro Pro Pro Glu Pro Cys Gly Gly Glu Thr Glu Thr Met Asn Asn
                580                 585                 590
Leu Ala Asn Cys Gln Arg Glu Lys Asp Val Ser Val Ser Ile Ile Gly
                595                 600                 605
Ala Thr Gln Ile Lys Asn Thr Asn Lys Lys Ala Asp Phe His Gly Asp
                610                 615                 620
His Gly Ala Glu Lys Ser Ser Phe Lys Val Arg Tyr Pro Thr Val Asp
625                 630                 635                 640
Tyr Asn Leu Val Arg Asp Leu Lys Gly Asp Glu Ala Thr Val Arg Asp
                645                 650                 655
Thr His Ser Lys Arg Asp Thr Lys Cys Gln Ser Gln Ser Ser Ala Gly
                660                 665                 670
Glu Glu Lys Ile Ala Pro Thr Leu Arg Gly Gly Glu Ile Pro Asp Arg
                675                 680                 685
Lys Arg Pro Glu Ser Val Tyr Ser Thr Ser Lys Asp Thr Lys Tyr Gln
                690                 695                 700
Ser Val Tyr Val Leu Ser Ala Glu Lys Asp Glu Cys Val Ile Ala Thr
705                 710                 715                 720
Glu Val

<210> SEQ ID NO 15
<211> LENGTH: 525
```

<212> TYPE: DNA
<213> ORGANISM: Homo sapiens

<400> SEQUENCE: 15

```
tacgatgaay aacctggcga actgccagcg tcagaaggac atctcagtca gcatcatcgg      60
ggcyacgtca gatcargaac accaacaaga aggcggactt ymcascgggg gaccasagcg     120
tccgacaaga atggmtttca aggccygcta ccccagcgtg gactataact cgtgcaggac     180
ctcaagggtg acgacaccgc cgtcaggacg tcgcacagca agcgtgacac caagtgccag     240
tccccaggct cctcagggag gagaagggga ccccgaccac actcaggggk tgcgtgctgc     300
gggccgggct caggagggggg tacctggggg gtgtcttcct ggaaccactg ctccgtttct     360
cttcccaaat gttctcatgc attcattgtg gattttctct attttccttt tagtggagaa     420
gcatctgaaa gaaaaaggcc ggactcgggc tgttcaactt caaaagacac caagtaccag     480
tcggtgtacg tcatatccga ggagaaggac gagtgcgtca tcgca                     525
```

<210> SEQ ID NO 16
<211> LENGTH: 1981
<212> TYPE: DNA
<213> ORGANISM: Homo sapiens
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (678)..(678)
<223> OTHER INFORMATION: n is a, c, g, or t
<220> FEATURE:
<221> NAME/KEY: misc_feature
<222> LOCATION: (689)..(689)
<223> OTHER INFORMATION: n is a, c, g, or t
<220> FEATURE:
<221> NAME/KEY: misc_feature
<222> LOCATION: (1246)..(1246)
<223> OTHER INFORMATION: n is a, c, g, or t
<220> FEATURE:
<221> NAME/KEY: misc_feature
<222> LOCATION: (1287)..(1287)
<223> OTHER INFORMATION: n is a, c, g, or t
<220> FEATURE:
<221> NAME/KEY: misc_feature
<222> LOCATION: (1492)..(1492)
<223> OTHER INFORMATION: n is a, c, g, or t
<220> FEATURE:
<221> NAME/KEY: misc_feature
<222> LOCATION: (1524)..(1524)
<223> OTHER INFORMATION: n is a, c, g, or t
<220> FEATURE:
<221> NAME/KEY: misc_feature
<222> LOCATION: (1569)..(1569)
<223> OTHER INFORMATION: n is a, c, g, or t
<220> FEATURE:
<221> NAME/KEY: misc_feature
<222> LOCATION: (1621)..(1621)
<223> OTHER INFORMATION: n is a, c, g, or t
<220> FEATURE:
<221> NAME/KEY: misc_feature
<222> LOCATION: (1656)..(1656)
<223> OTHER INFORMATION: n is a, c, g, or t
<220> FEATURE:
<221> NAME/KEY: misc_feature
<222> LOCATION: (1738)..(1738)
<223> OTHER INFORMATION: n is a, c, g, or t
<220> FEATURE:
<221> NAME/KEY: misc_feature
<222> LOCATION: (1857)..(1857)
<223> OTHER INFORMATION: n is a, c, g, or t
<220> FEATURE:
<221> NAME/KEY: misc_feature
<222> LOCATION: (1861)..(1861)

```
<223> OTHER INFORMATION: n is a, c, g, or t
<220> FEATURE:
<221> NAME/KEY: misc_feature
<222> LOCATION: (1876)..(1876)
<223> OTHER INFORMATION: n is a, c, g, or t
<220> FEATURE:
<221> NAME/KEY: misc_feature
<222> LOCATION: (1888)..(1888)
<223> OTHER INFORMATION: n is a, c, g, or t
<220> FEATURE:
<221> NAME/KEY: misc_feature
<222> LOCATION: (1899)..(1899)
<223> OTHER INFORMATION: n is a, c, g, or t
<220> FEATURE:
<221> NAME/KEY: misc_feature
<222> LOCATION: (1917)..(1917)
<223> OTHER INFORMATION: n is a, c, g, or t
<220> FEATURE:
<221> NAME/KEY: misc_feature
<222> LOCATION: (1925)..(1925)
<223> OTHER INFORMATION: n is a, c, g, or t
<220> FEATURE:
<221> NAME/KEY: misc_feature
<222> LOCATION: (1931)..(1931)
<223> OTHER INFORMATION: n is a, c, g, or t
<220> FEATURE:
<221> NAME/KEY: misc_feature
<222> LOCATION: (1935)..(1935)
<223> OTHER INFORMATION: n is a, c, g, or t
<220> FEATURE:
<221> NAME/KEY: misc_feature
<222> LOCATION: (1942)..(1943)
<223> OTHER INFORMATION: n is a, c, g, or t
<220> FEATURE:
<221> NAME/KEY: misc_feature
<222> LOCATION: (1952)..(1954)
<223> OTHER INFORMATION: n is a, c, g, or t
<220> FEATURE:
<221> NAME/KEY: misc_feature
<222> LOCATION: (1968)..(1968)
<223> OTHER INFORMATION: n is a, c, g, or t

<400> SEQUENCE: 16
cattgggtac gggcccccct cgaggtcgac ggtatcgata agcttgatat cgaattccgg      60
cttcacctgg ccgggcacct tctctctgat tattgaagct ctccacacag attctcctga    120
tgacctcgca acagaaaacc cagaaagact catcagccgc ctggccaccc agaggcacct    180
gacggtgggc gaggagtggt cccaggacct gcacagcagc ggccgcacgg acctcaagta    240
ctcctaccgc ttcgtgtgtg acgaacacta ctacggagag ggctgctccg ttttctgccg    300
tccccgggac gatgccttcg gccacttcac ctgtggggag cgtggggaga aagtgtgcaa    360
ccctggctgg aaagggccct actgcacaga gccgatctgc ctgcctggat gtgatgagca    420
gcatggattt tgtgacaaac cagcccaatg caagtgcaga gtgggctggc agggccggta    480
ctgtgacgag tgtatccgct atccaggctg tctccatggc acctgccagc agccctggca    540
gtgcaactgc caggaaggnt gggggggcct tttctgcaac caggacctga actactgcac    600
acaccataag ccctgcaaga atcgagccac ctgcaacaaa cacgggccag gggagctac    660 acttggtctt tggccggnct ggggtacana gggtgccacc tgcgaagctt ggggattgga    720
cgagttgttg accccagccc ttggtaagaa cggagggagc ttgacggatc ttcggagaac    780
agctactcct gtacctgccc acccggcttc tacggcaaaa tctgtgaatt gagtgccatg    840
acctgtgcgg acgcccttg ctttaacggg ggtcggtgct cagacagccc cgatggaggg    900
tacagctgcc gctgccccgt gggctactcc ggcttcaact gtgagaagaa aattgactac    960
tgcagctctt cacctgttc taatggtgcc aagtgtgtgg acctcggtga tgcctacctg    1020
tgccgctgcc aggccggctt ctcggggagg cactgtgacg acaacgtgga cgactgcgcc    1080
```

-continued

```
tcctccccgt gcgccaacgg gggcacctgc cgggatggcg tgaacgactt ctcctgcacc      1140
tgcccgcctg gctacacggg caggaactgc agtgccccg ccagcaggtg cgagcacgca       1200
ccctgccaca tgggccac ctgccacgag aggggccacc gctatntgtg cgagtgtgcc        1260
cgaagctacg ggggtcccaa ctgccanttc ctgctccccg aaactgcccc ccggccca       1320 cggtggtgga aactccccta aaaaaaccta aaagggccgg gggggccca tccccttggt      1380 ggacgtgtgc gccggggtca tccttgtcct catgctgctg ctgggctgtc ccgctgtggt     1440
ggtctgcgtc cggctgaggc tgcagaagca ccggccccca gccgacccct gncgggggga     1500
gacggagacc atgaacaacc tggncaactg ccagcgtgag aaggacatct cagtcagcat     1560
catcggggnc acgcagatca agaacaccaa caagaaggcg acttccacg gggaccacag      1620 ngccgacaag aatggcttca aggcccgcta cccagnggtg gactataacc tcgtgcagga    1680
cctcaagggt gacgacaccg ccgtcaggga cgcgcacagc aagcgtgaca ccaagtgnca    1740
gccccagggc tcctcagggg aggagaaggg gaccccgac ccacactcag ggggtggagg     1800
aagcatcttg aaagaaaaag gccggacttc gggcttgttc aactttcaaa agacaancaa   1860
ngtacaagtc ggtgtncgtc atttccgnag gaggaaggnt gactgcgtca taggaanttg    1920
aggtngtaaa ntggnagttg annttggaaa gnnntccccc gattcccntt tcaaagtttt   1980
t                                                                    1981
```

<210> SEQ ID NO 17
<211> LENGTH: 192
<212> TYPE: PRT
<213> ORGANISM: Homo sapiens

<400> SEQUENCE: 17

```
Gly Phe Thr Trp Pro Gly Thr Phe Ser Leu Ile Ile Glu Ala Leu His
1               5                   10                  15

Thr Asp Ser Pro Asp Asp Leu Ala Thr Glu Asn Pro Glu Arg Leu Ile
            20                  25                  30

Ser Arg Leu Ala Thr Gln Arg His Leu Thr Val Gly Glu Glu Trp Ser
        35                  40                  45

Gln Asp Leu His Ser Ser Gly Arg Thr Asp Leu Lys Tyr Ser Tyr Arg
    50                  55                  60

Phe Val Cys Asp Glu His Tyr Tyr Gly Glu Gly Cys Ser Val Phe Cys
65                  70                  75                  80

Arg Pro Arg Asp Asp Ala Phe Gly His Phe Thr Cys Gly Glu Arg Gly
                85                  90                  95

Glu Lys Val Cys Asn Pro Gly Trp Lys Gly Pro Tyr Cys Thr Glu Pro
            100                 105                 110

Ile Cys Leu Pro Gly Cys Asp Glu Gln His Gly Phe Cys Asp Lys Pro
        115                 120                 125

Gly Glu Cys Lys Cys Arg Val Gly Trp Gln Gly Arg Tyr Cys Asp Glu
    130                 135                 140

Cys Ile Arg Tyr Pro Gly Cys Leu His Gly Thr Cys Gln Gln Pro Trp
145                 150                 155                 160

Gln Cys Asn Cys Gln Glu Gly Trp Gly Gly Leu Phe Cys Asn Gln Asp
                165                 170                 175

Leu Asn Tyr Cys Thr His His Lys Pro Cys Lys Asn Gly Ala Thr Cys
            180                 185                 190
```

<210> SEQ ID NO 18

```
<211> LENGTH: 6
<212> TYPE: PRT
<213> ORGANISM: Homo sapiens
<300> PUBLICATION INFORMATION:
<310> PATENT DOCUMENT NUMBER: WO 9701571 Fig 14
<312> PUBLICATION DATE: 1997-01-16

<400> SEQUENCE: 18

Thr Asn Thr Gly Gln Gly
1               5

<210> SEQ ID NO 19
<211> LENGTH: 9
<212> TYPE: PRT
<213> ORGANISM: Homo sapiens

<400> SEQUENCE: 19

Lys Asn Gly Gly Ser Leu Thr Asp Leu
1               5

<210> SEQ ID NO 20
<211> LENGTH: 157
<212> TYPE: PRT
<213> ORGANISM: Homo sapiens

<400> SEQUENCE: 20

Glu Asn Ser Tyr Ser Cys Thr Cys Pro Pro Gly Phe Tyr Gly Lys Ile
1               5                   10                  15

Cys Glu Leu Ser Ala Met Thr Cys Ala Asp Gly Pro Cys Phe Asn Gly
                20                  25                  30

Gly Arg Cys Ser Asp Ser Pro Asp Gly Gly Tyr Ser Cys Arg Cys Pro
            35                  40                  45

Val Gly Tyr Ser Gly Phe Asn Cys Glu Lys Lys Ile Asp Tyr Cys Ser
    50                  55                  60

Ser Ser Pro Cys Ser Asn Gly Ala Lys Cys Val Asp Leu Gly Asp Ala
65                  70                  75                  80

Tyr Leu Cys Arg Cys Gln Ala Gly Phe Ser Gly Arg His Cys Asp Asp
                85                  90                  95

Asn Val Asp Asp Cys Ala Ser Ser Pro Cys Ala Asn Gly Gly Thr Cys
                100                 105                 110

Arg Asp Gly Val Asn Asp Phe Ser Cys Thr Cys Pro Pro Gly Tyr Thr
            115                 120                 125

Gly Arg Asn Cys Ser Ala Pro Ala Ser Arg Cys Glu His Ala Pro Cys
    130                 135                 140

His Asn Gly Ala Thr Cys His Glu Arg Gly His Arg Tyr
145                 150                 155

<210> SEQ ID NO 21
<211> LENGTH: 12
<212> TYPE: PRT
<213> ORGANISM: Homo sapiens

<400> SEQUENCE: 21

Cys Glu Cys Ala Arg Ser Tyr Gly Gly Pro Asn Cys
1               5                   10

<210> SEQ ID NO 22
<211> LENGTH: 5
<212> TYPE: PRT
<213> ORGANISM: Homo sapiens

<400> SEQUENCE: 22
```

Phe Leu Leu Pro Glu
1               5

<210> SEQ ID NO 23
<211> LENGTH: 4
<212> TYPE: PRT
<213> ORGANISM: Homo sapiens

<400> SEQUENCE: 23

Pro Pro Gly Pro
1

<210> SEQ ID NO 24
<211> LENGTH: 25
<212> TYPE: PRT
<213> ORGANISM: Homo sapiens

<400> SEQUENCE: 24

Leu Leu Leu Gly Cys Ala Ala Val Val Cys Val Arg Leu Arg Leu
1               5                   10                  15

Gln Lys His Arg Pro Pro Ala Asp Pro
            20                  25

<210> SEQ ID NO 25
<211> LENGTH: 10
<212> TYPE: PRT
<213> ORGANISM: Homo sapiens

<400> SEQUENCE: 25

Arg Gly Glu Thr Glu Thr Met Asn Asn Leu
1               5                   10

<210> SEQ ID NO 26
<211> LENGTH: 14
<212> TYPE: PRT
<213> ORGANISM: Homo sapiens

<400> SEQUENCE: 26

Asn Cys Gln Arg Glu Lys Asp Ile Ser Val Ser Ile Ile Gly
1               5                   10

<210> SEQ ID NO 27
<211> LENGTH: 16
<212> TYPE: PRT
<213> ORGANISM: Homo sapiens

<400> SEQUENCE: 27

Thr Gln Ile Lys Asn Thr Asn Lys Lys Ala Asp Phe His Gly Asp His
1               5                   10                  15

<210> SEQ ID NO 28
<211> LENGTH: 11
<212> TYPE: PRT
<213> ORGANISM: Homo sapiens

<400> SEQUENCE: 28

Ala Asp Lys Asn Gly Phe Lys Ala Arg Tyr Pro
1               5                   10

<210> SEQ ID NO 29
<211> LENGTH: 26
<212> TYPE: PRT
<213> ORGANISM: Homo sapiens

```
-continued

<400> SEQUENCE: 29

Val Asp Tyr Asn Leu Val Gln Asp Leu Lys Gly Asp Asp Thr Ala Val
1               5                   10                  15

Arg Asp Ala His Ser Lys Arg Asp Thr Lys
            20                  25

<210> SEQ ID NO 30
<211> LENGTH: 13
<212> TYPE: PRT
<213> ORGANISM: Homo sapiens

<400> SEQUENCE: 30

Gln Pro Gln Gly Ser Ser Gly Glu Glu Lys Gly Thr Pro
1               5                   10

<210> SEQ ID NO 31
<211> LENGTH: 4
<212> TYPE: PRT
<213> ORGANISM: Homo sapiens

<400> SEQUENCE: 31

Pro Thr Leu Arg
1

<210> SEQ ID NO 32
<211> LENGTH: 4
<212> TYPE: PRT
<213> ORGANISM: Homo sapiens

<400> SEQUENCE: 32

Arg Lys Arg Pro
1
```